(12) United States Patent
Aharoni et al.

(10) Patent No.: US 8,252,978 B2
(45) Date of Patent: Aug. 28, 2012

(54) SHINE CLADE OF TRANSCRIPTION FACTORS AND THEIR USE

(75) Inventors: Asaph Aharoni, Tel-Aviv (IL); Chital Dixit, Wageingen (NL); Andy Pereira, Ede (NL)

(73) Assignee: Stichting Dienst Landbouwkundig Onderzoek, Wageningen (NL)

( * ) Notice: Subject to any disclaimer, the term of this patent is extended or adjusted under 35 U.S.C. 154(b) by 975 days.

(21) Appl. No.: 11/629,080

(22) PCT Filed: Jun. 9, 2005

(86) PCT No.: PCT/NL2005/000418
§ 371 (c)(1),
(2), (4) Date: Nov. 12, 2008

(87) PCT Pub. No.: WO2005/120215
PCT Pub. Date: Dec. 22, 2005

(65) Prior Publication Data
US 2009/0300790 A1 Dec. 3, 2009

(30) Foreign Application Priority Data

Jun. 11, 2004 (EP) .................................... 04076757

(51) Int. Cl.
C12N 15/82 (2006.01)
A01H 5/00 (2006.01)
A01H 5/08 (2006.01)
A01H 5/10 (2006.01)

(52) U.S. Cl. ..................................... 800/289; 800/320.2

(58) Field of Classification Search .......................... None
See application file for complete search history.

(56) References Cited

U.S. PATENT DOCUMENTS 7,511,190 B2 * 3/2009 Creelman et al. ............. 800/282

FOREIGN PATENT DOCUMENTS

| EP | 1 033 405 | | 9/2000 |
|----|-----------|---|--------|
| WO | WO 03/013228 | * | 2/2003 |
| WO | WO 03/13228 | | 2/2003 |
| WO | WO 2004/031349 | | 4/2004 |

OTHER PUBLICATIONS

Broun P. et al. WIN1, a transcriptional activator of epidermal wax accumulation in *Arabidopsis*. Proc Natl Acad Sci U S A. Mar. 30, 2004;101(13):4706-11. Epub Mar. 22, 2004.*
O'Toole, J. C. et al. (1979), Epicuticular Wax and Cuticular Resistance in Rice. Physiologia Plantarum, 47: 239-244.*
Rhee et al. Epicuticular wax accumulation and fatty acid elongation activities are induced during leaf development of leeks. Plant Physiol. Mar. 1998;116(3):901-11.*
Broun et al. WIN1, a transcriptional activator of epidermal wax accumulation in Arabidopsis. Proc Natl Acad Sci U S A. Mar. 30, 2004;101(13):4706-11. Epub Mar. 22, 2004.*
Hiratsu et al. Dominant repression of target genes by chimeric repressors that include the EAR motif, a repression domain, in *Arabidopsis* Plant J. Jun. 2003;34(5):733-9.*
Broun et al. WIN1, a transcriptional activator of epidermal wax accumulation in *Arabidopsis*. Proc Natl Acad Sci U S A. Mar. 30, 2004 ;101(13):4706-11. Epub Mar. 22, 2004.*
Blum, A., Australian Journal of Agricultural Research 56:1159-1168 (2005).
Pierre Broun et al., WIN1, a transcriptional activator of epidermal wax accumulation in *Arabidopsis*, PNAS, Mar. 30, 2004, pp. 4706-4711, vol. 101. (XP-002300982).
Keiichiro Hiratsu et al., Dominant repression of target genes by chimeric repressors that include the EAR motif, a repression domain, in *Arabidopsis*, The Plan Journal, 2003, pp. 733-739, No. 34. (XP-002300983).
J. Alonso et al. Genome-Wide Insertional Mutagenesis of *Arabidopsis thaliana*, Science, Aug. 1, 2003, pp. 653-657, vol. 301 (XP-002300984).
Asaph Aharoni et al., The SHINE Clade of AP2 Domain Transcription Factors Activates Wax Biosynthesis, Alters Cuticle Properties, and Confers Drought Tolerance when Overexpressed in *Arabidopsis*, The Plan Cell, Sep. 2004, pp. 2463-2480, vol. 16. (XP-002300985).

* cited by examiner

*Primary Examiner* — Cynthia Collins
(74) *Attorney, Agent, or Firm* — Browdy and Neimark, PLLC

(57) ABSTRACT

The present invention relates to the field of transgenic plants with given phenotypes, especially plants with enhanced drought tolerance. Provided are SHINE proteins and nucleic acid sequences encoding these, which are useful in conferring these phenotypes to plants.

8 Claims, 4 Drawing Sheets

SEQUENCE LISTING

```
<160> NUMBER OF SEQ ID NOS: 24

<210> SEQ ID NO 1
<211> LENGTH: 1133
<212> TYPE: DNA
<213> ORGANISM: unknown
<220> FEATURE:
<223> OTHER INFORMATION: Arabidopsis thaliana genomic DNA encoding
      SHN1
<220> FEATURE:
<221> NAME/KEY: ATG
<222> LOCATION: (69)..(71)
<220> FEATURE:
<221> NAME/KEY: Intron
<222> LOCATION: (149)..(446)

<400> SEQUENCE: 1
atcttacata tattactcat catcaagttc ctactttctc tctgacaaac atcacagagt      60
aagtaagaat ggtacagacg aagaagttca gaggtgtcag gcaacgccat tggggttctt     120
gggtcgctga gattcgtcat cctctcttgt acctttcttc tttctttcct ttttctctgc     180
gttgttcatt tatttcctct ctctgatcca ttaaagtaca caaccacaca tacatatata     240
```

-continued

| | |
|---|---|
| tacatgatcg tagctaactc atttctggtt tatcttcctt tgttgttttc ctcttcttag | 300 |
| ctaacacata aaatcatttt aacatctaga tacgtaaata tcaataagtt attgcttaaa | 360 |
| aattctacta tatatatata tatatatata ttcaccatgc ttaattatta attttgacat | 420 |
| gcgtgatgat ctttcaaaat aaaaaggaaa cggaggattt ggctagggac gttcgagacc | 480 |
| gcagaggagg cagcaagagc atacgacgag gccgccgttt taatgagcgg ccgcaacgcc | 540 |
| aaaaccaact ttcccctcaa caacaacaac accggagaaa cttccgaggg caaaaccgat | 600 |
| atttcagctt cgtccacaat gtcatcctca acatcatctt catcgctctc ttccatcctc | 660 |
| agcgccaaac tgaggaaatg ctgcaagtct ccttccccat ccctcacctg cctccgtctt | 720 |
| gacacagcca gctcccatat cggcgtctgg cagaaacggg ccggttcaaa gtctgactcc | 780 |
| agctgggtca tgacggtgga gctaggtccc gcaagctcct cccaagagac tactagtaaa | 840 |
| gcttcacaag acgctattct tgctccgacc actgaagttg aaattggtgg cagcagagaa | 900 |
| gaagtattgg atgaggaaga aaaggttgct ttgcaaatga tagaggagct tctcaataca | 960 |
| aactaaatct tatttgctta tatatatgta cctatttca ttgctgattt acagccaaaa | 1020 |
| taatcaatta taccgtgtat tttatagatg ttttatatta aaaggttgtt agctatatat | 1080 |
| tgtttctctt tttccacatt tgtatctaat aaagtattgg tgtttgtaac taa | 1133 |

<210> SEQ ID NO 2
<211> LENGTH: 1076
<212> TYPE: DNA
<213> ORGANISM: unknown
<220> FEATURE:
<223> OTHER INFORMATION: Arabidopsis thaliana genomic DNA encoding SHN2
<220> FEATURE:
<221> NAME/KEY: ATG
<222> LOCATION: (1)..(3)
<220> FEATURE:
<221> NAME/KEY: Intron
<222> LOCATION: (81)..(586)

<400> SEQUENCE: 2

| | |
|---|---|
| atggtacatt cgaggaagtt ccgaggtgtc cgccagcgac aatggggttc ttgggtctct | 60 |
| gagattcgcc atcctctatt gtaagtaatt ggctctctat atacatatat gatctccatt | 120 |
| gtttactgtt ttcctgctta ggattacata ttatataatg ttgtagttgc ttttctcata | 180 |
| tgaagctact atctttattc tttagtatat ttcatcaaaa ctttatttgt atattaaaac | 240 |
| aaacgctcta ctattgctta acaatctaca aaatattaaa aggaattaaa agttaaaacc | 300 |
| aaccatgcat gctaatcaaa gttaagttat cgactgattt tcatctactt gattctttga | 360 |
| ttatttttgt aaattaaatg tggtaatttc taaggttagt ttggatttca gctcaaaact | 420 |
| taattgaaat gtttacttgg attttgtaac taatataaaa attactaaaa tcctttttta | 480 |
| acgtgaatgt tatatgatac caaaacgtta aaaattatat ttcaaaattc atatcatcat | 540 |
| atgtagtgta tttagtattt acacgtgtgt gtgatatatt aatcaggaag agaagagtgt | 600 |
| ggcttggaac tttcgaaacg gcagaagcgg ctgcaagagc atacgaccaa gcggctcttc | 660 |
| taatgaacgg ccaaaacgct aagaccaatt tccctgtcgt aaaatcagag gaaggctccg | 720 |
| atcacgttaa agatgttaac tctccgttga tgtcaccaaa gtcattatct gagcttttga | 780 |
| acgctaagct aaggaagagc tgcaaagacc taacgccttc tttgacgtgt ctccgtcttg | 840 |
| atactgacag ttcccacatt ggagtttggc agaaacgggc cgggtcgaaa acaagtccga | 900 |
| cttgggtcat gcgcctcgaa cttgggaacg tagtcaacga aagtgcggtt gacttagggt | 960 |
| tgactacgat gaacaaacaa aacgttgaga aagaagaaga agaagaagaa gctattatta | 1020 | gtgatgagga tcagttagct atggagatga tcgaggagtt gctgaattgg agttga        1076

<210> SEQ ID NO 3
<211> LENGTH: 1517
<212> TYPE: DNA
<213> ORGANISM: unknown
<220> FEATURE:
<223> OTHER INFORMATION: Arabidopsis thaliana genomic DNA encoding
      SHN3
<220> FEATURE:
<221> NAME/KEY: ATG
<222> LOCATION: (162)..(164)
<220> FEATURE:
<221> NAME/KEY: Intron
<222> LOCATION: (241)..(785)

<400> SEQUENCE: 3
atcagtagag aggacgtggg aaaagcagag agttaagtga gtagttggag atagaaagat        60
cagagacgag gaatctctct cccactctca ctttctctcc tattcttagt tcgtgtcaga       120
aacacacaga gaaattaaga accctaattt aaaacagaag aatggtacat tcgaagaagt       180
tccgaggtgt ccgccagcgt cagtgggstt cttgggtttc tgagattcgt catcctctct       240
tgtcagttct ctctccctct ctatctatta atagagacaa cagtataaat ctgtttatgc       300
aagtccatgc tatgagttaa gtttacattt ttggtgtacg tgtagggcag ttttctgatc       360
attgattata ttttcgaaga ttcatgcaaa gctcttataa tatcatgcat ttttgtttaa       420
gtcgttttcc ttattttttt ccaattaaaa acccacgtt tattaacata tacatatgtt        480
gagtatttgt acttttttgtg ttgtattttg aaattttgag tgtacataaa tttaaatgct      540
ttgtcatata attgatactg atgtattttc tatgtcttag ttggattata gaaaatcata       600
tagcaaagaa ttgggaagga acgaacacta ctcactataa actttcctca aaagaaaac        660
gacccaattt attatcagta acaatttata acaaatttgt tgtgtgtttg ttttagtact       720
ttgaagtttg aataaaatgt gtgttttttg cttacgtaac ttatgtgagc tatcaggaag       780
agaagagtgt ggctaggaac attcgacacg gcggaaacag cggctagagc ctacgaccaa       840
gccgcggttc taatgaacgg ccagagcgcg aagactaact tccccgtcat caaatcgaac       900
ggttcaaatt ccttggagat taactctgcg ttaaggtctc ccaaatcatt atcggaacta       960
ttgaacgcta agctaaggaa gaactgtaaa gaccagacac cgtatctgac gtgtctccgc      1020
ctcgacaacg acagctcaca catcggcgtc tggcagaaac gcgccgggtc aaaaacgagt      1080
ccaaactggg tcaagcttgt tgaactaggt gacaaagtta acgcacgtcc cggtggtgat      1140
attgagacta ataagatgaa ggtacgaaac gaagacgttc aggaagatga tcaaatggcg      1200
atgcagatga tcgaggagtt gcttaactgg acctgtcctg gatctggatc cattgcacag      1260
gtctaaagga gaatcattga attatatgat caagataata atatagttga gggttaataa      1320
taatcgaggg taagtaattt acgtgtagct aataattaat ataattttcg aacatatata      1380
tgaatatatg atagctctag aaatgagtac gtatatatac gtaaacattt ttcctcaaat      1440
atagtatatg tgttgtgatt ctaagacttg taaactgata tggcctactg tttaagagt       1500
agttgatatt ttctatt                                                      1517

<210> SEQ ID NO 4
<211> LENGTH: 834
<212> TYPE: DNA
<213> ORGANISM: unknown
<220> FEATURE:
<223> OTHER INFORMATION: Arabidopsis thaliana shn1 transcript -continued

```
<400> SEQUENCE: 4
atcttacata tattactcat catcaagttc ctactttctc tctgacaaac atcacagagt      60
aagtaagaat ggtacagacg aagaagttca gaggtgtcag gcaacgccat tggggttctt     120
gggtcgctga gattcgtcat cctctcttga aacggaggat ttggctaggg acgttcgaga     180
ccgcagagga ggcagcaaga gcatacgacg aggccgccgt tttaatgagc ggccgcaacg     240
ccaaaaccaa ctttcccctc aacaacaaca acaccggaga aacttccgag ggcaaaaccg     300
atatttcagc ttcgtccaca atgtcatcct caacatcatc ttcatcgctc tcttccatcc     360
tcagcgccaa actgaggaaa tgctgcaagt ctccttcccc atccctcacc tgcctccgtc     420
ttgacacagc cagctcccat atcggcgtct ggcagaaacg ggccggttca aagtctgact     480
ccagctgggt catgacggtg gagctaggtc ccgcaagctc ctcccaagag actactagta     540
aagcttcaca agacgctatt cttgctccga ccactgaagt tgaaattggt ggcagcagag     600
aagaagtatt ggatgaggaa gaaaaggttg cttttgcaaat gatagaggag cttctcaata     660
caaactaaat cttatttgct tatatatatg tacctatttt cattgctgat ttacagccaa     720
aataatcaat tataccgtgt attttataga tgttttatat taaaaggttg ttagctatat     780
ttgtttctct ttttccacat ttgtatctaa taaagtattg gtgtttgtaa ctaa           834

<210> SEQ ID NO 5
<211> LENGTH: 570
<212> TYPE: DNA
<213> ORGANISM: unknown
<220> FEATURE:
<223> OTHER INFORMATION: Arabidopsis thaliana shn2 transcript

<400> SEQUENCE: 5
atggtacatt cgaggaagtt ccgaggtgtc cgccagcgac aatggggttc ttgggtctct      60
gagattcgcc atcctctatt gaagagaaga gtgtggcttg aactttcga aacggcagaa     120 gcggctgcaa gagcatacga ccaagcggct cttctaatga acggcaaaaa cgctaagacc     180
aatttccctg tcgtaaaatc agaggaaggc tccgatcacg ttaaagatgt taactctccg     240
ttgatgtcac caaagtcatt atctgagctt ttgaacgcta agctaaggaa gagctgcaaa     300
gacctaacgc cttctttgac gtgtctccgt cttgatactg acagttccca cattggagtt     360
tggcagaaac gggccgggtc gaaaacaagt ccgacttggg tcatgcgcct cgaacttggg     420
aacgtagtca acgaaagtgc ggttgactta gggttgacta cgatgaacaa acaaaacgtt     480
gagaaagaag aagaagaaga agaagctatt attagtgatg aggatcagtt agctatggag     540
atgatcgagg agttgctgaa ttggagttga                                       570

<210> SEQ ID NO 6
<211> LENGTH: 944
<212> TYPE: DNA
<213> ORGANISM: unknown
<220> FEATURE:
<223> OTHER INFORMATION: Arabidopsis thaliana shn3 transcript

<400> SEQUENCE: 6
agagagttaa gtgagtagtt ggagatagaa agatcagaga cgaggaatct ctctcccact      60
ctcactttct ctcctattct tagttcgtgt cagaaacaca cagagaaatt aagaaccta     120 atttaaaaca gaagaatggt acattcgaag aagttccgag gtgtccgcca gcgtcagtgg     180
ggttcttggg tttctgagat tcgtcatcct ctcttagtgt ggctaggaac attcgacacg     240
gcggaaacag cggctagagc ctacgaccaa gccgcggttc taatgaacgg ccagagcgcg     300
```

```
aagactaact tccccgtcat caaatcgaac ggttcaaatt ccttggagat taactctgcg    360
ttaaggtctc ccaaatcatt atcggaacta ttgaacgcta agctaaggaa gaactgtaaa    420
gaccagacac cgtatctgac gtgtctccgc ctcgacaacg acagctcaca catcggcgtc    480
tggcagaaac gcgccgggtc aaaaacgagt ccaaactggg tcaagcttgt tgaactaggt    540
gacaaagtta acgcacgtcc cggtggtgat attgagacta ataagatgaa ggtacgaaac    600
gaagacgttc aggaagatga tcaaatggcg atgcagatga tcgaggagtt gcttaactgg    660
acctgtcctg gatctggatc cattgcacag gtctaaagga gaatcattga attatatgat    720
caagataata atatagttga gggttaataa taatcgaggg taagtaattt acgtgtagct    780
aataattaat ataattttcg aacatatata tgaatatatg atagctctag aaatgagtac    840
gtatatatac gtaaacattt ttcctcaaat atagtatatg tgttgtgatt ctaagacttg    900
taaactgata tggcctactg tttaaagagt agttgatatt ttct                    944

<210> SEQ ID NO 7
<211> LENGTH: 600
<212> TYPE: DNA
<213> ORGANISM: unknown
<220> FEATURE:
<223> OTHER INFORMATION: Arabidopsis thaliana SHN1 coding sequence

<400> SEQUENCE: 7
atggtacaga cgaagaagtt cagaggtgtc aggcaacgcc attggggttc ttgggtcgct     60
gagattcgtc atcctctctt gaaacggagg atttggctag gacgttcga gaccgcagag    120 gaggcagcaa gagcatacga cgaggccgcc gtttttaatga gcggccgcaa cgccaaaacc    180
aactttcccc tcaacaacaa caacaccgga gaaacttccg agggcaaaac cgatatttca    240
gcttcgtcca caatgtcatc ctcaacatca tcttcatcgc tctcttccat cctcagcgcc    300
aaactgagga aatgctgcaa gtctccttcc ccatccctca cctgcctccg tcttgacaca    360
gccagctccc atatcggcgt ctggcagaaa cgggccggtt caaagtctga ctccagctgg    420
gtcatgacgg tggagctagg tcccgcaagc tcctcccaag agactactag taaagcttca    480
caagacgcta ttcttgctcc gaccactgaa gttgaaattg gtggcagcag agaagaagta    540
ttggatgagg aagaaaaggt tgctttgcaa atgatagagg agcttctcaa tacaaactaa    600

<210> SEQ ID NO 8
<211> LENGTH: 570
<212> TYPE: DNA
<213> ORGANISM: unknown
<220> FEATURE:
<223> OTHER INFORMATION: Arabidopsis thaliana SHN2 coding sequence

<400> SEQUENCE: 8
atggtacatt cgaggaagtt ccgaggtgtc cgccagcgac aatggggttc ttgggtctct     60
gagattcgcc atcctctatt gaagagaaga gtgtggcttg gaactttcga acggcagaa    120 gcggctgcaa gagcatacga ccaagcggct cttctaatga acggccaaaa cgctaagacc    180
aatttccctg tcgtaaaatc agaggaaggc tccgatcacg ttaaagatgt taactctccg    240
ttgatgtcac caaagtcatt atctgagctt ttgaacgcta agctaaggaa gagctgcaaa    300
gacctaacgc cttcttttgac gtgtctccgt cttgatactg acagttccca cattggagtt    360
tggcagaaac gggccgggtc gaaaacaagt ccgacttggg tcatgcgcct cgaacttggg    420
aacgtagtca acgaaagtgc ggttgactta gggttgacta cgatgaacaa acaaaacgtt    480
gagaaagaag aagaagaaga agaagctatt attagtgatg aggatcagtt agctatggag    540
```

-continued atgatcgagg agttgctgaa ttggagttga                                              570

<210> SEQ ID NO 9
<211> LENGTH: 561
<212> TYPE: DNA
<213> ORGANISM: unknown
<220> FEATURE:
<223> OTHER INFORMATION: Arabidopsis thaliana SHN3 coding sequence

<400> SEQUENCE: 9
atggtacatt cgaagaagtt ccgaggtgtc cgccagcgtc agtggggttc ttgggtttct    60
gagattcgtc atcctctctt agtgtggcta ggaacattcg acacggcgga aacagcggct   120
agagcctacg accaagccgc ggttctaatg aacggccaga gcgcgaagac taacttcccc   180
gtcatcaaat cgaacggttc aaattccttg gagattaact ctgcgttaag gtctcccaaa   240
tcattatcgg aactattgaa cgctaagcta aggaagaact gtaaagacca cacccgtat   300
ctgacgtgtc tccgcctcga caacgacagc tcacacatcg cgtctggca gaaacgcgcc   360
gggtcaaaaa cgagtccaaa ctgggtcaag cttgttgaac taggtgacaa agttaacgca   420
cgtcccggtg gtgatattga actaataag atgaaggtac gaaacgaaga cgttcaggaa   480
gatgatcaaa tggcgatgca gatgatcgag gagttgctta actggacctg tcctggatct   540
ggatccattg cacaggtcta a                                              561

<210> SEQ ID NO 10
<211> LENGTH: 618
<212> TYPE: DNA
<213> ORGANISM: unknown
<220> FEATURE:
<223> OTHER INFORMATION: Oryza sativa OsSHN1 coding sequence

<400> SEQUENCE: 10
atggtacagc caaagaagaa gtttcgtgga gtcaggcagc ggcactgggg ctcctgggtc    60
tctgagatca gacacccct ccttaaaagg agggtgtggc tgggcacctt tgagacggcc   120
gaggaggctg cgcgagccta cgatgaggct gctgtgctga tgagtggccg caacgccaag   180
accaacttcc ccgtgcagag gaactccacc ggtgatctcg ccacgccgc agaccaggac   240
gcccgtagca atggcggtag caggaactcc tccgcgggca acctgtcaca gattctcagt   300
gctaagctcc gcaagtgctg caaggcgcca tctccgtcct taacctgcct ccgcctcgac   360
cccgagaagt cccacattgg cgtgtggcaa aagcgcgcag gggcccgtgc tgactccaac   420
tgggtgatga cggtggagct caacaaagag gtagaaccaa ctgaacctgc agctcagccc   480
acatcaacag caacagcttc gcaagtgaca atggatgatg aggaaaagat tgcgctgcaa   540
atgatcgagg agttgctgag caggagcagt ccagcttcac cctcacatgg agagggagag   600
ggtagctttg tcatctga                                                  618

<210> SEQ ID NO 11
<211> LENGTH: 199
<212> TYPE: PRT
<213> ORGANISM: unknown
<220> FEATURE:
<223> OTHER INFORMATION: Arabidopsis SHN1 amino acid sequence

<400> SEQUENCE: 11

Met Val Gln Thr Lys Lys Phe Arg Gly Val Arg Gln Arg His Trp Gly
1               5                   10                  15

Ser Trp Val Ala Glu Ile Arg His Pro Leu Leu Lys Arg Arg Ile Trp
            20                  25                  30

```
Leu Gly Thr Phe Glu Thr Ala Glu Ala Ala Arg Ala Tyr His Glu
         35                  40                  45

Ala Ala Val Leu Met Ser Gly Arg Asn Ala Lys Thr Asn Phe Pro Leu
 50                  55                  60

Asn Asn Asn Asn Thr Gly Glu Thr Ser Glu Gly Lys Thr Asp Ile Ser
 65                  70                  75                  80

Ala Ser Ser Thr Met Ser Ser Ser Thr Ser Ser Ser Ser Leu Ser Ser
                 85                  90                  95

Ile Leu Ser Ala Lys Leu Arg Lys Cys Cys Lys Ser Pro Ser Pro Ser
                100                 105                 110

Leu Thr Cys Leu Arg Leu Asp Thr Ala Ser Ser His Ile Gly Val Trp
            115                 120                 125

Gln Lys Arg Ala Gly Ser Lys Ser Asp Ser Ser Trp Val Met Thr Val
        130                 135                 140

Glu Leu Gly Pro Ala Ser Ser Ser Gln Glu Thr Thr Ser Lys Ala Ser
145                 150                 155                 160

Gln Asp Ala Ile Leu Ala Pro Thr Thr Glu Val Glu Ile Gly Gly Ser
                165                 170                 175

Arg Glu Glu Val Leu Asp Glu Glu Glu Lys Val Ala Leu Gln Met Ile
            180                 185                 190

Glu Glu Leu Leu Asn Thr Asn
        195

<210> SEQ ID NO 12
<211> LENGTH: 189
<212> TYPE: PRT
<213> ORGANISM: unknown
<220> FEATURE:
<223> OTHER INFORMATION: Arabidopsis SHN2 amino acid sequence

<400> SEQUENCE: 12

Met Val His Ser Arg Lys Phe Arg Gly Val Arg Gln Arg Gln Trp Gly
 1               5                  10                  15

Ser Trp Val Ser Glu Ile Arg His Pro Leu Leu Lys Arg Arg Val Trp
            20                  25                  30

Leu Gly Thr Phe Glu Thr Ala Glu Ala Ala Arg Ala Tyr Asp Gln
         35                  40                  45

Ala Ala Leu Leu Met Asn Gly Gln Asn Ala Lys Thr Asn Phe Pro Val
 50                  55                  60

Val Lys Ser Glu Glu Gly Ser Asp His Val Lys Asp Val Asn Ser Pro
 65                  70                  75                  80

Leu Met Ser Pro Lys Ser Leu Ser Glu Leu Leu Asn Ala Lys Leu Arg
                 85                  90                  95

Lys Ser Cys Lys Asp Leu Thr Pro Ser Leu Thr Cys Leu Arg Leu Asp
                100                 105                 110

Thr Asp Ser Ser His Ile Gly Val Trp Gln Lys Arg Ala Gly Ser Lys
            115                 120                 125

Thr Ser Pro Thr Trp Val Met Arg Leu Glu Leu Gly Asn Val Val Asn
        130                 135                 140

Glu Ser Ala Val Asp Leu Gly Leu Thr Thr Met Asn Lys Gln Asn Val
145                 150                 155                 160

Glu Lys Glu Glu Glu Glu Glu Ala Ile Ile Ser Asp Glu Asp Gln
                165                 170                 175

Leu Ala Met Glu Met Ile Glu Glu Leu Leu Asn Trp Ser
        180                 185
```

```
<210> SEQ ID NO 13
<211> LENGTH: 186
<212> TYPE: PRT
<213> ORGANISM: unknown
<220> FEATURE:
<223> OTHER INFORMATION: Arabidopsis SHN3 amino acid sequence

<400> SEQUENCE: 13
```

Met Val His Ser Lys Lys Phe Arg Gly Val Arg Gln Arg Gln Trp Gly
 1               5                  10                  15

Ser Trp Val Ser Glu Ile Arg His Pro Leu Leu Val Trp Leu Gly Thr
            20                  25                  30

Phe Asp Thr Ala Glu Thr Ala Ala Arg Ala Tyr Asp Gln Ala Ala Val
        35                  40                  45

Leu Met Asn Gly Gln Ser Ala Lys Thr Asn Phe Pro Val Ile Lys Ser
    50                  55                  60

Asn Gly Ser Asn Ser Leu Glu Ile Asn Ser Ala Leu Arg Ser Pro Lys
65                  70                  75                  80

Ser Leu Ser Glu Leu Leu Asn Ala Lys Leu Arg Lys Asn Cys Lys Asp
                85                  90                  95

Gln Thr Pro Tyr Leu Thr Cys Leu Arg Leu Asp Asn Asp Ser Ser His
            100                 105                 110

Ile Gly Val Trp Gln Lys Arg Ala Gly Ser Lys Thr Ser Pro Asn Trp
        115                 120                 125

Val Lys Leu Val Glu Leu Gly Asp Lys Val Asn Ala Arg Pro Gly Gly
    130                 135                 140

Asp Ile Glu Thr Asn Lys Met Lys Val Arg Asn Glu Asp Val Gln Glu
145                 150                 155                 160

Asp Asp Gln Met Ala Met Gln Met Ile Glu Glu Leu Leu Asn Trp Thr
                165                 170                 175

Cys Pro Gly Ser Gly Ser Ile Ala Gln Val
            180                 185

```
<210> SEQ ID NO 14
<211> LENGTH: 205
<212> TYPE: PRT
<213> ORGANISM: unknown
<220> FEATURE:
<223> OTHER INFORMATION: Oryza sativa OsSHN1 amino acid sequence

<400> SEQUENCE: 14
```

Met Val Gln Pro Lys Lys Lys Phe Arg Gly Val Arg Gln Arg His Trp
 1               5                  10                  15

Gly Ser Trp Val Ser Glu Ile Arg His Pro Leu Leu Lys Arg Arg Val
            20                  25                  30

Trp Leu Gly Thr Phe Glu Thr Ala Glu Glu Ala Ala Arg Ala Tyr Asp
        35                  40                  45

Glu Ala Ala Val Leu Met Ser Gly Arg Asn Ala Lys Thr Asn Phe Pro
    50                  55                  60

Val Gln Arg Asn Ser Thr Gly Asp Leu Ala Thr Ala Ala Asp Gln Asp
65                  70                  75                  80

Ala Arg Ser Asn Gly Gly Ser Arg Asn Ser Ser Ala Gly Asn Leu Ser
                85                  90                  95

Gln Ile Leu Ser Ala Lys Leu Arg Lys Cys Cys Lys Ala Pro Ser Pro
            100                 105                 110

Ser Leu Thr Cys Leu Arg Leu Asp Pro Glu Lys Ser His Ile Gly Val
        115                 120                 125

Trp Gln Lys Arg Ala Gly Ala Arg Ala Asp Ser Asn Trp Val Met Thr

```
                130             135             140
Val Glu Leu Asn Lys Glu Val Glu Pro Thr Glu Pro Ala Ala Gln Pro
145                 150                 155                 160

Thr Ser Thr Ala Thr Ala Ser Gln Val Thr Met Asp Asp Glu Glu Lys
                165                 170                 175

Ile Ala Leu Gln Met Ile Glu Glu Leu Leu Ser Arg Ser Ser Pro Ala
            180                 185                 190

Ser Pro Ser His Gly Glu Gly Glu Gly Ser Phe Val Ile
            195                 200                 205

<210> SEQ ID NO 15
<211> LENGTH: 61
<212> TYPE: PRT
<213> ORGANISM: unknown
<220> FEATURE:
<223> OTHER INFORMATION: consensus middle domain of SHN proteins
<220> FEATURE:
<221> NAME/KEY: misc_feature
<222> LOCATION: (2)..(4)
<223> OTHER INFORMATION: any amino acid
<220> FEATURE:
<221> NAME/KEY: misc_feature
<222> LOCATION: (6)..(7)
<223> OTHER INFORMATION: any amino acid
<220> FEATURE:
<221> NAME/KEY: misc_feature
<222> LOCATION: (8)..(8)
<223> OTHER INFORMATION: S (Ser) or N (Asn)
<220> FEATURE:
<221> NAME/KEY: misc_feature
<222> LOCATION: (11)..(11)
<223> OTHER INFORMATION: any amino acid
<220> FEATURE:
<221> NAME/KEY: misc_feature
<222> LOCATION: (12)..(12)
<223> OTHER INFORMATION: I (Ile) or L (leu)
<220> FEATURE:
<221> NAME/KEY: misc_feature
<222> LOCATION: (14)..(14)
<223> OTHER INFORMATION: S (Ser) or N (Asn)
<220> FEATURE:
<221> NAME/KEY: misc_feature
<222> LOCATION: (20)..(20)
<223> OTHER INFORMATION: any amino acid
<220> FEATURE:
<221> NAME/KEY: misc_feature
<222> LOCATION: (23)..(24)
<223> OTHER INFORMATION: any amino acid
<220> FEATURE:
<221> NAME/KEY: misc_feature
<222> LOCATION: (25)..(25)
<223> OTHER INFORMATION: S (Ser) or T (Thr)
<220> FEATURE:
<221> NAME/KEY: misc_feature
<222> LOCATION: (27)..(27)
<223> OTHER INFORMATION: S (Ser) or Y (Tyr)
<220> FEATURE:
<221> NAME/KEY: misc_feature
<222> LOCATION: (35)..(36)
<223> OTHER INFORMATION: any amino acid
<220> FEATURE:
<221> NAME/KEY: misc_feature
<222> LOCATION: (37)..(37)
<223> OTHER INFORMATION: S (Ser) or K (Lys)
<220> FEATURE:
<221> NAME/KEY: misc_feature
<222> LOCATION: (49)..(49)
<223> OTHER INFORMATION: S (Ser) or A (Ala)
<220> FEATURE:
<221> NAME/KEY: misc_feature
<222> LOCATION: (50)..(50)
<223> OTHER INFORMATION: K (Lys) or R (Arg)
<220> FEATURE:
<221> NAME/KEY: misc_feature
<222> LOCATION: (51)..(54)
```

```
<223> OTHER INFORMATION: any amino acid
<220> FEATURE:
<221> NAME/KEY: misc_feature
<222> LOCATION: (57)..(57)
<223> OTHER INFORMATION: M (Met) or K (Lys)
<220> FEATURE:
<221> NAME/KEY: misc_feature
<222> LOCATION: (58)..(58)
<223> OTHER INFORMATION: any amino acid
<220> FEATURE:
<221> NAME/KEY: misc_feature
<222> LOCATION: (59)..(59)
<223> OTHER INFORMATION: V (Val) or L (Leu)

<400> SEQUENCE: 15

Ser Xaa Xaa Xaa Ser Xaa Xaa Xaa Leu Ser Xaa Xaa Leu Xaa Ala Lys
1               5                   10                  15

Leu Arg Lys Xaa Cys Lys Xaa Xaa Xaa Pro Xaa Leu Thr Cys Leu Arg
            20                  25                  30

Leu Asp Xaa Xaa Xaa Ser His Ile Gly Val Trp Gln Lys Arg Ala Gly
        35                  40                  45

Xaa Xaa Xaa Xaa Xaa Xaa Trp Val Xaa Xaa Xaa Glu Leu
    50                  55                  60

<210> SEQ ID NO 16
<211> LENGTH: 10
<212> TYPE: PRT
<213> ORGANISM: unknown
<220> FEATURE:
<223> OTHER INFORMATION: consensus "cm" domain of SHN proteins
<220> FEATURE:
<221> NAME/KEY: misc_feature
<222> LOCATION: (1)..(1)
<223> OTHER INFORMATION: V (Val), L (Leu), M (Met) or I (Ile)
<220> FEATURE:
<221> NAME/KEY: misc_feature
<222> LOCATION: (3)..(3)
<223> OTHER INFORMATION: L (Leu) or M (Met)
<220> FEATURE:
<221> NAME/KEY: misc_feature
<222> LOCATION: (4)..(4)
<223> OTHER INFORMATION: Q (Gln) or E (Glu)

<400> SEQUENCE: 16

Xaa Ala Xaa Xaa Met Ile Glu Glu Leu Leu
1               5                   10

<210> SEQ ID NO 17
<211> LENGTH: 1998
<212> TYPE: DNA
<213> ORGANISM: unknown
<220> FEATURE:
<223> OTHER INFORMATION: transcription regulatory sequence of SHN1

<400> SEQUENCE: 17
atttatggag aagttttgaa agtgaacaca aaacaaacat ctttgaattt agtaaatttg      60
aacgaatggc cgttgatcag agttgaatac agaagaagga acggtttct tgtggagaaa     120 tttaaggtgg catttgctgg catttgatca cttctatttc ggggttgact gttcttcgcg    180
ccgttgctgt aaaacctaac ttctttacat tcattgtgga catcagtatg cccaataaa     240 ggcccatttt gaataatcg ggctatttgg tccacacatg aggacacgtg catacgtaag     300
agagtaccag aaaaggagat tcataaaccc gttaaattcg cggttaggaa acttttgcct    360
tttggttgaa acatcgttgg cctcttgcaa gttaattttc ttattctatc gactatttcg    420
gacattcaat cacgtgattt tcgtgtttga aaagatcaac aatttttttt ttcgttaaaa    480
tatctggcat ttaaataaac actatacgta aattttagca gtatgaaatt aactaggctg    540
```

```
atggattcga aaataatac  aataaaacca aaagaaaag  aaaacatgt  attccaaatt    600 acaggagtac tatcatcaat cattcaatct ttaagtagct acaaaagtct acaacaaaaa    660
taaagagaaa caaataata  atttaaaggc tagataattg aaaggaatag tgatatgcaa    720
gttccaaaca caagtatgaa caagagttaa tggaagagac tataattatg aaatatcggt    780
catggactca gggaagtggg gaccctatga taacaagcca ccaccaaatt agcacctcaa    840
aaacaaaaat gtataaacca tattatattg tatattaaat ataagcatac attaggttaa    900
agatgtttgc tcaaaaatta aaagcaaata gatatgagat tgacacctaa acagccttaa    960
tctggaccca atctgacagt tagggcttag gctatgggta cgacaatcaa ctagatatgt   1020
ggacaaaaca ttctactaat tacacaatat acatgtacat ggaccaccct ttaattttta   1080 tttttttgt  cctttactt  tttaacttgt acatgcatgt tgtcaatgtc taattatata   1140 atcactttc  ccctctatgt atgttgtttt atacattgca tgtgttatat ttgatcgcga   1200
gtgaacaacc acttttctca cgcttatta  cgtgttttct ttttgcggca aatcatttta   1260
cgattgatta atcctattca aattcactac ttaaacttac tcccactgaa caaagtccca   1320
actaaagctt ataaattgta taatgtttac attaagtctt ggggattgga ttgacaatga   1380
tgattttggc cgatggttag tgctggttgt taaccaacat gatagtataa tataaaatga   1440
aacattaata tggactgatg ttcggtctta attaccactc cactcttaga tataaaattt   1500
tgcagttaat ggtgaacgca aatttgctta tacgtacgta cgaagctgta tacaaatata   1560
agtaagcatc aaattaaaca gagagagaga ggcgtagtac ttacgtagct atatgatgtg   1620
gacgattgat taggatgtac gtatgctaaa aacaatatac acggccatgt gatacttgta   1680
ccacttgcgc atctctacat atatacgatc caacctttgg aatttatatt gtttaccttt   1740
ataataacca tccttcacat tagcaatcaa tctacaccaa caactacaac taaattctat   1800
ctctctctct ataataaact agcgagcgag gacgtcaaat gtaataagag taagaacaag   1860
tacacctttt catccaccaa aatttaacct atgtatataa atatacaaca ttaccattta   1920
ccaaacatcc atcttacata tattactcat catcaagttc ctactttctc tctgacaaac   1980
atcacagagt aagtaaga                                                 1998
```

<210> SEQ ID NO 18
<211> LENGTH: 1848
<212> TYPE: DNA
<213> ORGANISM: unknown
<220> FEATURE:
<223> OTHER INFORMATION: transcription regulatory sequence of SHN2

<400> SEQUENCE: 18

```
gattgggtac taggttaagg tcaaatatgg ttcaaataaa agttaatatt aaaagatgga     60
aagtatgaag tttatactag tgagttactt gttctttagt tttagaatgg atatatttta    120
ttttattttt atactttaga ccattaagca ggaaaaatat gtaagcaata ctctaatagg    180
tagaagaaac aagagataca agtaaagtag tgcataaaga gatgaaaaca ctgtctttgg    240
tacctctaat tgttaccggc cgttttaata attgataatg ttatagtata tttgtttatt    300
tgacaaatat ctcaaacttt aaaaattaca caaagacaaa gatgtaaaac tatttgcagc    360
atttcaacgg atgcgataga ttacccatta aaaaaaaaaa aaaaaaaaa  aacacgaatg    420 gaatagtctt ttcaatggct aatattagtt ttcacttctg atcacttagt aaaatcatga    480
aagcacacta cattagaatt gtgtccatat tgaggaaaaa agaaagagaa tggtgtacat    540
acataaattt aatacatgtt tattatgaga aagcaacgta cgtaatacat tactttgtct    600
```

```
ctaggtaaca aattgtggat ttccattggt tggtaacaga aaaagaacg  attgggggat    660 aaactacaat atgtgagttt ttttgttcaa actagatgtg aactatatat tggtgaatac    720
ctttgaaaat attacaaaca ttactatcca tcccatagcg tcgtcacctt actcatgact    780
tcaattatag tctgacaata taggactgaa aaacatgatt gcaaatgttg tgaatacatt    840
tattttagca caaagtttta aaagttattg gtctattata cgttgaacct taaatgaacg    900
ttgaaatatc tacgcccttt caccacccga cccaccgaca tttctttggt ttttgttttt    960
ttagatatat atatatatat atttttaatt caaacatgta aattgaatta aactggaaga   1020
taaacaaagc tgcaccagga attcgagccg aacttacgag gtggccttag agctatgtta   1080
ttatgtctac gtacacccaa agtttgaagt acagaattag gttatagatc tgtcttgtgg   1140
aaagaaaaac ttattgctaa tttaggttga ctcagattat aactgtagtt gagatgagac   1200
agtcaatgga gacagatcta taacaaattg atgttttggc aaataaaggt atgatatata   1260
atgtagttat atgataataa aaaaaagcta tgatatatcc tatatatata atgcatgttg   1320
atgtttaaat aaaagaaagc tatatatgtt ttagtttctt tgtgggtatt aaaactcagg   1380
catgagtccc tatgggtc gatcgtggga aaaaaaaaa aaagagagt cctatatgg      1440 catgaaagta acgttagaaa cgaaggtacg agtcgtgtct tcactagatt cattctaata   1500
aagtaaggaa gttgtattca taaataaaga atagatatct attgatgtta cgtccctcac   1560
taaggcttgt gagacaaagt agtgggctca aatatcttaa ttaccaacgt gaatcgaatt   1620
tatatagatc atcgaagaaa ggtcaattta caaacaaaga gaaacttcaa attaaggccc   1680
tatataaata gttagttggg gacgaaccac agtaggatca gggactatat cagtctctat   1740
ctttctctct ctcttctgat tgtccgagtt gtgtctgcta agaagagaga gaaacttaaa   1800
accctaaatt tcaaatcaga aaatatagag tttgaaggaa actaaaag              1848
```

<210> SEQ ID NO 19
<211> LENGTH: 2004
<212> TYPE: DNA
<213> ORGANISM: unknown
<220> FEATURE:
<223> OTHER INFORMATION: transcription regulatory sequence of SHN3

<400> SEQUENCE: 19

```
tctagaccaa tattttatta ttattcatat aattaaacgt ttattgaatt attttagctc     60
taaaaaatat aatgaaattt agaattgtta tagaaacttt aaatgactca aaactgatct    120 ttgtttttt  gtcaaccaca cattaattaa aaactgatct ttgttaaaca tctaaatatt    180
gaaaaacaaa aggattacca ccgcacctat cctgcatcgt cttgtaccat ttgcattcat    240
cagagccatt atatattcat gtggctgtca catccttata tacatttcaa cttataaatt    300
taattttgta cgtttagcag atgttggtga attcatttat tcaagcttaa ggtttaactc    360
gttcttgtct cctttaggtt cataacattt aatggacaac aactactcca aatatccgtg    420
gactttacca cgcgacgcac cgacaattct ctagcctttt cattaattga tcagtaaaaa    480
cacttctata attttaatta ttctcagaaa ttttaaccgg tagtaacata aacgtagatg    540
atcgaaaaag atgaaatcga ggtctctgtt ttgtgtcgaa ttaatagatc tataagaaat    600
caaacaatga aaattaaata gatgaatgaa atatgttttg acgacgtttt cacgtcactg    660
tttaagttat ctgttagtaa aatttgatag catttaattt gaattgctat gtaactcgga    720
ataaattcga cggcaagagg tgtgggatgt gatcagtctt ctaattaagt gtaatctttta   780 caaaaaatca gtatgagtta atacaggttt ataaatagaa agacatctac agtaaaacct    840
```

```
ctataaatta ataatgttgg gactgcaaaa ttttattaat ttagaaagat tttaatttat      900
cgataaatta atatttatta atttatagag agattttcgt aatttagtaa cttttcaaaa      960
atttctataa aatttttttc attatagaaa atatctttca aaaatcaatt acaagtaaat     1020
aataatatca tgtttagaaa acaacaccaa aagttttga taaagtaaaa tactataact     1080
aaatttaaat aagaataaat acaaatttta agcaaaaaaa tattagaatt atatttcaaa     1140
ataatttctt acatataatg tatatatagt tgatatattt ataaaattat taatttatga     1200
tattgatggg accatatatt tacataagat ttttttaaaaa gttattatct tattaattta     1260
tcgatttgtg tcactttttta cactgatccc aactcgggac tggaagaatt tattaattta     1320
tagaggttat taatttatcg agtattaatt tatagaggtt taactgtata tgaataattg     1380
aatacacatg ggacatcatt atagttacct tagtacgatt ttatgcattt ggttaccaaa     1440
atccactagg cttcgtaatt ggttgtgggt cagtgtccat tcgatagttt gcattagcga     1500
taaacactta aaacagtaaa acgtgatcta tttttaaaca ataacatttc ttcttatcaa     1560
atattcacat aattaatgaa gaaaagagac gaattgatag gcaataagaa atatgatcac     1620
ttggtaccat tgtatgcatg gtatgaactg acatcaagta tttgtacgtt gtagggtaat     1680
tattaacatt gtagaatgac aagtatgatc aaatggaaaa ggattagtta tatgtagcaa     1740
aactagtatt tgtacttgga ctatcttgtc atgtagtttt cctaacgcta tatataatcc     1800
aataacccca tgacacggaa gagatagggg acatacaata aatatcagta gagaggacgt     1860
gggaaaagca gagagttaag tgagtagttg gagatagaaa gatcagagac gaggaatctc     1920
tctcccactc tcactttctc tcctattctt agttcgtgtc agaaacacac agagaaatta     1980
agaaccctaa tttaaaacag aaga                                            2004

<210> SEQ ID NO 20
<211> LENGTH: 1362
<212> TYPE: DNA
<213> ORGANISM: unknown
<220> FEATURE:
<223> OTHER INFORMATION: transcription regulatory sequence of OsSHN1

<400> SEQUENCE: 20
actcagcagt gagcacacac catcatcata accaggctgt gtacatggag ctaccttaga       60
caagcttaaa tgccaaccaa ctccaagcag tcccagatca aaaagctcat gacaacggaa      120
aacttgaaaa agaaaaaaaa aactttacaa gtcttaacca aaaaaactct aaatttacac      180
acacacacac acacacacta aaggcaacac attcttacac atttcaaact ccagttctat      240
agcgcaaaac aagacttgag tgttgaaata tgaagaaagt ttcccaataa gacgagagaa      300
aactgaacac gtcatcacaa ataaagcacg agatattccc aaacgcagtt tgcagcataa      360
gtcttgccat atgagacgcc tagttaagaa caacgtccat gcatccactg gcactcaaag      420
ctcatgactg gaccatatcc acaccccacc atagctgtgg aagaattatg gccatggagt      480
tgatctgaca caaatgcaca attgctttgc agaacaacta gcctagctta tactaatgct      540
ctaggagcta atgtgctaat gtgaatcaac ccggggttgc cccacaatta atgtggctac      600
catgggcgta ggtgagagtg ttaattacca atgtcctagc agagaaggtg gttatgctaa      660
tacccgcaca gttcaccgac agcccccact gcgggccttg tggactggac caccttcacc      720
ttcagttgcc cctcccctga attctctctt cacctctact acctctgtcc cgaaataact      780
ttatttttca cctatcccgt acataccaat acaaagacaa aaataccata atgtcctcta      840
ttttaacaaa tcacaatgca attttacccc actttaacaa actccaatgc atttgtctcc      900
```

```
cacttccata gattcaatat aatgatttac ttaaaagata aaagttattt tgagacaaat    960
aagatggtaa aaaatgaagt tattttggga tagagggaag tatctccagt cctgccttac   1020
ttttatccct tggcacacac ctgctagttg ctactgcttg tgaacccagc ccttggtgat   1080
gttcagtgaa aactaggcca aacacaatct ctttgattct ctctttctat ctctgtatct   1140
ctgatacgta ctatttgacc acctatacgt ctcaccacat ttaacgcggc actgtagacg   1200
caagtacagg ccgcagcagt ttatattcac tcaaacaagt gctttcctcc tccccacac    1260 ctcctccgtt cagttcagag gcgcctagca atagcagctc attgcctcat ctctgcctcc   1320
cctgtccttc tgggggcaga gaatctctcc actgctggaa aa                     1362
```

<210> SEQ ID NO 21
<211> LENGTH: 12
<212> TYPE: PRT
<213> ORGANISM: unknown
<220> FEATURE:
<223> OTHER INFORMATION: EAR repressor domain

<400> SEQUENCE: 21

Leu Asp Leu Asp Leu Glu Leu Arg Leu Gly Phe Ala
1               5                   10

<210> SEQ ID NO 22
<211> LENGTH: 36
<212> TYPE: DNA
<213> ORGANISM: unknown
<220> FEATURE:
<223> OTHER INFORMATION: nucleic acid sequence encoding the EAR
      repressor domain

<400> SEQUENCE: 22

```
ctggatctgg atctagaact ccgtttgggt ttcgct                               36
```

<210> SEQ ID NO 23
<211> LENGTH: 732
<212> TYPE: DNA
<213> ORGANISM: unknown
<220> FEATURE:
<223> OTHER INFORMATION: Oryza sativa cDNA OsSHN2

<400> SEQUENCE: 23

```
atgggacagt cgaagaagaa gttccgcgga gtcaggcagc gccactgggg ctcctgggtc     60
tccgagatca ggcaccctct ccttaagagg agggtgtggc tgggtacctt tgagacggcg    120
gaggaggcgg cgcgggcgta cgacgaggcc gccatcctga tgagcggccg caacgccaag    180
accaacttcc cagtcgcgag gaacgccacg ggggagctca ccggcggcg tgcggtggca     240 gggcgggatg gccgtgtcgg cggcggcagc ggcagctcgt cctcaatgac ggccaacggc    300
ggcgggaaca gcctgtctca gatcctcagc gccaagctcc gcaagtgctg caagacgccg    360
tcgccgtcgc tcacctgcct ccgccttgac ccggagaagt cccacattgg cgtctggcag    420
aagcgcgccg gcgcacgcgc tgactccagc tgggtcatga ccgtcgagct caacaaggac    480
acggccgtgt cgtcggctgc gacggtggca gcagcaacag cagtgtcgtc cagcgaccag    540
ccgactccga gtgacagcac agtcacaacg acgtccacgt ccaccacggg ctcgccgtcg    600
ccaccacctc cggcaatgga cgacgaggag aggatcgcgc tgcagatgat cgaggagctg    660
ctgggcagga gcggcccggg ctcgccgtca catgggctgc tgcacggtgg tgaaggtagc    720
ctcgtcatct ga                                                         732
```

```
<210> SEQ ID NO 24
<211> LENGTH: 243
<212> TYPE: PRT
<213> ORGANISM: unknown
<220> FEATURE:
<223> OTHER INFORMATION: OsSHN2 amino acid sequence

<400> SEQUENCE: 24

Met Gly Gln Ser Lys Lys Phe Arg Gly Val Arg Gln Arg His Trp
1               5                   10                  15

Gly Ser Trp Val Ser Glu Ile Arg His Pro Leu Leu Lys Arg Arg Val
            20                  25                  30

Trp Leu Gly Thr Phe Glu Thr Ala Glu Glu Ala Ala Arg Ala Tyr Asp
                35                  40                  45

Glu Ala Ala Ile Leu Met Ser Gly Arg Asn Ala Lys Thr Asn Phe Pro
        50                  55                  60

Val Ala Arg Asn Ala Thr Gly Glu Leu Thr Pro Ala Ala Ala Val Ala
65                  70                  75                  80

Gly Arg Asp Gly Arg Val Gly Gly Gly Ser Gly Ser Ser Ser Ser Met
                85                  90                  95

Thr Ala Asn Gly Gly Gly Asn Ser Leu Ser Gln Ile Leu Ser Ala Lys
                100                 105                 110

Leu Arg Lys Cys Cys Lys Thr Pro Ser Pro Ser Leu Thr Cys Leu Arg
        115                 120                 125

Leu Asp Pro Glu Lys Ser His Ile Gly Val Trp Gln Lys Arg Ala Gly
    130                 135                 140

Ala Arg Ala Asp Ser Ser Trp Val Met Thr Val Glu Leu Asn Lys Asp
145                 150                 155                 160

Thr Ala Val Ser Ser Ala Ala Thr Val Ala Ala Ala Thr Ala Val Ser
                165                 170                 175

Ser Ser Asp Gln Pro Thr Pro Ser Asp Ser Thr Val Thr Thr Thr Ser
            180                 185                 190

Thr Ser Thr Thr Gly Ser Pro Ser Pro Pro Pro Ala Met Asp Asp
        195                 200                 205

Glu Glu Arg Ile Ala Leu Gln Met Ile Glu Glu Leu Leu Gly Arg Ser
        210                 215                 220

Gly Pro Gly Ser Pro Ser His Gly Leu Leu His Gly Gly Glu Gly Ser
225                 230                 235                 240

Leu Val Ile
```

SHINE CLADE OF TRANSCRIPTION FACTORS AND THEIR USE

FIELD OF THE INVENTION

Figure 1:
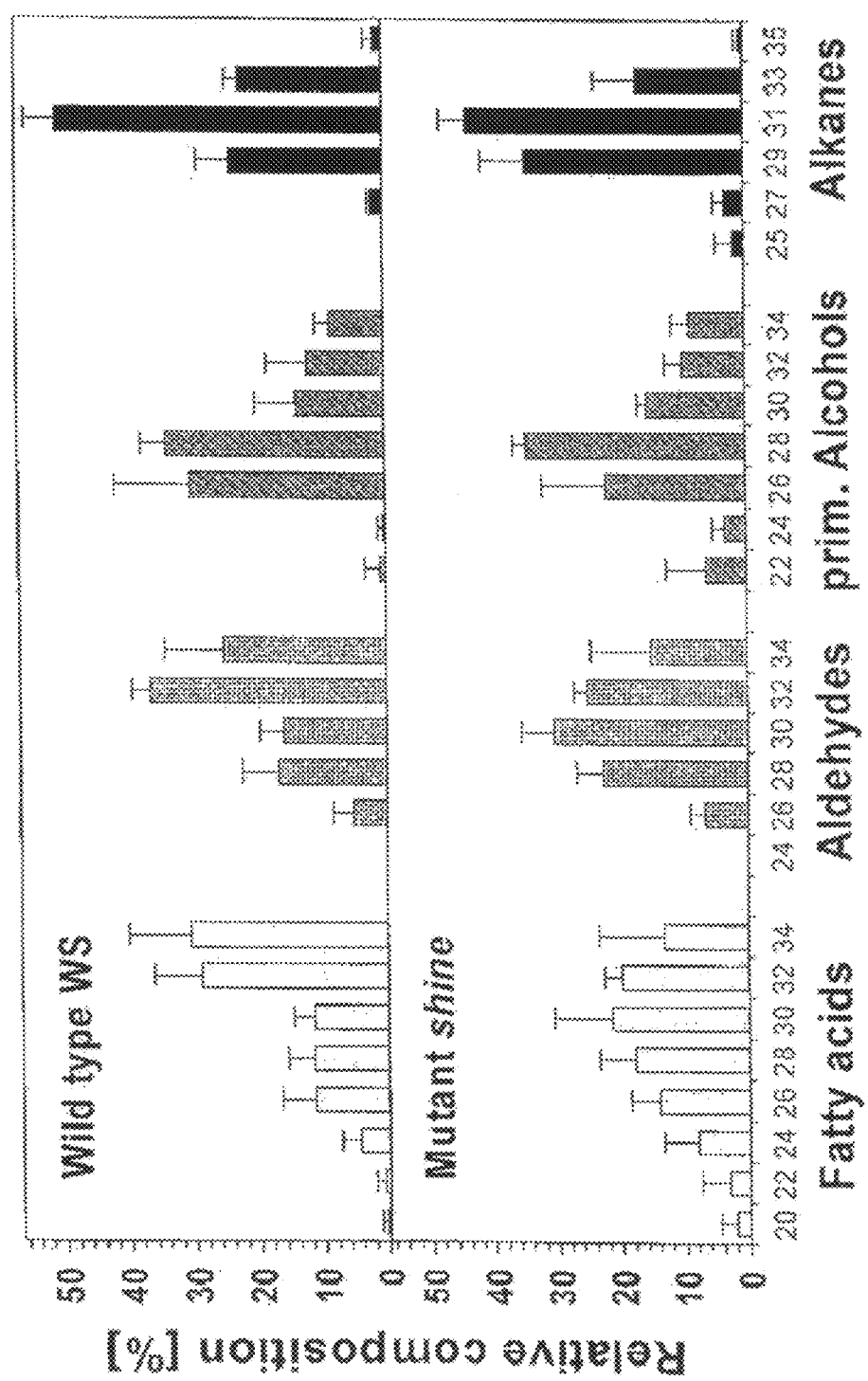

The present invention relates to a novel class of transcription factors, referred herein to as the SHINE clade of transcription factors, and their use to confer various novel phenotypes onto plants, such as drought tolerance and other water use related phenotypes, indehiscence of plant dehiscence zones (conferring for example male sterility or pod shatter resistance) and modification of other cell layers involved in cell separation or in the cell-environment interface. The invention provides nucleic acid sequences encoding SHINE (SHN) proteins, or functional fragments thereof, which are useful for modifying, or newly conferring, one or more novel plant phenotypes. Further provided are isolated SHINE proteins, chimeric genes, nucleic acid vectors, recombinant microorganisms and plants, as well as methods and means for using SHINE (SHN) nucleic acid sequence to confer novel plant phenotypes.

BACKGROUND OF THE INVENTION

The interface between plants and the environment plays a dual role as a protective barrier, as well as a medium for the exchange of gases, water and nutrients. The primary aerial plant surfaces (including leaves, stems, flowers, fruit) are covered by a cuticle, acting as a protective layer, which plays a role in regulating water loss and protects the plant against the surrounding environment (e.g. pathogen damage, insect damage, mechanical damage, UV radiation, frost) (Sieber et al. 2000, Plant Cell 12, 721-737). It is a heterogeneous layer composed mainly of lipids, namely cutin and intracuticular wax, with epicuticular waxes deposited on the surface and has an important role in regulating epidermal permeability and non-stomatal water loss. Without the protective cuticle, transpiration of most land plants would be so rapid that death would result. Cuticle metabolism and the structure of the epidermal surfaces are, therefore, crucial factors in determining plant water management and in protecting plants from environmental stress, both abiotic stresses (such as drought, freezing, salinity, wind, metals, etc.) and biotic stresses (such as plant pathogens or insects). In addition the cuticular layer also has a role in normal plant development processes including the prevention of post-genital organ fusion and pollen-pistil interactions and it has been suggested that cuticle permeability in such processes will also influence cell-to-cell communication by enhancing or attenuating the passage of signal molecules (Pruitt et al. 2000, PNAS USA 97, 1311-1316; Sieber at al. 2000, supra). Such signals could be, for example, required for organ adhesion (moving across the cuticle), or mediating signaling between trichomes and stomata (moving within the developing epidermis) (Lolle et al., 1997, Dev. Biol. 189, 311-321; Krolikowski et al., 2003, Plant J. 35, 501-511).

As tolerance to biotic and abiotic stresses has a direct impact on plant productivity (yield and product quality), mechanisms for conferring or enhancing stress tolerance have been widely studied and various approaches for conferring environmental stress tolerance have been described in the art. One of the most serious abiotic stresses plants have to cope with world-wide is drought stress or dehydration stress. Four-tenths of the world's agricultural land lies in arid or semi-arid regions. Apart from that, also plants grown in regions with relatively high precipitation may suffer spells of drought throughout the growing season. Many agricultural regions, especially in developing countries, have consistently low rain-fall and rely on irrigation to maintain yields. Water is scarce in many regions and its value will undoubtedly increase with global warming, resulting in an even greater need for drought tolerant crop plants, which maintain yield levels (or even have higher yields) and yield quality under low water availability. It has been estimated that the production of 1 kg of cotton requires about 15,000 litres of water in irrigated agriculture, while 1 kg of rice requires 4000 litres. Conferring or enhancing the tolerance of crop plants to short and long spells of drought and reducing the water requirement of crops grown in irrigated agriculture is clearly an important objective.

Although breeding (e.g. marker assisted) for drought tolerance is possible and is being pursued for a range of crop species (mainly cereals, such as maize, upland rice, wheat, sorghum, pearl millet, but also in other species such as cowpea, pigeon pea and *Phaseolus* bean), it is extremely difficult and tedious because drought tolerance or resistance is a complex trait, determined by the interaction of many loci and gene-environment interactions. Single, dominant genes, which confer or improve drought tolerance and which can be easily transferred into high yielding crop varieties and breeding lines are therefore sought after. Most water is lost through the leaves, by transpiration, and many transgenic approaches have focused on modifying the water loss through changing the leaves. For example WO00/73475 describes the expression of a C4 NADP+-malic enzyme from maize in tobacco epidermal cells and guard cells, which, according to the disclosure, increases water use efficiency of the plant by modulating stomatal aperture. Other approaches involve, for example, the expression of osmo-protectants, such as sugars (e.g. trehalose biosynthetic enzymes) in plants in order to increase water-stress tolerance, see e.g. WO99/46370. Yet other approaches have focused on changing the root architecture of plants.

To date another promising approach to enhance drought tolerance is the overexpression of CBF/DREB genes (DREB refers to dehydration response element binding; DRE binding), encoding various AP2/EREBP (ethylene response element binding protein) transcription factors (WO98/09521). Overexpression of the CBF/DREB1 proteins in *Arabidopsis* resulted in an increase in freezing tolerance (also referred to as freeze-induced dehydration tolerance) (Jaglo-Ottosen et al., Science 280, 104-106, 1998; Liu et al., Plant Cell 10, 1391-1406, 1998; Kasuga et al., Nat. Biotechnol. 17, 287-291, 1999; Gilmour et al. Plant Physiol. 124, 1854-1865, 2000) and enhanced the tolerance of the recombinant plants to dehydration caused either by water deficiency or exposure to high salinity (Liu et al., 1998, supra; Kasuga et al., 1999, supra). Another CBF transcription factor, CBF4, has been described to be a regulator of drought adaptation in *Arabidopsis* (Haake et al. 2002, Plant Physiology 130, 639-648).

Despite the availability of some genes which have been shown to enhance drought tolerance in a number of plant species, such as Brassicaceae and Solanaceae, there is a need for the identification of other genes with the ability to confer or improve drought tolerance when expressed in crop plants. In one embodiment, the present invention provides a new family of genes and proteins which fulfil this need.

Apart from the cuticle, forming a protective layer between the leaves and the environment, plants form a range of other protective or cell-separating layers, such as "dehiscence zones" and suberin layers. Dehiscence zones are cell layers formed during cell wall separation processes, such as the abscission of leaves, flowers, fruits (e.g. pods or siliques) or in anther dehiscence. Brassicaceae produces fruits in the form of pods (siliques) in which the two carpel valves (ovary walls) are joined to the replum, a visible suture that divides the two carpels. The dehiscence zone is a layer of only one to three cells in width that extends along the entire length of the valve/replum boundary (Meakin and Roberts, 1990, J. Exp. Botany 41: 995-1002). As the cells in the dehiscence zone separate from one another, the valves detach from the replum, allowing seeds to be dispersed (often prematurely), which is referred to as podshatter or seedshatter. Premature shattering causes significant yield losses in *Brassica* species, such as *Brassica napus* (oilseed rape or "canola" if erucic acid and glucosinolate levels are below a certain threshold value). As breeding for shatter resistance is virtually impossible, due to lack of genetic variation in this trait, transgenic approaches are being explored in order to confer shatter resistance to pod-bearing plants, such as *Brassica napus* or soybean. To date such approaches involve for example a gene referred to as "indehiscent 1" (IND1), identified in *Arabidopsis* (see WO017951), MADS-Box genes AGL1, AGL5 and AGL8 (FUL) (WO99/00503), or the SGT10166 gene (WO0159122). One of the difficulties in transgenic podshatter approaches is that on the one hand it is desired to prevent easy separation of the two pod valves, on the other hand it must still remain possible to separate the valves in order to harvest the seeds.

Another dehiscence process in flowering plants is anther dehiscence, whereby the anther opens to release pollen grains into the environment. Two processes are believed to contribute to anther dehiscence, namely splitting of the anther wall which occurs at the stomium, a specialised group of cell types running the length of the anther, and the inversion of the anther walls which exposes the pollen. Splitting of the anther wall involves cell-to-cell separation at the stomium. Anther development and dehiscence involves many genes, see for an overview Goldberg et al., 1993 (The Plant Cell Vol. 5, 1217-1229). The reduction or prevention of pollen release from plants, or a change in the time point of pollen release, has significant benefits, such as the production of male sterile plants (useful, for example, for hybrid seed production, see WO9626283; Mariani et al. 1990, Nature 347, 737-741; Mariani et al. 1992, Nature 357, 384-387) or prevention (or reduction) of pollen release where this is undesirable, as for example because of risks of allergenicity or risks of releasing pollen of transgenic plants into the environment. Recombinant approaches used to date to confer male sterility involve for example the tissue specific expression of genes encoding cytotoxic proteins, such as the barnase gene (Mariani et al. 1990 and 1992, supra), leading to a selective destruction of specific cell types during anther development (e.g. the tapetum layer).

However, there is still a need to identify novel genes which are suitable to confer shatter resistance or male sterility to plants, especially to crop plants. In one embodiment, the present invention provides a new family of genes and proteins which fulfil this need.

As mentioned above, another protective layer formed in plants is the suberin layer, which is functionally related to the cutin layer and also prevents water loss from specific tissues, blocks pathogen invasion and strengthens the cell wall. Suberin is formed as a protective layer on underground plant cell surfaces such as the root endodermis and also as a strengthening component in cell walls, for example in the root as a Casparian strip in the cell wall of the root endodermis and in bundle sheath cells of grasses. It also covers the cork cells formed in tree bark and is deposited as scar tissue after wounding, for example as a protective layer after leaf abscission or on the surface of wounded potato tubers (Kolattukudy 1981, Ann. Rev. Plant Physiol.; Nawrath 2002, The biopolymers cutin and suberin, "The *Arabidopsis* Book", Eds. C. R. Sommerville and E. M. Meyerowitz, American Society of Plant Biologists, Rockville, Md.). Similar to cutin, suberin consists of a complex mixture of fatty acids and further contains phenolic compounds, such as ferulic acid. Genes involved in suberization and which are useful in modifying suberin formation in plants are generally desirable, for example for improving wound healing properties of tubers or strengthening root formation.

The prior art shows that there is a continuous need for novel genes and methods which are useful for the modification of plant protective layers (epidermis and cuticle, suberin layers) and cell layers involved in cell-to-cell separation processes. The present invention provides a novel class of genes which influence the formation and metabolism of the interface between the plant surface and the environment (wounding sites, root cap cells and some organs at the epidermal layer) and of the interface between cells and cell layer above ground (e.g. dehiscence zones and abscission zones) or below ground (e.g. the endodermis). In addition, the present invention discloses how to use this class of genes to generate plants with novel phenotypes, especially drought tolerance or resistance, male sterility, seed shatter resistance, fruit (e.g. tomatoes) with more solid flesh and a higher concentration of soluble solids, plants (especially tubers) with improved wound healing properties or woody trees with enhanced suberization of cork cells.

General Definitions

The term "nucleic acid sequence" (or nucleic acid molecule) refers to a DNA or RNA molecule in single or double stranded form, particularly a DNA encoding a protein or protein fragment according to the invention. An "isolated nucleic acid sequence" refers to a nucleic acid sequence which is no longer in the natural environment from which it was isolated, e.g. the nucleic acid sequence in a bacterial host cell or in the plant nuclear or plastid genome.

The terms "protein" or "polypeptide" are used interchangeably and refer to molecules consisting of a chain of amino acids, without reference to a specific mode of action, size, 3 dimensional structure or origin. A "fragment" or "portion" of a SHINE protein may thus still be referred to as a "protein". An "isolated protein" is used to refer to a protein which is no longer in its natural environment, for example in vitro or in a recombinant bacterial or plant host cell.

The term "gene" means a DNA sequence comprising a region (transcribed region), which is transcribed into an RNA molecule (e.g. an mRNA) in a cell, operably linked to suitable regulatory regions (e.g. a promoter). A gene may thus comprise several operably linked sequences, such as a promoter, a 5' leader sequence comprising e.g. sequences involved in translation initiation, a (protein) coding region (cDNA or genomic DNA) and a 3'non-translated sequence comprising e.g. transcription termination sites.

A "chimeric gene" (or recombinant gene) refers to any gene, which is not normally found in nature in a species, in particular a gene in which one or more parts of the nucleic acid sequence are present that are not associated with each other in nature. For example the promoter is not associated in nature with part or all of the transcribed region or with another regulatory region. The term "chimeric gene" is understood to include expression constructs in which a promoter or transcription regulatory sequence is operably linked to one or more coding sequences or to an antisense (reverse complement of the sense strand) or inverted repeat sequence (sense and antisense, whereby the RNA transcript forms double stranded RNA upon transcription).

"Expression of a gene" refers to the process wherein a DNA region, which is operably linked to appropriate regulatory regions, particularly a promoter, is transcribed into an RNA, which is biologically active, i.e. which is capable of being translated into a biologically active protein or peptide (or active peptide fragment) or which is active itself (e.g. in posttranscriptional gene silencing or RNAi). An active protein in certain embodiments refers to a protein having a dominant-negative function due to a repressor domain being present. The coding sequence is preferably in sense-orientation and encodes a desired, biologically active protein or peptide, or an active peptide fragment. In gene silencing approaches, the DNA sequence is preferably present in the form of an antisense DNA or an inverted repeat DNA, comprising a short sequence of the target gene in antisense or in sense and antisense orientation. "Ectopic expression" refers to expression in a tissue in which the gene is normally not expressed.

A "transcription regulatory sequence" is herein defined as a nucleic acid sequence that is capable of regulating the rate of transcription of a (coding) sequence operably linked to the transcription regulatory sequence. A transcription regulatory sequence as herein defined will thus comprise all of the sequence elements necessary for initiation of transcription (promoter elements), for maintaining and for regulating transcription, including e.g. attenuators or enhancers. Although mostly the upstream (5') transcription regulatory sequences of a coding sequence are referred to, regulatory sequences found downstream (3') of a coding sequence are also encompassed by this definition.

As used herein, the term "promoter" refers to a nucleic acid fragment that functions to control the transcription of one or more genes, located upstream with respect to the direction of transcription of the transcription initiation site of the gene, and is structurally identified by the presence of a binding site for DNA-dependent RNA polymerase, transcription initiation sites and any other DNA sequences, including, but not limited to transcription factor binding sites, repressor and activator protein binding sites, and any other sequences of nucleotides known to one of skill in the art to act directly or indirectly to regulate the amount of transcription from the promoter. A "constitutive" promoter is a promoter that is active in most tissues under most physiological and developmental conditions. An "inducible" promoter is a promoter that is physiologically (e.g. by external application of certain compounds) or developmentally regulated. A "tissue specific" promoter is only active in specific types of tissues or cells.

As used herein, the term "operably linked" refers to a linkage of polynucleotide elements in a functional relationship. A nucleic acid is "operably linked" when it is placed into a functional relationship with another nucleic acid sequence. For instance, a promoter, or rather a transcription regulatory sequence, is operably linked to a coding sequence if it affects the transcription of the coding sequence. Operably linked means that the DNA sequences being linked are typically contiguous and, where necessary to join two protein encoding regions, contiguous and in reading frame so as to produce a "chimeric protein". A "chimeric protein" or "hybrid protein" is a protein composed of various protein "domains" (or motifs) which is not found as such in nature but which a joined to form a functional protein, which displays the functionality of the joined domains (for example DNA binding or repression leading to a dominant negative function). A chimeric protein may also be a fusion protein of two or more proteins occurring in nature. The term "domain" as used herein means any part(s) or domain(s) of the protein with a specific structure or function that can be transferred to another protein for providing a new hybrid protein with at least the functional characteristic of the domain. Specific domains can also be used to identify protein members belonging to the SHINE clade of transcription factors, such as SHINE orthologs from other plant species. Examples of domains found in SHINE proteins are the AP2 domain, the "mm" domain and the "cm" domain.

The terms "target peptide" refers to amino acid sequences which target a protein to intracellular organelles such as plastids, preferably chloroplasts, mitochondria, or to the extracellular space (secretion signal peptide). A nucleic acid sequence encoding a target peptide may be fused (in frame) to the nucleic acid sequence encoding the amino terminal end (N-terminal end) of the protein.

A "nucleic acid construct" or "vector" is herein understood to mean a man-made nucleic acid molecule resulting from the use of recombinant DNA technology and which is used to deliver exogenous DNA into a host cell. The vector backbone may for example be a binary or superbinary vector (see e.g. U.S. Pat. No. 5,591,616, US2002138879 and WO9506722), a co-integrate vector or a T-DNA vector, as known in the art and as described elsewhere herein, into which a chimeric gene is integrated or, if a suitable transcription regulatory sequence is already present, only a desired nucleic acid sequence (e.g. a coding sequence, an antisense or an inverted repeat sequence) is integrated downstream of the transcription regulatory sequence. Vectors usually comprise further genetic elements to facilitate their use in molecular cloning, such as e.g. selectable markers, multiple cloning sites and the like (see below).

A "host cell" or a "recombinant host cell" or "transformed cell" are terms referring to a new individual cell (or organism) arising as a result of at least one nucleic acid molecule, especially comprising a chimeric gene encoding a desired protein or a nucleic acid sequence which upon transcription yields an antisense RNA or an inverted repeat RNA (or hairpin RNA) for silencing of a target gene/gene family, having been introduced into said cell. The host cell is preferably a plant cell or a bacterial cell. The host cell may contain the nucleic acid construct as an extra-chromosomally (episomal) replicating molecule, or more preferably, comprises the chimeric gene integrated in the nuclear or plastid genome of the host cell.

The term "selectable marker" is a term familiar to one of ordinary skill in the art and is used herein to describe any genetic entity which, when expressed, can be used to select for a cell or cells containing the selectable marker. Selectable marker gene products confer for example antibiotic resistance, or more preferably, herbicide resistance or another selectable trait such as a phenotypic trait (e.g. a change in pigmentation) or a nutritional requirements. The term "reporter" is mainly used to refer to visible markers, such as green fluorescent protein (GFP), eGFP, luciferase, GUS and the like.

The term "ortholog" of a gene or protein refers herein to the homologous gene or protein found in another species, which has the same function as the gene or protein, but (usually) diverged in sequence from the time point on when the species harbouring the genes diverged (i.e. the genes evolved from a common ancestor by speciation). Orthologs of the *Arabidopsis* shn1, shn2 and shn3 genes may thus be identified in other plant species based on both sequence comparisons (e.g. based on percentages sequence identity over the entire sequence or over specific domains) and functional analysis.

The terms "homologous" and "heterologous" refer to the relationship between a nucleic acid or amino acid sequence and its host cell or organism, especially in the context of transgenic organisms. A homologous sequence is thus naturally found in the host species (e.g. a tomato plant transformed with a tomato gene), while a heterologous sequence is not naturally found in the host cell (e.g. a tomato plant transformed with a sequence from potato plants). Depending on the context, the term "homolog" or "homologous" may alternatively refer to sequences which are descendent from a common ancestral sequence (e.g. they may be orthologs).

"Stringent hybridisation conditions" can be used to identify nucleotide sequences, which are substantially identical to a given nucleotide sequence. Stringent conditions are sequence dependent and will be different in different circumstances. Generally, stringent conditions are selected to be about 5° C. lower than the thermal melting point ($T_m$) for the specific sequences at a defined ionic strength and pH. The $T_m$ is the temperature (under defined ionic strength and pH) at which 50% of the target sequence hybridises to a perfectly matched probe. Typically stringent conditions will be chosen in which the salt concentration is about 0.02 molar at pH 7 and the temperature is at least 60° C. Lowering the salt concentration and/or increasing the temperature increases stringency. Stringent conditions for RNA-DNA hybridisations (Northern blots using a probe of e.g. 100 nt) are for example those which include at least one wash in 0.2×SSC at 63° C. for 20 min, or equivalent conditions. Stringent conditions for DNA-DNA hybridisation (Southern blots using a probe of e.g. 100 nt) are for example those which include at least one wash (usually 2) in 0.2×SSC at a temperature of at least 50° C., usually about 55° C., for 20 min, or equivalent conditions. See also Sambrook et al. (1989) and Sambrook and Russell (2001).

"Sequence identity" and "sequence similarity" can be determined by alignment of two peptide or two nucleotide sequences using global or local alignment algorithms. Sequences may then be referred to as "substantially identical" or "essentially similar" when they (when optimally aligned by for example the programs GAP or BESTFIT using default parameters) share at least a certain minimal percentage of sequence identity (as defined below). GAP uses the Needleman and Wunsch global alignment algorithm to align two sequences over their entire length, maximizing the number of matches and minimises the number of gaps. Generally, the GAP default parameters are used, with a gap creation penalty=50 (nucleotides)/8 (proteins) and gap extension penalty=3 (nucleotides)/2 (proteins). For nucleotides the default scoring matrix used is nwsgapdna and for proteins the default scoring matrix is Blosum62 (Henikoff & Henikoff, 1992, PNAS 89, 915-919). Sequence alignments and scores for percentage sequence identity may be determined using computer programs, such as the GCG Wisconsin Package, Version 10.3, available from Accelrys Inc., 9685 Scranton Road, San Diego, Calif. 92121-3752 USA. Alternatively percent similarity or identity may be determined by searching against databases such as FASTA, BLAST, etc.

In this document and in its claims, the verb "to comprise" and its conjugations is used in its non-limiting sense to mean that items following the word are included, but items not specifically mentioned are not excluded. In addition, reference to an element by the indefinite article "a" or "an" does not exclude the possibility that more than one of the element is present, unless the context clearly requires that there be one and only one of the elements. The indefinite article "a" or "an" thus usually means "at least one". It is further understood that, when referring to "sequences" herein, generally the actual physical molecules with a certain sequence of subunits (e.g. amino acids) are referred to.

DETAILED DESCRIPTION OF THE INVENTION

Using activation tagging, the inventors isolated and characterized an *Arabidopsis* gene, referred to as SHN1, the overexpression of which resulted in a number of changes in plant surface structure compared to the wild type. The activation of SHN1 resulted in leaves having a deep shiny green appearance, with a curled structure and an altered cuticle permeability, cuticular wax load/structure and epidermal differentiation. The SHN1 gene was cloned and sequenced and was found to be similar to transcriptional factors defined as AP2/EREBP (Alonso et al. 2003, Science 301, 653-657). This gene has also recently been described in the art to encode a transcriptional activator of epidermal wax accumulation in *Arabidopsis* (Broun et al. 2004, PNAS Vol. 101, 4706-4711). However no other functions of SHN1 have been described and no uses for the SHN1 gene suggested other than activation of wax deposition. Although leaf wax load and composition plays some role in protecting the plant from water loss, the inventors surprisingly found that shn1 expression resulted in an altered cuticle structure, which resulted in an increase in cuticular water loss. This finding was contrary to what might be expected from the phenotype described by Broun et al. (2004, supra). The cuticular water loss of leaves continued beyond the time when stomata close, indicating that non-stomatal water loss was significantly increased. In addition an increase in cuticle permeability due to SHN1 activation was illustrated by a higher elution of chlorophyll when conducting chlorophyll leaching experiments.

It was further surprisingly found that SHN overexpression in monocots, e.g. rice, lead to plants which did not show any changes in epicuticular wax, but were still drought tolerant, proving that the changes to the epicuticular wax layer observed are not functional with respect to generating drought tolerance, but that it is the modified epidermal and cuticle properties which provide the drought tolerant phenotype. This surprising finding could not have been foreseen from Broun et al. (supra) or WO03/013228. From these disclosures one would not expect the SHN gene to be able to confer drought tolerance in plants or plant parts without modifying the epicuticular wax layer, as the mechanism would be expected to be completely dependent on changing the wax composition or content. In contrast to what would be concluded from the prior art, the present invention shows, therefore, that drought tolerant plants can be made, which do not have a modified epicuticular wax layer (i.e. the epicuticular wax remains unchanged in SHN overexpressing plants), i.e. wherein the wax composition and content is unchanged/as in the wild type. Thus, this finding enables the generation of drought tolerant plants, especially monocotyledonous plants but also dicotyledonous plants, having a modified cuticle and epidermis (and therefore being drought tolerant), but wherein the epicuticular wax is not changed (wild type). Similarly, organ specific or tissue specific expression results in drought tolerance/dehydration tolerance of those parts without modifying the epicuticular wax composition and content.

Constitutive expression of SHN1 cDNA in transgenic *Arabidopsis* plants showed the same phenotype as the original activation tag line, although the phenotype was more severe. In addition flower morphology was also affected, which was not the case in the original tagged line, resulting in petals which were folded and in part "hidden" in-between the sepals and the flower interior organs. In addition trichome number and shape was significantly changed in transgenic 35S::SHN1 plants. Most interestingly, epidermal cell differentiation in transgenic lines was altered in two ways. Firstly, pavement cell density on the abaxial side of the leaves was significantly reduced and secondly stomatal density was significantly reduced compared to the wild type. However, cuticle permeability (as determined by water loss and chlorophyll leaching) was again increased, as seen in the original tagged line, with this phenotype being more dramatic than in the original line.

Based on the finding that the SHN1 expression resulted in an increase in cuticular water loss, it was even more surprising to find that 35S::SHN1 transformants showed enhanced drought tolerance and recovery. Thus apparently the increased non-stomatal water loss through the altered cuticle was outweighed by the effect of the reduced stomatal index.

Using in silico analysis two homologs of SHN1 were identified, herein referred to as SHN2 and SHN3 (encoding proteins whose function had not yet been disclosed in the art). Overexpression of SHN2 and SHN3 resulted in similar phenotypes as SHN1 overexpression, confirming the functional relationship between SHN1-SHN3. The SHINE clade of proteins consists, thus, of three members in *Arabidopsis*, defined by their sequence (especially by unique sequence motifs) and function. The SHINE proteins belong to the plant-specific family of AP2/EREBP transcription factors. This super-family of transcription factors contains 141 members in *Arabidopsis thaliana* (Alonso et al. 2003, Science 301, 653-657).

Spatio-temporal expression of SHN1, SHN2 and SHN3 was analyzed by generating transformation vectors comprising about 2 kb of the genomic DNA upstream (5') of the ATG codon of SHN1 (SEQ ID NO: 17), SHN2 (SEQ ID NO: 18) and SHN3 (SEQ ID NO: 19), respectively. The GUS expression pattern showed that SHN1, SHN2 and SHN3 differ in their spatio-temporal expression pattern, although some overlap was observed, as described elsewhere herein.

Nucleic Acid Sequences and Proteins According to the Invention

In one embodiment of the invention nucleic acid sequences and amino acid sequences of members of the SHINE clade of transcription factors are provided (including orthologs), as well as methods for isolating or identifying orthologs of the SHINE clade of other plant species.

The "SHINE clade" of transcription factors is defined herein by the presence of specific amino acid sequence domains in combination with a related in vivo function of the proteins in the formation of plant protective layers or plant cell separation processes. The SHINE clade encompasses, therefore, orthologs of the *Arabidopsis* SHN proteins (SHN1, SHN2 and SHN3), such as but not limited to orthologs from monocotyledonous species (rice, maize, wheat, sorghum, pearl millet, barley and other cereals) or from dicotyledonous plants such as for example Brassicaceae (e.g. *Brassica napus*), cotton, bean, pea, tomato, potato, other vegetable species, etc. Two ortholog member of the SHINE clade have been identified in rice (*Oryza sativa* cv *japonica*) and are herein referred to as OsSHN1 (amino acid SEQ ID NO: 14, encoded by the cDNA sequence of SEQ ID NO: 10) and OsSHN2 (amino acid SEQ ID NO: 24, encoded by the cDNA sequence of SEQ ID NO: 23). OsSHN1 and OsSHN2 are used herein to exemplify how other members of the SHINE clade can be identified in other species (especially in other plant species) and used.

In order to provide guidance as to which proteins are members of the SHINE clade, the essential structural and functional features of members of the SHINE clade is described below. Firstly the amino acid sequences of SHN1 (SEQ ID NO: 11), SHN2 (SEQ ID NO: 12), SHN3 (SEQ ID NO: 13) and OsSHN1 (SEQ ID NO: 14) and OsSHN2 (SEQ ID NO: 24) are described.

SHN1, SHN2 and SHN3 are proteins of 199, 189 and 186 amino acids in length, respectively, while OsSHN1 is 205 amino acids long and OsSHN2 243 amino acids. Each comprises a single AP2 DNA binding domain, a conserved middle domain "mm" and a conserved C-terminal domain "cm". The consensus sequences of these domains are as follows:

```
Consensus middle domain "mm" (61 amino acids)-
                                         SEQ ID NO: 15
S-X-X-X-S-X-X-S/N-L-S-X-I/L-L-S/N-A-K-L-R-K-X-C-
K-X-X-S/T-P-S/Y-L-T-C-L-R-L-D-X-X-S/K-
S-H-I-G-V-W-Q-K-R-A-G-S/A-K/R-X-X-X-X-W-V-M/K-X-
V/L-E-L Consenus C-terminal domain "cm" (10 amino acids)-
                                         SEQ ID NO: 16
V/L/M/I-A-L/M-Q/E-M-I-E-E-L-L
(X refers to any amino acid and consensus sequences are
presented in N- to C-terminal order).
```

The presence of the "mm" domain is one of the distinguishing features of SHINE clade members. Especially the presence of an "mm" domain in combination with a "cm" domain and/or an AP2 domain is characteristic. In one embodiment SHN proteins are defined as comprising at least one "mm" domain and having a function in the formation of protective layers and/or cell separation layers. It is understood that the "mm" domain may be modified without losing its function. For example single amino acid substitutions, deletions or replacements (e.g. conservative amino acid replacements) may be present in the "mm" domain according to the invention. The "mm" domain of SHN proteins can also be defined in terms of sequence identity, whereby domains having a sequence identity of at least 55%, preferably at least 60% or more are encompassed herein (see Table 2).

Alternatively or additionally, SHN proteins may be defined by their amino acid sequence identity over their entire length. SHN proteins have a sequence identity of 50% or more over their entire length (see Table 1) (such as but not limited to 55%, 60%, 70%, 80%, 90% or more), and a sequence identity of 45% or more, preferably at least 50%, 55%, 57%, 58%, 59%, 60%, 70%, 80%, 90%, 95% or more over the middle domain region "mm" (see Table 2).

To illustrate the distinction between SHINE members and non-SHINE members, the *Arabidopsis* sequence with Accession number At5g25190 and the tomato LeERF1 sequence (Accession number AY077626) are included in Table 1, both of which are non-SHINE proteins. Both lack the consensus middle domain "mm", as a result of which the overall sequence identity is much lower (generally below 40% sequence identity with SHINE proteins). In addition the At5g25190 overexpression showed that the function of this protein was not essentially similar to that of SHN1, SHN2 and SHN3, maybe due to the absence of the middle domain. The overexpression lines did not display the phenotypic characteristics of the SHN gene overexpression lines, but exhibited other distinct phenotypes suggesting a different function.

TABLE 1 amino acid sequence identity over entire length

|  | SHN1 | SHN2 | SHN3 | OsSHN1 | At5g25190 | LeERF1 (AY077626) |
|---|---|---|---|---|---|---|
| SHN1 | 100% | 55.9% | 50.2% | 59.3% | 40.2% | 36.6% |
| SHN2 |  | 100% | 66.8% | 50.7% | 38.8% | 32.7% |
| SHN3 |  |  | 100% | 51.5% | 39.7% | 34.4% |

(GAP opening = 8, GAP extension = 2, Blosum62)

TABLE 2 amino acid sequence identity over "mm" domain

|  | SHN1 | SHN2 | SHN3 | OsSHN1 |
|---|---|---|---|---|
| SHN1 | 100% | 68.9% | 65.6% | 75.4% |
| SHN2 |  | 100% | 83.6% | 60.7% |
| SHN3 |  |  | 100% | 60.7% |

(GAP opening = 8, GAP extension = 2, Blosum62)

The SHINE clade members can thus be defined as comprising at least one consensus middle domain and preferably further comprising at least one consensus C-terminal domain and/or at least one AP2 binding domain in addition to an in vivo function which is essentially similar to that of SHN1, SHN2, SHN3 and/or OsSHN1 and/or OsSHN2 when expressed in a host plant. A "function which is essentially similar to the function of SHN1, SHN2, SHN3 and/or OsSHN1 and/or OsSHN2" refers herein to the protein having a proven function in the development/formation of plant protective layers (cuticle layers and/or suberin layers) and/or cell separation processes (dehiscence and/or abscission).

The function of a protein can be tested using a variety of known methods, preferably by comparing the phenotype of transformants constitutively expressing the protein being tested to the phenotype of SHN1, SHN2, SHN3 and/or OsSHN1 and/or OsSHN2 over-expressing transformants of the same host species (and variety) (preferably comprising a chimeric SHN encoding gene stably integrated into the host's genome), allowing a direct comparison of the functional effect on the phenotype of the transformants. It is understood that in any transformation experiments a certain degree of variation in the phenotype of transformants is seen, normally due to position effects in the genome and/or due to copy number. A skilled person will know how to compare transformants to one another, e.g. by selecting single copy number events and analysing their phenotypes. Other methods of determining or confirming in vivo gene/protein function include the generation of knock-out mutants or transient expression studies. Promoter-reporter gene expression studies may also provide information as to the spatio-temporal expression pattern and the role of the protein.

Constitutive (over)expression of a SHINE clade member should result in one or more of the following phenotypic changes compared to the wild type or control transformants:
increased cuticle permeability, especially non-stomatal permeability
reduced stomatal index/density due to altered epidermal cell differentiation,
increased (absolute) cuticular wax load and/or altered wax composition (relative wax composition)
reduced number of trichomes and/or altered trichome structure
shiny green leaves and/or curled leaves.

In a preferred embodiment, however, overexpression results in an epidermal change leading to reduced stomatal index/density, but no change to the epicuticular wax layer. By generating or selecting such plants or plant parts, the plant tissue appearance remains unchanged (i.e. leaves are not shiny and/or curled and have no increased wax load and/or altered wax composition), while the plant (or plant part) has one or more of the novel phenotypes described elsewhere herein. In a preferred embodiment these plants (or plant parts) are monocotyledonous plants, but generation and selection of dicotyledonous plants (or plant parts) which have a novel phenotype but which have an unmodified epicuticular wax layer is also possible. The expression "the epicuticular wax layer is unmodified" refers to the layer being essentially as in the wild type, i.e. if the wild type has no layer, the transformant also has not layer, and if the wild type has a very thin layer, the transformant also has a very thin layer. Especially, the epicuticular wax content and composition is essentially as in the wild type.

An "increased cuticle permeability" refers to the (non-stomatal) water loss occurring through the cuticle and can be measured by, for example, carrying out fresh weight loss experiments or Chlorophyll Leaching Assays, as described in the Examples. The average rate of water loss per gram fresh weight of the transformants, and the total amount of water lost after e.g. 1 hour, is significantly increased compared to controls, especially at least about 3 fold, 5 fold, 10 fold, or more, preferably at least about 5-10 fold. Chlorophyll leaching of transformants are carried out by adding alcohol (e.g. 80% ethanol) to the tissue samples and measuring the absorbance of the samples after a certain period of incubation (see Examples and Lolle et al. 1997, Dev Biol 189, 311-321). The rate of chlorophyll leaching per fresh weight of the transformants, and the total amount of chlorophyll leached after e.g. 1 hour, is significantly increased compared to controls, especially at least about 3 fold, 5 fold, 10 fold, 12 fold, 15 fold or more, preferably at least about 5-10 fold. For example, for 1 µmol Chlorophyll/mg fresh weight leached after 1 hour in the control about 12 µmol Chlorophyll/mg fresh weight leached in the transformant (see Examples).

An "altered epidermal differentiation" refers to a significantly reduced stomatal density (number of stomata per $mm^2$) and stomatal index, compared to that of control plants or tissues. Stomatal density is reduced by at least about 15%, 20%, 30% or more in tissue of transformants compared to suitable controls. The stomatal index is reduced by at least 25%, more preferably by at least 30%, 40%, 45% or more compared to the stomatal index of controls. The stomatal index can be determined by making imprints of leaf (abaxial) surfaces and counting pavement cells and stomata under a microscope, as described in the examples. The stomatal index can be calculated according to Mishra 1997 (Ann. Bot. 80, 689-692).

An "increased cuticular wax load" refers to an increase of the amount of total extractable cuticular lipids per surface area compared to that of control tissue samples. The total cuticular wax load of the transformant shows an average fold increase of at least 4×, 5×, 6×, 7× (or more) over the control. An increase in cuticular wax load can be determined e.g. by Scanning Electron Microscopy (SEM) or by extraction and chemical analysis as known in the art and as described in the Examples.

An "altered wax composition" refers herein to a change in the relative amounts (i.e. a qualitative change) of the individual components making up the wax layer. Especially the relative amounts of alkanes, secondary alcohols and ketones are increased at least 5, 6, 7, 8, 9, 10, 11 fold or more in the transformants.

A "reduced number of trichomes" and/or "altered trichome structure" refers to a significant reduction (by at least 20%, 30%, 40%, 50% or more) of trichome numbers and/or a change in trichome structure (in particular branching) in transformants compared to wild type epidermal surfaces and is also indicative of an alteration in epidermal cell differentiation.

These phenotypes can be utilized in creating transgenic plants or plant tissues/organs with modified and improved agronomical characteristics, such as enhanced drought tolerance and/or enhanced salinity tolerance and others as described elsewhere herein.

Other putative members of the SHINE clade can be identified in silico, e.g. by identifying nucleic acid or protein sequences in existing nucleic acid or protein database (e.g. GENBANK, SWISSPROT, TrEMBL) and using standard sequence analysis software, such as sequence similarity search tools (BLASTN, BLASTP, BLASTX, TBLAST, FASTA, etc.). Especially the screening of plant sequence databases, such as the rice genome database, the wheat genome database, etc. for the presence of amino acid sequences or nucleic acid sequences encoding the consensus "mm" domain or a sequence essentially similar to the "mm" domain is desired. Putative amino acid sequences or nucleic acid sequences comprising or encoding at least one "mm" domain are selected, cloned or synthesized de novo and tested for in vivo functionality by e.g. overexpression in a plant host.

In accordance with the invention "SHN1", "SHN2", "SHN3" and "OsSHN1" and "OsSHN2" refers to any protein comprising the smallest biologically active fragment of SEQ ID NO's 11, 12, 13, 14, and 24 respectively, which retains a function in the formation of plant protective layers and/or cell separation layers. This includes hybrid and chimeric proteins comprising the smallest active fragment. Preferably, at least one "mm" consensus domain is present. More preferably additionally at least one consensus "cm" domain is present. Also included in this definition are variants of SHN1, SHN2, SHN3 and OsSHN1 and OsSHN2, such as amino acid sequences essentially similar to SEQ ID NO's 11, 12, 13, 14 or 24 respectively, having a sequence identity of at least 50%, 55%, 60%, 65%, 70%, 75%, 80%, 85%, 90%, 97%, 99%, 99.6%, 99.8% or more at the amino acid sequence level, as determined using pairwise alignment using the GAP program (with a gap creation penalty of 8 and an extension penalty of 2). Preferably proteins having some, preferably 5-10, particularly less than 5, amino acids added, replaced or deleted without significantly changing the protein activity are included in this definition. For example conservative amino acid substitutions within the categories basic (e.g. Arg, His, Lys), acidic (e.g. Asp, Glu), nonpolar (e.g. Ala, Val, Trp, Leu, Ile, Pro, Met, Phe, Trp) or polar (e.g. Gly, Ser, Thr, Tyr, Cys, Asn, Gln) fall within the scope of the invention as long as the activity of the SHN protein is not significantly, preferably not, changed, at least not changed in a negative way. In addition non-conservative amino acid substitutions fall within the scope of the invention as long as the activity of the SHN protein is not changed significantly, preferably not, or at least is not changed in a negative way.

The SHN proteins according to the invention may be isolated from natural sources, synthesized de novo by chemical synthesis (using e.g. a peptide synthesizer such as supplied by Applied Biosystems) or produced by recombinant host cells. The SHN proteins according to the invention may be used to raise mono- or polyclonal antibodies, which may for example be used for the detection of SHN proteins in samples (immunochemical analysis methods and kits).

Chimeric or hybrid SHN proteins comprise at least one "mm" domain, but may further comprise a "cm" domain and/or an AP2 domain or other domains from other proteins. Domains may thus be exchanged (domain swapping) between SHN proteins or between SHN proteins and other, unrelated proteins, as long as the functionality of the resulting chimeric protein essentially similar to that of SHN1, SHN2, SHN3 or OsSHN1 or OsSHN2. A chimeric SHN protein may thus, for example, comprise an AP2 domain from SHN1, an "mm" domain from SHN2 and a "cm" domain from OsSHN1. Similarly, a chimeric SHN protein may comprise at least one "mm" domain in addition to one or more protein domains not normally found in SHN proteins, such as stabilizing domains, binding domains (e.g. hormone binding domains, such as found in the glucocorticoid receptor, resulting in inducibility), etc. In another embodiment chimeric SHN proteins are provided which comprise a SHN-repressor domain fusion, such as the SHN-EAR fusion described below. In transgenic plants, overexpression of these chimeric proteins result in a dominant negative phenotype, as described further below. SHN-repressor domain fusion may also comprise additional domains fused thereto, such as e.g. a hormone binding domain (see e.g. Markel et al. 2002, Nucl. Acid Res. 30, 4709-4719).

The function of specific domains, such as the "mm" or "cm" domain, can be analyzed by deleting all or part of the domain(s) in a SHN protein or the introduction of mutations into the domain, and analysis of the resulting effect on the function of the SHN protein.

Also provided are nucleic acid sequences (genomic DNA, cDNA, RNA) encoding SHN clade proteins, such as for example SHN1, SHN2, SHN3, OsSHN1 and OsSHN2 as defined above (including any chimeric or hybrid SHN proteins), or any SHN protein from another species. In addition, the nucleic acid sequences encoding "mm" domains or "cm" domains are provided. Due to the degeneracy of the genetic code various nucleic acid sequences may encode the same amino acid sequence. Any nucleic acid sequence encoding SHN1, SHN2, SHN3 or OsSHN1 or OsSHN2 is herein referred to as "SHN1", "SHN2", "SHN3", and "OsSHN1" and "OsSHN2". The nucleic acid sequences provided include naturally occurring, artificial or synthetic nucleic acid sequences. Examples of nucleic acid sequences encoding SHN1-SHN3 and OsSHN1 are provided for in SEQ ID NO: 1, 2 and 3 (genomic SHN1, SHN2 and SHN3 sequences from *Arabidopsis*, respectively), SEQ ID NO: 4, 5 and 6 (RNA transcripts of SHN1, SHN2 and SHN3 from *Arabidopsis*, respectively) and SEQ ID NO: 7, 8, 9, 10 and 23 (cDNA of SHN1, SHN2, SHN3, OsSHN1 and OsSHN2, respectively). It is understood that when sequences are depicted in as DNA sequences while RNA is referred to, the actual base sequence of the RNA molecule is identical with the difference that thymine (T) is replace by uracil (U).

Also included are variants and fragments of SHN nucleic acid sequences, such as nucleic acid sequences hybridizing to SHN nucleic acid sequences, e.g. to SHN1, SHN2, SHN3 and/or OsSH1 and/or OsSHN2, under stringent hybridization conditions as defined. Variants of SHN nucleic acid sequences also include nucleic acid sequences which have a sequence identity to SEQ ID NO: 7, 8, 9 or 10 or 23 of at least 50% or more, preferably at least 55%, 60%, 70%, 80%, 90%, 95%, 99%, 99.5%, 99.8% or more. It is clear that many methods can be used to identify, synthesise or isolate variants or fragments of SHN nucleic acid sequences, such as nucleic acid hybridization, PCR technology, in silico analysis and nucleic acid synthesis, and the like.

The nucleic acid sequence, particularly DNA sequence, encoding the SHN proteins of this invention can be inserted in expression vectors to produce high amounts of SHN proteins (or e.g. chimeric SHN proteins), as described below. For optimal expression in a host the SHN DNA sequences can be codon-optimized by adapting the codon usage to that most preferred in plant genes, particularly to-genes native to the plant genus or species of interest (Bennetzen & Hall, 1982, J. Biol. Chem. 257, 3026-3031; Itakura et al., 1977 Science 198, 1056-1063.) using available codon usage tables (e.g. more adapted towards expression in cotton, soybean corn or rice). Codon usage tables for various plant species are published for example by Ikemura (1993, In "Plant Molecular Biology Labfax", Croy, ed., Bios Scientific Publishers Ltd.) and Nakamura et al. (2000, Nucl. Acids Res. 28, 292.) and in the major DNA sequence databases (e.g. EMBL at Heidelberg, Germany). Accordingly, synthetic DNA sequences can be constructed so that the same or substantially the same proteins are produced. Several techniques for modifying the codon usage to that preferred by the host cells can be found in patent and scientific literature. The exact method of codon usage modification is not critical for this invention.

Small modifications to a DNA sequence such as described above can be routinely made, i.e., by PCR-mediated mutagenesis (Ho et al., 1989, Gene 77, 51-59, White et al., 1989, Trends in Genet. 5, 185-189). More profound modifications to a DNA sequence can be routinely done by de novo DNA synthesis of a desired coding region using available techniques.

Also, the SHN nucleic acid sequences can be modified so that the N-terminus of the SHN protein has an optimum translation initiation context, by adding or deleting one or more amino acids at the N-terminal end of the protein. Often it is preferred that the proteins of the invention to be expressed in plants cells start with a Met-Asp or Met-Ala dipeptide for optimal translation initiation. An Asp or Ala codon may thus be inserted following the existing Met, or the second codon, Val, can be replaced by a codon for Asp (GAT or GAC) or Ala (GCT, GCC, GCA or GCG). The DNA sequences may also be modified to remove illegitimate splice sites.

In one embodiment of the invention SHN gene expression is downregulated in a host cell, plant or specific tissue(s), by e.g. RNAi approaches, as described elsewhere. In yet another embodiment SHN loss-of-function phenotypes (of host cells, tissues or whole plants) are generated by expressing a nucleic acid sequence encoding a protein fusion of a SHN protein (as defined) with a (dominant) repressor domain "Loss-of-function" refers herein to the loss of SHN protein function in a host tissue or organisms, and encompasses the function at the molecular level (e.g. loss of transcriptional activation of downstream target genes of the SHN transcription factor) and preferably also at the phenotypic level (e.g. podshatter resistance or male sterility). For example, in order to provide loss-of-function, SHN protein fusions are made with a 12 amino acid 'EAR' repressor domain as described by Hiratsu et al., 2003 (Plant J. 34:733-739), incorporated herein by reference. These repressor domain fusions to any one of the SHN proteins (as defined), termed herein 'SHN-EAR' fusion proteins, are able to cause repression of the downstream target genes and thus result in an effective loss-of-function mutant (dominant negative effect). These repressor fusions also effect repression in heterologous plants where the orthologous genes have not yet been identified. In one embodiment a nucleic acid sequence is provided which encodes a chimeric repressor domain-SHN protein fusion protein, especially a SHN-EAR fusion protein. In addition a vector comprising said nucleic acid sequence and a host cell, tissue and/or organism comprising the chimeric gene is provided. To generate a SHN-repressor domain fusion protein, the nucleic acid sequence encoding the repressor domain is translationally fused to the nucleic acid sequence comprising the SHN coding sequence. The SHN-repressor domain fusion protein encoding nucleic acid sequence (especially SHN-EAR) is placed under control of constitutive or specific promoters (e.g. tissue specific or developmentally regulated). Constitutive expression provides a loss-of-function in all host tissues where SHN1, SHN2 and SHN3 or including the orthologs e.g. OsSHN1 or OsSHN2, are expressed and required for function. Specific expression of the SHN-EAR protein provides a loss-of-function in the specific tissue or condition, e.g. when a dehiscence zone specific promoter is operably linked to a nucleic acid encoding a SHN-EAR fusion protein, e.g. the SHN2 promoter, loss of SHN function in the dehiscent zones of anther and silique results.

To generate a SHN-EAR fusion protein, the following 12 specific amino acids are added in frame to the C-terminal of a SHN protein: LDLDLELRLGFA (SEQ ID NO: 21). To generate a SHN-EAR fusion protein, the EAR domain encoding nucleic acid sequences, such as SEQ ID NO: 22, may be added in frame to the 3' end of the SHN coding sequence, followed by a stop codon (e.g. TAA).

```
(EAR repressor coding sequence):
                                       SEQ ID NO: 22
5'-CTG GAT CTG GAT CTA GAA CTC CGT TTG GGT TTC GCT
(TAA)-3'
```

It is understood that SHN proteins may be operably fused to other repression domain available in the art which function in plant cells. These include repressor domains of animal proteins, such as the *Drosophila* ENGRAILED (En) repressor domain. For example the N-terminal 298 amino acids may be fused to a SHN protein according to the invention, creating a dominant-negative chimeric protein (see Markel et al. 2002, Nucleic Acid Research Vol 30, 47094719 and Chandler and Werr 2003, Trends in Plant Science Vol. 8, 279-285, both incorporated by reference). It is noted that repressor domains may be fused to the SHN protein at the C-terminus or at the N-terminus, depending on the domain. The nucleic acid sequence encoding the dominant-negative fusion protein may be referred to as a "dominant-negative chimeric gene" and when transferred into a host genome as a "dominant-negative transgene" (either stably integrated in the host genome or transiently expressed). Other plant repressor domains are for example the LEUNG and SEUSS co-repressors of AGAMOUS, PLC and polycomb proteins. Other animal repressor domains include for example the WT1, eve, c-ErbA and v-ErbA and Krüppel associated box (see Chandler and Werr, 2003, supra and references therein).

In another embodiment of the invention PCR primers and/or probes and kits for detecting the SHN DNA sequences are provided. Degenerate or specific PCR primer pairs to amplify SHN DNA from samples can be synthesized based on SEQ ID NO's 1-10 as known in the art (see Dieffenbach and Dveksler (1995) PCR Primer: A Laboratory Manual, Cold Spring Harbor Laboratory Press, and McPherson at al. (2000) PCR-Basics: From Background to Bench, First Edition, Springer Verlag, Germany). Likewise, DNA fragments of SEQ ID NO's 1-10 can be used as hybridization probes. An SHN detection kit may comprise either SHN specific primers and/or SHN specific probes, and an associated protocol to use the primers or probe to detect SHN DNA in a sample. Such a detection kit may, for example, be used to determine, whether a plant has been transformed with an SHN gene (or part thereof) of the invention. Because of the degeneracy of the genetic code, some amino acid codons can be replaced by others without changing the amino acid sequence of the protein.

In another embodiment antibodies that bind specifically to a SHN protein according to the invention are provided. In particular monoclonal or polyclonal antibodies that bind to SHN1, SHN2, SHN3 or OsSHN1 or OsSHN2, or to fragments or variants thereof, are encompassed herein. An antibody can be prepared by using a SHN protein according to the invention as an antigen in an animal using methods known in the art, as e.g. described in Harlow and Lane "Using Antibodies: A laboratory manual" (New York: Cold Spring Harbor Press 1998) and in Liddell and Cryer "A Practical Guide to Monoclonal Antibodies" (Wiley and Sons, 1991). The antibodies can subsequently be used to isolate, identify, characterize or purify the SHN protein to which it binds, for example to detect the SHN protein in a sample, allowing the formation of an immunocomplex and detecting the presence of the immunocomplex by e.g. ELISA (enzyme linked immunoassay) or immunoblot analysis. Also provided are immunological kits, useful for detecting the SHN proteins, protein fragments or epitopes in a sample provided. Samples may be cells, cell supernatants, cell suspensions, tissues, etc. Such a kit comprises at least an antibody that binds to a SHN protein and one or more immunodetection reagents. The antibodies can also be used to isolate/identify other SHN proteins, for example by ELISA or Western blotting.

In addition, nucleic acid sequences comprising SHN1, SHN2, SHN3 and OsSHN1 promoters are provided herein. The transcription regulatory sequences are found in the about 2 kb sequence upstream of the ATG codon of SEQ ID NO: 1, 2 and 3. The transcription regulatory sequences of SHN1, SHN2 and SHN3 are provided herein in SEQ ID NO: 17, 18 and 19, respectively, and the transcription regulatory sequence of OsSHN1 is provided as SEQ ID NO: 20. These transcription regulatory sequences may be used for the construction of chimeric genes and for expressing operably linked nucleic acid sequences in hosts or host cells. Especially the SHN1 transcription regulatory sequence may be used for expression in inflorescence tissues, root tissue and abscission zone of siliques. The SHN2 transcription regulatory sequence may be used to direct expression in dehiscence zones of anthers and siliques and may thus be useful for generating male sterility or podshatter resistance. The transcription regulatory region of SHN3 is active in many tissues and may thus be used for directing broader expression in essentially all organs and tissues (see Examples). It is understood that the tissue specificity of the transcription regulatory sequences can be improved or specified by analysing deletion fragments of the sequences provided for their ability to direct expression of nucleic acid sequences operably linked thereto. Such deletion analysis allows the removal of nucleic acid parts which cause non-specific (background) expression. Similarly, the transcription regulatory sequences of other SHN genes can be isolated by sequencing the genomic DNA upstream of the ATG codon, using known methods such as TAIL-PCR.

Chimeric Genes Vectors and Recombinant Microorganisms According to the Invention In one embodiment of the invention nucleic acid sequences encoding SHN proteins (including e.g. fusion proteins such as SHN-EAR), as described above, are used to make chimeric genes, and vectors comprising these for transfer of the chimeric gene into a host cell and production of the SHN protein(s) in host cells, such as cells, tissues, organs or organisms derived from transformed cell(s). Host cells are preferably plant cells and, but microbial hosts (bacteria, yeast, fungi, etc.) are also envisaged. Any crop plant may be a suitable host, such as monocotyledonous plants or dicotyledonous plants, for example maize/corn (Zea species, e.g. Z. mays, Z. diploperennis (chapule), Zea luxurians (Guatemalan teosinte), Zea mays subsp. huehuetenangensis (San Antonio Huista teosinte), Z. mays subsp. mexicana (Mexican teosinte), Z. mays subsp. parviglumis (Balsas teosinte), Z. perennis (perennial teosinte) and Z. ramosa), wheat (Triticum species), barley (e.g. Hordeum vulgare), oat (e.g. Avena sativa), sorghum (Sorghum bicolor), rye (Secale cereale), soybean (Glycine spp, e.g. G. max), cotton (Gossypium species, e.g. G. hirsutum, G. barbadense), Brassica spp. (e.g. B. napus, B. juncea, B. oleracea, B. rapa, etc), sunflower (Helianthus annus), tobacco (Nicotiana species), alfalfa (Medicago sativa), rice (Oryza species, e.g. O. sativa indica cultivar-group or japonica cultivar-group), forage grasses, pearl millet (Pennisetum spp. e.g. P. glaucum), tree species, vegetable species, such as Lycopersicon ssp (e.g. Lycopersicon esculentum), potato (Solanum tuberosum, other Solanum species), eggplant (Solanum melongena), peppers (Capsicum annuum, Capsicum frutescens), pea, bean (e.g. Phaseolus species), fleshy fruit (grapes, peaches, plums, strawberry, mango) ornamental species (e.g. Rose, Petunia, Chrysanthemum, Lily, Gerbera species), woody trees (e.g. species of Populus, Salix, Quercus, Eucalyptus), fibre species e.g. flax (Linum usitatissimum) and hemp (Cannabis sativa). In one embodiment monocotyledonous crop plants are preferred.

A "crop plant" refers herein to a plant species which is cultivated and bred by humans and excludes weeds such as Arabidopsis thaliana. A crop plant may be cultivated for food purposes (e.g. field crops), or for ornamental purposes (e.g. production of flowers for cutting, grasses for lawns, etc.). A crop plant as defined herein also includes plants from which non-food products are harvested, such as oil for fuel, plastic polymers, pharmaceutical products, cork and the like.

The construction of chimeric genes and vectors for, preferably stable, introduction of SHN protein encoding nucleic acid sequences into the genome of host cells is generally known in the art. To generate a chimeric gene the nucleic acid sequence encoding a SHN protein (or e.g. a SHN-repressor domain fusion protein) is operably linked to a promoter sequence, suitable for expression in the host cells, using standard molecular biology techniques. The promoter sequence may already be present in a vector so that the SHN nucleic sequence is simply inserted into the vector downstream of the promoter sequence. The vector is then used to transform the host cells and the chimeric gene is inserted in the nuclear genome or into the plastid, mitochondrial or chloroplast genome and expressed there using a suitable promoter (e.g., Mc Bride et al., 1995 Bio/Technology 13, 362; U.S. Pat. No. 5,693,507). In one embodiment a chimeric gene comprises a suitable promoter for expression in plant cells or microbial cells (e.g. bacteria), operably linked thereto a nucleic acid sequence encoding a SHN protein or fusion protein according to the invention, optionally followed by a 3'nontranslated nucleic acid sequence.

The SHN nucleic acid sequence, preferably the SHN chimeric gene, encoding an functional SHN protein (or in certain embodiments a functional SHN-repressor domain fusion protein), can be stably inserted in a conventional manner into the nuclear genome of a single plant cell, and the so-transformed plant cell can be used in a conventional manner to produce a transformed plant that has an altered phenotype due to the presence of the SHN protein in certain cells at a certain time. In this regard, a T-DNA vector, comprising a nucleic acid sequence encoding a SHN protein, in *Agrobacterium tumefaciens* can be used to transform the plant cell, and thereafter, a transformed plant can be regenerated from the transformed plant cell using the procedures described, for example, in EP 0 116 718, EP 0 270 822, PCT publication WO84/02913 and published European Patent application EP 0 242 246 and in Gould et al. (1991, Plant Physiol. 95, 426-434). The construction of a T-DNA vector for *Agrobacterium* mediated plant transformation is well known in the art. The T-DNA vector may be either a binary vector as described in EP 0 120 561 and EP 0 120 515 or a co-integrate vector which can integrate into the *Agrobacterium* Ti-plasmid by homologous recombination, as described in EP 0 116 718.

Preferred T-DNA vectors each contain a promoter operably linked to SHN encoding nucleic acid sequence between T-DNA border sequences, or at least located to the left of the right border sequence. Border sequences are described in Gielen et al. (1984, EMBO J 3, 835-845). Of course, other types of vectors can be used to transform the plant cell, using procedures such as direct gene transfer (as described, for example in EP 0 223 247), pollen mediated transformation (as described, for example in EP 0 270 356 and WO85/01856), protoplast transformation as, for example, described in U.S. Pat. No. 4,684,611, plant RNA virus-mediated transformation (as described, for example in EP 0 067 553 and U.S. Pat. No. 4,407,956), liposome-mediated transformation (as described, for example in U.S. Pat. No. 4,536,475), and other methods such as those described methods for transforming certain lines of corn (e.g., U.S. Pat. No. 6,140,553; Fromm et al., 1990, Bio/Technology 8, 833-839; Gordon-Kamm et al., 1990, The Plant Cell 2, 603-618) and rice (Shimamoto et al., 1989, Nature 338, 274-276; Datta et al 1990, Bio/Technology 8, 736-740) and the method for transforming monocots generally (PCT publication WO92/09696). For cotton transformation see also WO 00/71733, and for rice transformation see also the methods described in WO92/09696, WO94/00977 and WO95/06722. For sorghum transformation see e.g. Jeoung J M et al. 2002, Hereditas 137: 20-8 or Zhao Z Y et al. 2000, Plant Mol. Biol. 44:789-98). Likewise, selection and regeneration of transformed plants from transformed cells is well known in the art. Obviously, for different species and even for different varieties or cultivars of a single species, protocols are specifically adapted for regenerating transformants at high frequency.

Besides transformation of the nuclear genome, also transformation of the plastid genome, preferably chloroplast genome, is included in the invention. One advantage of plastid genome transformation is that the risk of spread of the transgene(s) can be reduced. Plastid genome transformation can be carried out as known in the art, see e.g. Sidorov V A et al. 1999, Plant J. 19: 209-216 or Lutz K A et al. 2004, Plant J. 37(6):906-13.

The resulting transformed plant can be used in a conventional plant breeding scheme to produce more transformed plants with the same characteristics or to introduce the gene part into other varieties of the same or related plant species. Seeds, which are obtained from the transformed plants, contain the chimeric SHN gene as a stable genomic insert. Cells of the transformed plant can be cultured in a conventional manner to produce the SHN protein, which can be recovered for other use e.g. antibody production.

The SHN nucleic acid sequence is inserted in a plant cell genome so that the inserted coding sequence is downstream (i.e. 3') of, and under the control of, a promoter which can direct the expression in the plant cell. This is preferably accomplished by inserting the chimeric gene in the plant cell genome, particularly in the nuclear or plastid (e.g. chloroplast) genome.

Preferred promoters include: the strong constitutive 35S promoters or enhanced 35S promoters (the "35S promoters") of the cauliflower mosaic virus (CaMV) of isolates CM 1841 (Gardner et al., 1981, Nucleic Acids Research 9, 2871-2887), CabbB-S (Franck et al., 1980, Cell 21, 285-294) and CabbB-JI (Hull and Howell, 1987, Virology 86, 482-493); the 35S promoter described by Odell et al. (1985, Nature 313, 810-812) or in U.S. Pat. No. 5,164,316, promoters from the ubiquitin family (e.g. the maize ubiquitin promoter of Christensen et al., 1992, Plant Mol. Biol. 18, 675-689, EP 0 342 926, see also Cornejo et al. 1993, Plant Mol. Biol. 23, 567-581), the gos2 promoter (de Pater et al., 1992 Plant J. 2, 834-844), the emu promoter (Last et al., 1990, Theor. Appl. Genet. 81, 581-588), *Arabidopsis* actin promoters such as the promoter described by An et al. (1996, Plant J. 10, 107.), rice actin promoters such as the promoter described by Zhang et al. (1991, The Plant Cell 3, 1155-1165) and the promoter described in U.S. Pat. No. 5,641,876 or the rice actin 2 promoter as described in WO070067; promoters of the Cassava vein mosaic virus (WO 97/48819, Verdaguer et al. 1998, Plant Mol. Biol. 37, 1055-1067), the pPLEX series of promoters from Subterranean Clover Stunt Virus (WO 96/06932, particularly the S7 promoter), a alcohol dehydrogenase promoter, e.g., pAdh1S (GenBank accession numbers X04049, X00581), and the TR1' promoter and the TR2' promoter (the "TR1'promoter" and "TR2'promoter", respectively) which drive the expression of the 1' and 2' genes, respectively, of the T-DNA (Velten et al., 1984, EMBO J 3, 2723-2730), the Figwort Mosaic Virus promoter described in U.S. Pat. No. 6,051,753 and in EP426641, histone gene promoters, such as the Ph4a748 promoter from *Arabidopsis* (PMB 8: 179-191), or others.

Alternatively, a promoter can be utilized which is not constitutive but rather is specific for one or more tissues or organs of the plant (tissue preferred/tissue specific, including developmentally regulated promoters), for example leaf preferred, epidermis preferred, root preferred, flower tissue e.g. tapetum or anther preferred, seed preferred, pod preferred, etc.), whereby the SHN gene (inlcuding e.g. the SHN-repressor fusion protein encoding gene) is expressed only in cells of the specific tissue(s) or organ(s) and/or only during a certain developmental stage. For example, the SHN gene(s) can be selectively expressed in the leaves of a plant by placing the coding sequence under the control of a light-inducible promoter such as the promoter of the ribulose-1,5-bisphosphate carboxylase small subunit gene of the plant itself or of another plant, such as pea, as disclosed in U.S. Pat. No. 5,254,799 or *Arabidopsis* as disclosed in U.S. Pat. No. 5,034,322. The choice of the promoter is determined by the phenotype one aims to achieve, as will be described in more detail below. For example, to achieve fruits (e.g. tomatoes) with an increased water loss and therefore a more solid fruit flesh and enhanced taste, a fruit specific or fruit preferred promoter is the most suitable.

To achieve drought tolerance a constitutive, a leaf specific, epidermis specific or light-inducible promoter would be suitable. Suitable epidermal specific promoters, such as for example the *Arabidopsis* LTP1 promoter (Thoma et al, 1994, Plant Physiol. 105(1):35-45.), the CER1 promoter (Aarts et al 1995. Plant Cell. 7:2115-27), and the CER6 promoter (Hooker et al 2002, Plant Physiol 129:1568-80.) and the orthologous tomato LeCER6 (Vogg et al, 2004, J. Exp Bot. 55: 1401-10), provide specific expression in above ground epidermal surfaces.

To achieve male sterility an anther/anther tissue or anther development specific promoter such as e.g. the SHN2 promoter provided herein, the tapetum specific promoters TA13 and TA29 from tobacco (U.S. Pat. No. 6,562,354; Koltunow et al. 1990, Plant Cell 2:1201-1224; Seurinck et al. 1990 Nucleic Acids Res. 18: 3403), the tapetum specific promoter CA55 from *Zea mays* (EP570422), tapetum specific MS2 promoter from *Arabidopsis* (Aarts et al 1997, Plant J. 12:615-23), anther specific TAA promoters from wheat (Wang et al., 2002, Plant J. 30: 613-623), tapetum specific promoter from rice (e.g. PE1, T42, T72 from rice), a microspore development specific promoter such as NTM19 from tobacco (EP790311) or a male germline specific promoter (e.g. LGC1 from lily, WO9905281) or others may be used.

For certain phenotypes such as potatoes (i.e. tubers) with enhanced wound healing and/or peel quality a tuber or peel specific promoter is the most suitable such as the class II patatin promoter (Nap et al, 1992, Plant Mol Biol. 20: 683-94.) that specifies expression in the outer layer of the tuber, or a promoter with leaf and tuber peel expression such as the potato UBI7 promoter (Garbarino et al., 1995, Plant Physiol., 109: 1371-8).

For phenotypes in root tissue a promoter preferentially active in roots is described in WO00/29566. Another promoter for root preferential expression is the ZRP promoter (and modifications thereof) as described in U.S. Pat. No. 5,633,363.

To confer expression to fruits, a tomato fruit and peel specific promoter e.g. beta-Galactosidase II (Smith et al., 1998, Plant Physiol 117: 417-23) or tomato Epicuticular wax promoter LeCER6 (Vogg et al, 2004, supra) can be used to induce water loss from fruit peel through the cuticle. A fruit skin or epidermal promoter can be identified and isolated by one skilled in the art, using microarrays and confirmation by transformation of promoter reporter gene fusions.

Another alternative is to use a promoter whose expression is inducible. Examples of inducible promoters are wound-inducible promoters, such as the MPI promoter described by Cordera et al. (1994, The Plant Journal 6, 141), which is induced by wounding (such as caused by insect or physical wounding), or the COMPTII promoter (WO0056897) or the promoter described in U.S. Pat. No. 6,031,151. Alternatively the promoter may be inducible by a chemical, such as dexamethasone as described by Aoyama and Chua (1997, Plant Journal 11: 605-612) and in U.S. Pat. No. 6,063,985 or by tetracycline (TOPFREE or TOP 10 promoter, see Gatz, 1997, Annu Rev Plant Physiol Plant Mol. Biol. 48: 89-108 and Love et al. 2000, Plant J. 21: 579-88). Other inducible promoters are for example inducible by a change in temperature, such as the heat shock promoter described in U.S. Pat. No. 5,447,858, by anaerobic conditions (e.g. the maize ADH1S promoter), by light (U.S. Pat. No. 6,455,760), by pathogens (e.g. EP759085 or EP309862) or by senescence (SAG12 and SAG13, see U.S. Pat. No. 5,689,042). Obviously, there are a range of other promoters available. A podwall specific promoter from *Arabidopsis* is the FUL promoter (also referred to as AGL8 promoter, WO9900502; WO9900503; Liljegren et al. 2004 Cell. 116(6):843-53)), the *Arabidopsis* IND1 promoter (Lijegren et al. 2004, supra; WO9900502; WO9900503) or the dehiscence zone specific promoter of a *Brassica* polygalacturonase gene (WO9713856). A petal specific promoter has been described in WO9915679. Seed specific promoters are described in EP723019, EP255378 or WO9845461.

The SHN coding sequence (or a chimeric SHN protein encoding sequence) is inserted into the plant genome so that the coding sequence is upstream (i.e. 5') of suitable 3'end transcription regulation signals ("3'end") (i.e. transcript formation and polyadenylation signals). Polyadenylation and transcript formation signals include those of the CaMV 35S gene ("3' 35S"), the nopaline synthase gene ("3'nos") (Depicker et al., 1982 J. Molec. Appl. Genetics 1, 561-573.), the octopine synthase gene ("3'ocs") (Gielen et al., 1984, EMBO J 3, 835-845) and the T-DNA gene 7 ("3' gene 7") (Velten and Schell, 1985, Nucleic Acids Research 13, 6981-6998), which act as 3'-untranslated DNA sequences in transformed plant cells, and others.

Introduction of the T-DNA vector into *Agrobacterium* can be carried out using known methods, such as electroporation or triparental mating.

A SHN encoding nucleic acid sequence can optionally be inserted in the plant genome as a hybrid gene sequence whereby the SHN sequence is linked in-frame to a (U.S. Pat. No. 5,254,799; Vaeck et al., 1987, Nature 328, 33-37) gene encoding a selectable or scorable marker, such as for example the neo (or nptII) gene (EP 0 242 236) encoding kanamycin resistance, so that the plant expresses a fusion protein which is easily detectable.

Transformation of plant cells can also be used to produce the SHN protein(s) of the invention in large amounts in plant cell cultures to induce activated precursors of suberin, cutin and wax biosynthesis that might be channelled for cross-linking into bio-polymers. When reference to a transgenic plant cell is made herein, this refers to a plant cell (or also a plant protoplast) as such in isolation or in tissue culture, or to a plant cell (or protoplast) contained in a plant or in a differentiated organ or tissue, and both possibilities are specifically included herein. Hence, a reference to a plant cell in the description or claims is not meant to refer only to isolated cells in culture, but refers to any plant cell, wherever it may be located or in whatever type of plant tissue or organ it may be present.

All or part a SHN nucleic acid sequence, encoding a SHN protein (or a chimeric SHN protein), can also be used to transform microorganisms, such as bacteria (e.g. *Escherichia coli, Pseudomonas, Agrobacterium, Bacillus*, etc.), fungi, viruses, algae or insects. Transformation of bacteria, with all or part of a SHN nucleic acid sequence of this invention, incorporated in a suitable cloning vehicle, can be carried out in a conventional manner, preferably using conventional electroporation techniques as described in Maillon et al. (1989, FEMS Microbiol. Letters 60, 205-210.) and WO 90/06999. For expression in prokaryotic host cell, the codon usage of the nucleic acid sequence may be optimized accordingly (as described for plants above). Intron sequences should be removed and other adaptations for optimal expression may be made as known.

For obtaining enhanced expression in monocot plants such as grass species, e.g. corn or rice, an intron, preferably a monocot intron, can be added to the chimeric gene. For example the insertion of the intron of the maize Adh1 gene into the 5' regulatory region has been shown to enhance expression in maize (Callis et. al., 1987, Genes Develop. 1: 1183-1200). Likewise, the HSP70 intron, as described in U.S.

Pat. No. 5,859,347, may be used to enhance expression. The DNA sequence of the SHN nucleic acid sequence can be further changed in a translationally neutral manner, to modify possibly inhibiting DNA sequences present in the gene part by means of site-directed intron insertion and/or by introducing changes to the codon usage, e.g., adapting the codon usage to that most preferred by plants, preferably the specific relevant plant genus, as described above.

In accordance with one embodiment of this invention, the SHN proteins (or chimeric proteins) are targeted to intracellular organelles such as plastids, preferably chloroplasts, mitochondria, or are secreted from the cell, potentially optimizing protein stability and/or expression. Similarly, the protein may be targeted to vacuoles. For this purpose, in one embodiment of this invention, the chimeric genes of the invention comprise a coding region encoding a signal or target peptide, linked to the SHN protein coding region of the invention. Particularly preferred peptides to be included in the proteins of this invention are the transit peptides for chloroplast or other plastid targeting, especially duplicated transit peptide regions from plant genes whose gene product is targeted to the plastids, the optimized transit peptide of Capellades et al. (U.S. Pat. No. 5,635,618), the transit peptide of ferredoxin-NADP+oxidoreductase from spinach (Oelmuller et al., 1993, Mol. Gen. Genet. 237, 261-272), the transit peptide described in Wong et al. (1992, Plant Molec. Biol. 20, 81-93) and the targeting peptides in published PCT patent application WO 00/26371. Also preferred are peptides signalling secretion of a protein linked to such peptide outside the cell, such as the secretion signal of the potato proteinase inhibitor11 (Keil et al., 1986, Nucl. Acids Res. 14, 5641-5650), the secretion signal of the alpha-amylase 3 gene of rice (Sutliff et al., 1991, Plant Molec. Biol. 16, 579-591) and the secretion signal of tobacco PR1 protein (Cornelissen et al., 1986, EMBO J. 5, 37-40). Particularly useful signal peptides in accordance with the invention include the chloroplast transit peptide (e.g. Van Den Broeck et al., 1985, Nature 313, 358), or the optimized chloroplast transit peptide of U.S. Pat. Nos. 5,510,471 and 5,635,618 causing transport of the protein to the chloroplasts, a secretory signal peptide or a peptide targeting the protein to other plastids, mitochondria, the ER, or another organelle. Signal sequences for targeting to intracellular organelles or for secretion outside the plant cell or to the cell wall are found in naturally targeted or secreted proteins, preferably those described by Klösgen et al. (1989, Mol. Gen. Genet. 217, 155-161), Klösgen and Weil (1991, Mol. Gen. Genet. 225, 297-304), Neuhaus & Rogers (1998, Plant Mol. Biol. 38, 127-144), Bih et al. (1999, J. Biol. Chem. 274, 22884-22894), Morris et al. (1999, Biochem. Biophys. Res. Commun. 255, 328-333), Hesse et al. (1989, EMBO J. 8, 2453-2461), Tavladoraki et al. (1998, FEBS Lett. 426, 62-66.), Terashima et al. (1999, Appl. Microbiol. Biotechnol. 52, 516-523), Park et al. (1997, J. Biol. Chem. 272, 6876-6881), Shcherban et al. (1995, Proc. Natl. Acad. Sci. USA 92, 9245-9249).

To allow secretion of the SHN proteins to the outside of the transformed host cell, an appropriate secretion signal peptide may be fused to the amino terminal end (N-terminal end) of the SHN protein. Putative signal peptides can be detected using computer based analysis, using programs such as the program Signal Peptide search (SignalP V1.1 or 2.0)(Von Heijne, Gunnar, 1986 and Nielsen et al., 1996).

In one embodiment, several SHN encoding nucleic acid sequences are co-expressed in a single host. A co-expressing host plant is easily obtained by transforming a plant already expressing SHN protein of this invention, or by crossing plants transformed with different SHN proteins of this invention. Alternatively, several SHN protein encoding nucleic acid sequences can be present on a single transformation vector or be co-transformed at the same time using separate vectors and selecting transformants comprising both chimeric genes. Similarly, one or more SHN encoding genes may be expressed in a single plant together with other chimeric genes, for example encoding other proteins which enhance drought tolerance, such as CBF1, DREB1A, the rice OsDREB genes (Dubouzet et al, 2003, Plant J. 33: 751) or others.

It is understood that the different proteins can be expressed in the same plant, or each can be expressed in a single plant and then combined in the same plant by crossing the single plants with one another. For example, in hybrid seed production, each parent plant can express a single protein. Upon crossing the parent plants to produce hybrids, both proteins are combined in the hybrid plant.

Preferably, for selection purposes but also for weed control options, the transgenic plants of the invention are also transformed with a DNA encoding a protein conferring resistance to herbicide, such as a broad-spectrum herbicide, for example herbicides based on glufosinate ammonium as active ingredient (e.g. Liberty® or BASTA; resistance is conferred by the PAT or bar gene; see EP 0 242 236 and EP 0 242 246) or glyphosate (e.g. RoundUp®; resistance is conferred by EPSPS genes, see e.g. EP0 508 909 and EP 0 507 698). Using herbicide resistance genes (or other genes conferring a desired phenotype) as selectable marker further has the advantage that the introduction of antibiotic resistance genes can be avoided.

Alternatively, other selectable marker genes may be used, such as antibiotic resistance genes. As it is generally not accepted to retain antibiotic resistance genes in the transformed host plants, these genes can be removed again following selection of the transformants. Different technologies exist for removal of transgenes. One method to achieve removal is by flanking the chimeric gene with lox sites and, following selection, crossing the transformed plant with a CRE recombinase-expressing plant (see e.g. EP506763B1). Site specific recombination results in excision of the marker gene. Another site specific recombination systems is the FLP/FRT system described in EP686191 and U.S. Pat. No. 5,527,695. Site specific recombination systems such as CRE/LOX and FLP/FRT may also be used for gene stacking purposes. Further, one-component excision systems have been described, see e.g. WO9737012 or WO9500555).

Transformed Plant Cells/Plants/Seeds and Uses of the Nucleic Acid Sequence and Proteins According to the Invention In the following part the use of the SHN sequences according to the invention to generate transgenic plant cells, plants, plant seeds and any derivatives/progeny thereof, with one or more modified phenotypes is described.

A) Plants with Enhanced Drought Tolerance

A transgenic, drought tolerant plant can be generated by transforming a plant host cell with a nucleic acid sequence encoding at least one SHN protein under the control of a suitable promoter, as described above, and regenerating a transgenic plant from said cell. Preferred promoters are promoters which are active specifically in above-ground parts of the plant, such as in the leaves, leaf epidermis or upon light induction or following application of chemical compounds. In particular the following promoters are preferred: leaf epidermal specific promoters such as the *Arabidopsis* LTP1 (Thoma et al, 1994, supra), the CER1 promoter (Aarts et al. 1995, supra), the CER6 promoter (Hooker et al 2002, supra) and the orthologous tomato LeCER6 promoter (Vogg et al, 2004, supra); leaf or photosynthetic tissue specific promoters, such as the light inducible ribulose 1,5-bisphosphate carboxylase small subunit promoter (Pssu) from *Arabidopsis* as described in U.S. Pat. No. 5,034,322 or from sunflower, from pea (U.S. Pat. No. 5,254,799) or from *Zea mays*; the potato ST-LS1 promoter which is stem and leaf specific (Stockhaus et al. 1987, Nucleic Acids Res. 15(8):3479-91); the promoter of the chlorophyll a/b binding protein (CAB).

As the promoter of the SHN3 gene is active in all plant organs analyzed, the SHN3 promoter (SEQ ID NO: 19) according to the invention, or the smallest active fragment thereof, may also be used.

"Drought tolerance" or "increased/enhanced drought tolerance" is used herein to refer to an enhanced ability of transformants (compared to wild type or control transformants) to tolerate a period of drought (water deprivation/depletion leading to e.g. visible leaf wilting symptoms in control plants) and to recover subsequently, thereby leading to a reduced overall yield loss, as more plants per m² survive and/or the yield of the surviving plants is not significantly reduced. Drought tolerance can be assessed in controlled environments (green house or growth chambers) by placing at least about 10 transformants per transformation event and at least 10 control plants for various time periods (ranging from 1-4 weeks or more) into the environment without watering them, until leaf wilting or loss of turgor is caused on control plants, and subsequently watering the plants again for 1-2 weeks, while their recovery phenotype is analyzed. Transformants with drought tolerance survive at least 2, 3, 4, 5, 6, 7 days, preferably at least 2-5 days longer without water than control-transformants (e.g. transformed with an empty vector) or wild type plants do under the same conditions, and which show irreversible tissue damage. In another method of estimating tolerance the recovery of transformants is at least about 2-5 times higher than that of the control plants (e.g. with 20% control recovery, 40-100% survival in transformants).

Transformants expressing high levels of the SHN protein are selected by e.g. analysing copy number (Southern blot analysis), mRNA transcript levels (e.g. RT-PCR using SHN primer pairs or flanking primers) or by analysing the presence and level of SHN protein in various tissues (e.g. SDS-PAGE; ELISA assays, etc). For regulatory reasons, preferably single copy transformants are selected and the sequences flanking the site of insertion of the chimeric gene is analysed, preferably sequenced to characterize the "event". High SHN expressing transgenic events are selected for further crossing/backcrossing/selfing until a high performing elite event with a stable SHN transgene is obtained. Generally, SHN gene expression levels and SHN protein levels will correlate with the drought tolerance phenotype. In one embodiment especially the transgenic seeds derived from such plants are provided, which may be sold as being "drought tolerant".

Transformants expressing one or more SHN genes according to the invention may also comprise other transgenes, such as other genes conferring drought tolerance or conferring tolerance to other biotic or abiotic stresses. To obtain such plants with "stacked" transgenes, other transgenes may either be introgressed into the SHN transformants, or the SHN transformants may be transformed subsequently with one or more other genes, or alternatively several chimeric genes may be used to transform a plant line or variety. For example, several chimeric genes may be present on a single vector, or may be present on different vectors which are co-transformed.

In one embodiment the following genes are combined with one or more SHN genes according to the invention: Genes encoding other AP2/EREBP type transcription factors, preferably ones which have a role in the plant's response to environmental stresses, such as for example the CBF1, CBF2, CBF3 and/or CBF4 encoding genes from *Arabidopsis* (Jaglo-Ottosen et al 1998, Kasuga et al 1999, supra) or orthologs thereof from other species (Dubouzet et al 2003, supra), with insect resistance genes such as *Bacillus thuringiensis* toxin genes (encoding insecticidal proteins, such as cry genes, vip genes, etc. see http://www.biols.susx.ac.uk/home/ for a list of available genes), fungal resistance genes, or other genes.

The stacked transformants may thus have an even broader environmental stress tolerance, to for example salinity, cold stress, insect resistance, pathogen resistance, heat stress, water stress, etc.

It is also possible to introduce or introgress the SHN gene into a plant breeding line which already has a relatively high drought tolerance, whereby this tolerance may be due to a different underlying molecular mechanism (e.g. root architecture).

In a preferred embodiment the transformants are drought tolerant, but have an unmodified epicuticular wax layer and thus the leaves have unmodified appearance compared to wild type plants. In this embodiment monocotyledonous plants, such as rice and maize, are especially preferred.

In one embodiment, SEQ ID NO: 144 of WO03/013228 and/or the WIN1 gene described by Broun et al. (supra) are excluded herein.

B) Podshatter Resistant Plants

In another embodiment podshatter resistant plants are provided, which overexpress a SHN-repressor domain fusion protein according to the invention (e.g. a SHN1-EAR, SHN2-EAR, SHN3-EAR or OsSHN1-EAR fusion protein, or another SHN ortholog-EAR fusion) or which express a nucleic acid sequence which causes silencing of the endogenous SHN gene(s). "Podshatter resistance" refers herein to the plant's pods having an increased resistance to pod valve separation at maturity, resulting in a reduced seed loss during harvest. However, the increase in resistance to valve separation preferably does not result in an inability to separate the pod valves, which would make the harvesting of seeds very difficult or impossible. This "fine-tuning" of the ease/difficulty of separating the pod valves may be achieved by selecting a suitable promoter/coding sequence combination.

A number of tests exist which can be used to assess the podshatter resistance of a plant, such as the Random Impact Test (RIT) (see Summers et al. 2003, J. Agricultural Science 140, 43-52 and Bruce et al. 2002, Biosystems Engineering 81(2):179-184). The RIT involves collecting fully mature pods from plants and placing them for a number of days in a controlled environment (e.g. 3 days at 25C and 50% RH). Twenty undamaged pods are then placed together with six steel balls of 12.5 mm diameter in a 20 cm diameter cylindrical container. The container is mechanically shaken at a frequency of 4.98 Hz and a stroke length of 51 mm for two 10s periods, followed where required by one period each of 20, 40 and 80s. At the end of each period pods are examined and classed as shattered if at least one of the valves had detached. Statistical analysis is then used to calculate the time (s) taken for 50% of the pods to shatter ($RIT_{50}$ value). In such a test a shatter susceptible plant line will result in mean $RIT_{50}$ values of around 18 seconds with a narrow distribution around the mean. A shatter resistant plant can be defined by having an RIT50 value which is significantly larger than the $RIT_{50}$ value of the control (e.g. the wild type or control transformant), for example a mean $RIT_{50}$ of 1.5×, 2×, 3×, 4× (or more) the value of the control. Alternatively, seed loss in the field can be assessed, for example by placing trays underneath the plants and collecting the shattered seeds.

Podshatter resistant plants according to the invention may be generated by repressing the formation of the dehiscence zone by silencing the SHN gene or by expressing a SHN-repressor domain fusion protein, especially a SHN-EAR fusion protein (as described above). This can be achieved by transforming a plant cell with a chimeric construct comprising a pod- or fruit-specific promoter or a promoter which is preferentially active in a specific tissue of the pod or during a specific stage of pod-development, operably linked to either a SHN-repressor domain fusion protein (e.g. a SHN-EAR fusion protein) encoding nucleic acid sequence or a gene silencing SHN fragment (e.g. a sense and/or antisense SHN DNA fragment, see below) and suitably a 3' sequence. Suitable promoters are for example the SHN2 promoter (SEQ ID NO: 18) or an active fragment thereof, the promoter of the *Arabidopsis* or *Brassica napus* FRUITFUL gene (also referred to as AGL8) (see U.S. Pat. No. 6,198,024), the *Arabidopsis* or *Brassica* dehiscence zone specific regulatory elements of genes AGL1 or AGL5 (see U.S. Pat. No. 6,198,024), the promoter of the *Arabidopsis* INDEHISCENT1 gene (IND1; see WO017951) or of the *Brassica napus* homolog of IND1, or a dehiscence zone specific promoters such as the *Brassica* polygalacturonase promoter described in WO9713856, or derivatives thereof. Alternatively a constitutive promoter may be used.

As pod shattering and the associated yield loss is a problem in pod-bearing plants, mainly members of the Brassicaceae such as of *Brassica napus*, but also members of the Fabaceae, such as soybeans, peas, lentils and beans such as soybean, the host plant is preferably selected from these plants. The host may also be a synthetic *B. napus* or a double haploid *B. napus* line.

The transgenic, shatter resistant plant according to the invention may also be a double haploid plant. The double haploid plant can be generated e.g. by culturing microspores obtained from the transformed plant, followed by chromosome doubling (e.g. induced by colchicine treatment) and regeneration.

In addition the use of SHN transcription regulatory elements, especially SHN2 transcription regulatory element (SEQ ID NO: 18 or the smallest active fragment thereof) or the transcription regulatory element of a nucleotide sequence encoding a SHN2 ortholog, may be used to confer dehiscence zone specific expression and may thus be used to confer pod shatter resistance. For this purpose a nucleic acid sequence which modulate the pod structure, especially the anatomical structure of the pod dehiscence zone, may be operable linked downstream of the transcription regulatory element. Examples nucleic acid sequences suitable are for example the *Arabidopsis* FRUITFUL gene (FUL or AGL8; EP 1002087) or homologs thereof. Alternatively the promoter may be used in gene silencing constructs, resulting in pod shatter resistance. For example a short antisense fragment of the *Arabidopsis* IND1 gene or a sense/antisense fragment (inverted repeat) may be operably linked downstream of the transcription regulatory element. For gene silencing constructs, see below. Likewise, a nucleic acid sequence encoding a SHN-repressor domain fusion protein may be operably linked to a SHN transcription regulatory element, such as the SHN2 promoter.

C) Male Sterile Plants

Further provided are transgenic male sterile plants and method for making these using a SHN nucleic acid sequence according to the invention. Transgenic male sterile plants can be generated by transforming a host plant cell with a vector comprising a suitable promoter operably linked to a SHN-repressor domain fusion protein (preferably a SHN-EAR protein) encoding DNA sequence and optionally a suitable 3'nontranslated nucleic acid region. The promoter sequence is suitably selected from a dehiscence zone specific promoter active during anther dehiscence, an anther specific promoter or a tapetum specific promoter (for all see above), or the SHN2 promoter (SEQ ID NO: 18) or an active fragment thereof A chemically inducible promoter may also be used. If the chemical is sprayed at the right stage of flower development the sprayed plants will be sterile.

Overexpression of the SHN-EAR protein (or of another SHN-repressor domain fusion protein) during anther and/or pollen development leads to male sterility. "Male sterility" is herein defined as a significantly reduced release of mature pollen grains from the anther, preferably the complete absence of pollen release.

Transgenic male sterile plants may be used for producing hybrid seeds, for example by growing male sterile (MS) and male fertile plants (fertility restorer lines, RF) in rows next to each other allowing cross pollination of the male sterile plants. The seed collected from the male sterile plants are pure hybrid seeds. To maintain the pure male sterile line, anther dehiscence can be achieved mechanically from isolated anthers and used for brush or blow pollination on the same line. The hybrids are produced by crossing the MS lines to RF lines for seed crop production. The RF line comprises for example a homologous (from same crop) SHN gene, optionally encoding a SHN protein with a fusion to an Activation domain, such as the transcriptional activation domain of the VP16 protein from Herpes simplex virus or the yeast GAL4 (see Wilde et al. 1994, Plant Mol. Biol. 24, 381-388 and Moore et al. 1998, Proc. Natl. Acad. Sci. 95, 376-381), under control of a strong promoter expressed in the anther dehiscent zone. The promoter in the RF line should have higher expression levels (preferably 10 times) than that of the promoter driving the Repressor SHN-EAR gene in the MS line. The high expression of the homologous SHN (preferably with an Activation domain) will out-compete the Repressor SHN-EAR and allow anther dehiscence and pollen release that will pollinate the crop plant by natural cross-pollination, e.g. by wind or bees.

Male sterile plants may also be used for other purposes, such as reducing pollen dispersal into the environment and allergenicity problems caused by pollen. In one embodiment the male sterile plants are plants which can be propagated by vegetative propagation, such as grasses. Male sterile plants according to the invention may also be used to produce pharmaceutically active molecules in such transgenic plants. The male sterility reduces the risk of the transgenes spreading to other plants. A plant according to the invention may therefore additionally comprise a chimeric gene encoding a pharmaceutical protein or protein fragment, such as antigens, antibodies or antibody chains, and the like.

In addition the use of SHN transcription regulatory elements, especially SHN2 transcription regulatory element (SEQ ID NO: 18 or the smallest active fragment thereof) or the transcription regulatory element of a nucleotide sequence encoding a SHN2 ortholog, may be used to confer dehiscence zone specific expression and may thus be used to confer male sterility. For this purpose genes for mutants involved in anther dehiscence can be used, e.g AtMYB26 (Steiner-Lange, 2003, Plant J. 34: 519-528), delayed dehiscence1 (Sanders et al, 2000, Plant Cell 12: 1041-61). To create specific loss-of-function in the anther dehiscence zone an antisense or RNAi strategy can be followed, or a chimeric transcriptional factor repressor as described using e.g. the EAR repressor domain (Hiratsu et al 2003, supra). Another way is to use the SHN2 promoter to specifically disrupt the dehiscent zone using a nucleic acid sequence encoding for example a cytotoxic protein or a RNA may be operably linked downstream of the transcription regulatory element Examples of nucleic acid sequences suitable are the gene encoding the ribonuclease barnase from *Bacillus amyloliquefaciens* (see EP 0344029 B1), diphtheria toxin, RNase-T1 from *Aspergillus oryzae* (Quaas et al. 1988, Eur J Biochem 173:617-622) or others.

In another embodiment a SHN gene silencing construct, whereby a sense and or antisense SHN RNA is transcribed in the host cell is used to generate male sterile plants (see below).

D) Postharvest/Processing Fleshy Fruit Improvement: Texture, Firmness, Soluble Solids Of Whole Fruit and Juice During fruit development (e.g. of tomato) the ovary wall becomes the pericarp, which is covered by a thin cuticle. The skin of the pericarp consists of an epidermal cell layer and three to four layers of collenchymous tissue. The outer epidermal cells contain no stomata, so that water content is regulated via cuticle permeability. Due to the fact that SHN proteins were found to result in an increased water loss through the cuticle, the production of SHN proteins in fruit or fruit cells/tissues (especially the outer epidermal cells) results in an increased cuticular water loss of the developing fruit and in fruit with a higher % weight soluble solids than found in the fruit of control plants. The percentage of soluble solids is increased by at least 1%, 2%, 3%, more preferably by at least 5%, 6%, 7% or more, compared to controls.

Soluble-solids concentration are defined in °Brix, that is a standard refractometric measure primarily detecting reducing sugars, but also affected by other soluble constituents. °Brix can be measured by a hand-held refractometer (e.g. American Optical Corp., Buffalo, N.Y.), where a 1 °Brix is approximately 1% w/w.

Soluble solids are an important quality trait, especially for the fruit processing industries. Other important traits are fruit texture and firmness, as well as flavor, which are also influenced by fruit water content and can therefore be modified by overexpressing one or more SHN proteins according to the invention.

In one embodiment transgenic plants are provided, comprising within their genome a chimeric gene which comprises a fruit peel specific promoter operably linked to a SHN protein encoding DNA sequence according to the invention. Also provided are the mature fruit of those plants, as well as seeds and progeny thereof. In one embodiment the phenotype of the transgenic fruit is modified compared to the fruit of non-transgenic plants in that the percentage soluble solids is increased, and/or the fruit texture and/or firmness is increased, and/or the fruit flavour is improved. In a preferred embodiment the host plant is a tomato plant (*Lycopersicon* species) and the modified fruit is a tomato. Processing tomatoes require a higher percentage of soluble solids than fresh market tomatoes and the fruit according to the invention are therefore particularly suitable for the processing industry (tomato pastes, canned tomatoes, cooked tomatoes, etc.). In one embodiment the processed pure/juice is be improved for one or more processing characteristics, including pH, titratable acidity, precipitate weight ratio, total solids, serum viscosity, efflux viscosity and color. The fruit will also be easier and cost effective to transport with less damage and spoilage.

*Lycopersicon* species include *L. cheesmanii, L. chilense, L. chmielewskii, L. esculentum* (tomato), *Lycopersicon esculentum* var. *cerasiforme* (cherry tomato), *L. esculentum×L. peruvianum, L. glandulosum, L. hirsutum, L. minutum, L. parviflorum Lycopersicon pennellii, L. peruvianum* (Peruvian tomato), *L. peruvianum* var. *humifusum* and *L. pimpinellifolium* (currant tomato).

The modified phenotype can be generated by transforming any plant host producing fleshy fruit, for example grape, peach, plum, cherry, mango, strawberry can be transformed in order to concentrate the soluble solids and reduced post-harvest damage prior to processing for fruit concentrate products and/or improve fruit flavour and fruit juices.

Suitable fruit specific promoters or promoters specifically expressed during fruit development and/or in a certain cells/tissues of the fruit (especially the outer epidermal cells) are known in the art. Examples are the promoter of the tomato cuticular wax gene LeCER6 (Vogg et al, 2004, J. Exp Bot. 55: 1401-10) or for example provided in U.S. Pat. No. 5,753,475 (describing e.g. a tomato polygalacturonase promoter, which is active in at least the breaker through red fruit stage in tomato fruit). Other suitable promoters can be easily identified by a person skilled in the art. For example, for each fleshy fruit, a fruit skin or epidermis specific promoter can be identified.

In a preferred embodiment the transgenic fruit are more solid in texture and/or have an improved flavour and/or improved processing characteristics compared to controls.

E) Plants with Enhance Wound Healing Properties and/or Enhanced Suberization

In yet a further embodiment transgenic plants, expressing one or more SHN proteins according to the invention, are provided, which have an enhanced wound healing phenotype. "Enhanced wound healing" refers to the enhanced ability to form a protective layer on the wounded tissue surface following wounding. The protective layer may be either produced more rapidly than in control plants (e.g. non-transgenic plants) or it may be altered in thickness and/or chemical composition.

Wounding may occur during processing of plants (e.g. during harvest) or naturally by wind, animals feeding on tissue, etc. Often wounding may result in yield loss and in quality loss of crop plants. In a preferred embodiment the host plant is potato (*Solanum tuberosum*). Preferably the SHN coding sequence is expressed under a tuber-peel specific promoter. Tubers of transgenic plants preferably comprise a protective shiny outer tuber layer that would protect the tubers from mechanical damage and display an attractive tuber quality for consumer preference. In addition, damage to tubers during harvest and post-harvest transport is reduced by enhanced wound healing, thus preventing further spoilage to the rest of the tubers stored along with the damaged tubers. This also contributes to improved general tuber quality and reduction in post-harvest yield losses.

In another embodiment woody tree species (e.g. *Populus, Salix, Quercus, Eucalyptus* species) are transformed with a vector according to the invention, whereby one or more SHN proteins are produced by the transgenic tree, leading to cork cells with enhanced suberin formation. The high production of woody biomass as renewable energy use, as well as traditional uses for timber and paper is being addressed by development of genomics and biotechnological resources (Taylor, 2002, Annals Botany 90: 681-689). Transformation systems and specific promoters are identified that enable the expression of the SHN genes to regulate the deposition of increased suberin in the cork of woody species. The natural production of suberin in the cork of Quercus can be enhanced, and also more suberin produced in the other woody trees. Cork is a natural defensive mechanism against drought, brush fires and temperature fluctuations in the natural habitat where the cork trees grow. Thus producing an enhanced suberin cork layer in other trees would provide similar properties to the other woody tree species. Cork is actually made of water-resistant cells that separate the outer bark from the delicate interior bark. It has a unique set of properties not found in any other naturally existing material. It is lightweight, rot resistant, fire resistant, termite resistant, impermeable to gas and liquid, soft and buoyant. Thus these qualities would improve the wood quality of other woody trees providing new applications. Other uses of processed corkboard are for soundproofing and as insulation in refrigerators and cold storage plants; gaskets and washers in engines and motors; pipe coverings; polishing wheels; floor and wall coverings in addition to the traditional beverage bottle caps (including wine and champagne).

Whole plants, seeds, cells, tissues and progeny (such as F1, F2 seeds/plants, etc) of any of the transformed plants described above are encompassed herein and can be identified by the presence of the transgene in the DNA, for example by PCR analysis using total genomic DNA as template and using SHN specific PCR primer pairs. Also "event specific" PCR diagnostic methods can be developed, where the PCR primers are based on the plant DNA flanking the inserted chimeric gene, see U.S. Pat. No. 6,563,026. Similarly, event specific AFLP fingerprints or RFLP fingerprints may be developed which identify the transgenic plant or any plant, seed, tissue or cells derived there from.

It is understood that the transgenic plants according to the invention preferably do not show non-desired phenotypes, such as yield reduction, enhanced susceptibility to diseases or undesired architectural changes (dwarfing, deformations) etc. and that, if such phenotypes are seen in the primary transformants, these can be removed by normal breeding and selection methods (crossing/backcrossing/selfing, etc.). Any of the transgenic plants described herein may be homozygous or hemizygous for the transgene.

F) Gene Silencing and the Generation of Loss-of-Function Phenotypes by SHN-Repressor Domain Fusions Proteins For certain applications it is desired to generate transgenic plants in which a SHN gene or the SHN gene family is silenced or is silenced in specific cells or tissues of the plant. "Gene silencing" refers to the down-regulation or complete inhibition of gene expression of one or more target genes. The use of inhibitory RNA to reduce or abolish gene expression is well established in the art and is the subject of several reviews (e.g Baulcombe 1996, Stam et al. 1997, Depicker and Van Montagu, 1997). There are a number of technologies available to achieve gene silencing in plants, such as chimeric genes which produce antisense RNA of all or part of the target gene (see e.g. EP 0140308 B1, EP 0240208 B1 and EP 0223399 B1), or which produce sense RNA (also referred to as co-suppression), see EP 0465572 B1.

The most successful approach so far has however been the production of both sense and antisense RNA of the target gene ("inverted repeats"), which forms double stranded RNA (dsRNA) in the cell and silences the target gene. Methods and vectors for dsRNA production and gene silencing have been described in EP 1068311, EP 983370 A1, EP 1042462 A1, EP 1071762 A1 and EP 1080208 A1.

A vector according to the invention may therefore comprise a transcription regulatory region which is active in plant cells operably linked to a sense and/or antisense DNA fragment of a SHN gene according to the invention. Generally short (sense and antisense) stretches of the target gene sequence, such as 17, 18, 19, 20, 21, 22 or 23 nucleotides of cording or non-coding sequence are sufficient. Longer sequences can also be used, such as 100, 200 or 250 nucleotides. Preferably, the short sense and antisense fragments are separated by a spacer sequence, such as an intron, which forms a loop (or hairpin) upon dsRNA formation. Any short stretch of SEQ ID NO: 1-10 may be used to make a SHN gene silencing vector and a transgenic plant in which one or more SHN genes are silenced in all or some tissues or organs. A convenient way of generating hairpin constructs is to use generic vectors such as pHANNIBAL and pHELLSGATE, vectors based on the Gateway® technology (see Wesley et al. 2004, Methods Mol. Biol. 265:117-30; Wesley et al. 2003, Methods Mol. Biol. 236:273-86 and Helliwell & Waterhouse 2003, Methods 30(4):289-95.), all incorporated herein by reference.)

By choosing conserved nucleic acid sequences all SHN gene family members in a host plant can be silenced. Encompassed herein are also transgenic plants comprising a transcription regulatory element operably linked to a sense and/or antisense DNA fragment of a SHN gene and exhibiting a SHN gene silencing phenotype. Gene silencing constructs may also be used in reverse genetic approaches, to elucidate or confirm the function of a SHN gene or gene family in a host species.

In one embodiment SHN gene silencing is used to generate podshatter resistance and/or male sterility in host plants. However, due to structural and functional redundancy, gene silencing approaches may not always be successful and may show no phenotypic change or only a subtle phenotype, possibly revealed only under extreme environmental conditions, when knocked-out. A preferred approach is, therefore, to generate male sterile plants and/or podshatter resistant plants by over-expressing a SHN-repressor domain fusion protein in the host cells, as described above. In a preferred embodiment this chimeric protein is a SHN-EAR fusion protein or a En-SHN fusion protein, e.g. a $En^{298}$-SHN fusion protein.

G. Transgenic Plants Having Enhanced Salinity Tolerance

A transgenic, salinity tolerant (salt tolerant) plant can be generated by transforming a plant host cell with a nucleic acid sequence encoding at least one SHN protein under the control of a suitable promoter, as described above and in the Examples, and regenerating a transgenic plant from said cell. Preferred promoters are promoters are constitutive, inducible or root specific promoters.

"Salinity tolerance" or "enhanced salinity tolerance" refers to the ability to grow and survive on saline soil or growth medium, especially without yield loss or only with minimal yield loss. Preferably, a salinity tolerant plant has a percentage of survival on saline soil, which is at least 10, 20, 30, 40, 50, 80, 90 or 100% higher than that of the control plants.

Salinity tolerance can be determined as described in the Examples (by assessing the number of plants surviving when subjected to saline medium) or by growing the plants and controls on soils with various salinity levels, such as soils having an $EC_e$ value (Electrical Conductivity of the extract) of 2-4 dS/m (deciSiemens per meter), 4-8 dS/m, 8-16 dS/m or above 16 dS/m (very saline). A plant is salinity tolerant if it can grow on soil with a higher $EC_e$ value than the control plant, without yield loss or with only minimal yield loss. Preferably, SHN overexpressing plants are able to grow without yield loss (or only with minimal yield loss) on soil with an ECe value which is at least one, preferably at least 2, more preferably at least 3 or more dS/m units higher than that of the control.

In a preferred embodiment the plant is both salinity tolerant and drought tolerant.

H. Non-Transgenic Plants Comprising a Modified Phenotype

It is also an embodiment of the invention to use non-transgenic methods, e.g. mutagenesis systems such as TILL-ING (Targeting Induced Local Lesions IN Genomics; McCallum et al., 2000, Nat Biotech 18:455, and McCallum et al. 2000, Plant Physiol. 123, 439-442, both incorporated herein by reference) and selection to generate plant lines which produce higher levels of one or more SHN proteins according to the invention. Without limiting the scope of the invention, it is believed that such plants could comprise point/deletion mutations in the promoter that are binding sites for repressor proteins that would make the host SHI gene constitutive or higher in expression. Preferably SHN protein levels in the mutant or parts of the mutant are at least about 2, 5, 10, 15% or more increased in the mutant compared to non-mutant plants. TILLING uses traditional chemical mutagenesis (e.g. EMS mutagenesis) followed by high-throughput screening for mutations (e.g. using Cel 1 cleavage of mutant-wildtype DNA heteroduplexes and detection using a sequencing gel system), see e.g. Henikoff et al. Plant Physiology Preview May 21, 2004. Thus, non-transgenic plants, seeds and tissues comprising an enhanced SHN gene expression in one or more tissues and comprising one or more of the SHN phenotypes according to the invention (e.g. enhanced drought tolerance, enhanced salinity tolerance, enhanced suberization, etc., all as described above) and methods for generating and identifying such plants is encompassed herein.

The method comprises in one embodiment the steps of mutagenizing plant seeds (e.g. EMS mutagenesis), pooling of plant individuals or DNA, PCR amplification of a region of interest, heteroduplex formation and high-throughput detection, identification of the mutant plant, sequencing of the mutant PCR product. It is understood that other mutagenesis and selection methods may equally be used to generate such mutant plants. Seeds may for example be radiated or chemically treated and the plants screened for a modified SHN phenotype, such as enhanced drought tolerance.

In another embodiment of the invention, the plant materials are natural populations of the species or related species that comprise polymorphisms or variations in DNA sequence at the SHN orthologous coding and/or regulatory sequence. Mutations at the SHN gene target can be screened for using a ECOTILLING approach (Henikoff et al 2004, supra). In this method natural polymorphisms in breeding lines or related species are screened for by the above described TILLING methodology, in which individual o'r pools of plants are used for PCR amplification of the SHN target, heteroduplex formation and high-throughput analysis. This can be followed up by selecting of individual plants having the required mutation that can be used subsequently in a breeding program to incorporate the desired SHN-orthologous allele to develop the cultivar with desired trait.

In a further embodiment non-transgenic mutant plants which produce lower levels of SHN protein in one or more tissues are provided, or which completely lack SHN protein in specific tissues or which produce a non-functional SHN protein in certain tissues, e.g. due to mutations in one or more endogenous SHN alleles. For this purpose also methods such as TILLING may be used. Seeds may be mutagenized using e.g. radiation or chemical mutagenesis and mutants may be identified by detection of DNA polymorphisms using for example CEL 1 cleavage. Especially, mutants which comprise mutations in one or more SHN alleles and which are shatter resistant and or male sterile are provided. Non-functional SHN alleles may be isolated and sequenced or may be transferred to other plants by breeding methods.

Mutant plants can be distinguished from non-mutants by molecular methods, such as the mutation(s) present in the DNA, SHN protein levels, SHN RNA levels etc, and by the modified phenotypic characteristics.

The non-transgenic mutants may be homozygous or heterozygous for the mutation conferring the enhanced expression of the endogenous SHN gene(s) or for the mutant SHN allele(s).

Sequences
SEQ ID NO 1: *Arabidopsis thaliana* genomic DNA encoding SHN1
SEQ ID NO 2: *Arabidopsis thaliana* genomic DNA encoding SHN2
SEQ ID NO 3: *Arabidopsis thaliana* genomic DNA encoding SHN3
SEQ ID NO 4: *Arabidopsis thaliana* SHN1 transcript
SEQ ID NO 5: *Arabidopsis thaliana* SHN2 transcript
SEQ ID NO 6: *Arabidopsis thaliana* SHN3 transcript
SEQ ID NO 7: *Arabidopsis thaliana* SHN1 coding sequence
SEQ ID NO 8: *Arabidopsis thaliana* SHN2 coding sequence
SEQ ID NO 9: *Arabidopsis thaliana* SHN3 coding sequence
SEQ ID NO 10: *Oryza sativa* OsSHN1 coding sequence
SEQ ID NO 11: *Arabidopsis thaliana* SHN1 amino acid sequence
SEQ ID NO 12: *Arabidopsis thaliana* SHN2 amino acid sequence
SEQ ID NO 13: *Arabidopsis thaliana* SHN3 amino acid sequence
SEQ ID NO 14: *Oryza sativa* OsSHN1 amino acid sequence
SEQ ID NO 15: SHINE "mm" consensus domain
SEQ ID NO 16: SHINE "cm" consensus domain
SEQ ID NO 17: transcription regulatory sequence of SHN1
SEQ ID NO 18: transcription regulatory sequence of SHN2
SEQ ID NO 19: transcription regulatory sequence of SHN3
SEQ ID NO 20: transcription regulatory sequence of OsSHN1
SEQ ID NO 21: EAR repressor domain
SEQ ID NO 22: coding sequence of EAR repressor domain
SEQ ID NO 23: cDNA of OsSHN2
SEQ ID NO 24: amino acid sequence of OsSHN2

FIGURE LEGENDS

FIG. 1—Chain length distribution [% of compound class] for the four major fractions in the leaf cuticular wax of wild type and shn.

Figure 2A:
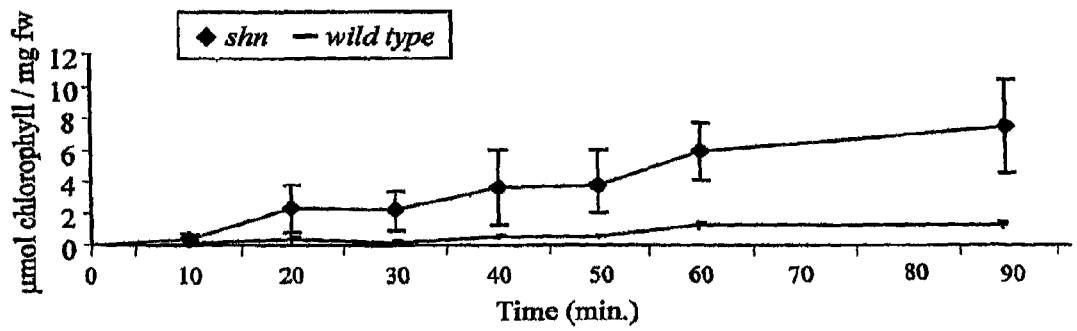

FIG. 2—The shn Mutant and 35S::SHN1 Plants Phenotype and Surface Permeability.
(A) Chlorophyll leaching assays with mature rosette leaves of shn and wild-type Ws immersed in 80% ethanol for different time intervals. The results are derived from three independent experiments and depicted with standard error of the mean for each time point.
(B) Chlorophyll leaching assays as described above but using mature rosette leaves derived from 35S::SHN1 (#2-2) progeny and wild-type plants.
(C) Rate of water loss from the progeny of the activation tag shn mutant, two 35S::SHN1 primary transformants (#2-2 and #2-5) and wild type Ws. Four rosette explants (root system and inflorescence stem detached) were weighed during the time intervals depicted. The results are derived from three independent experiments and depicted with standard error of the mean for each time point.

Figure 3:
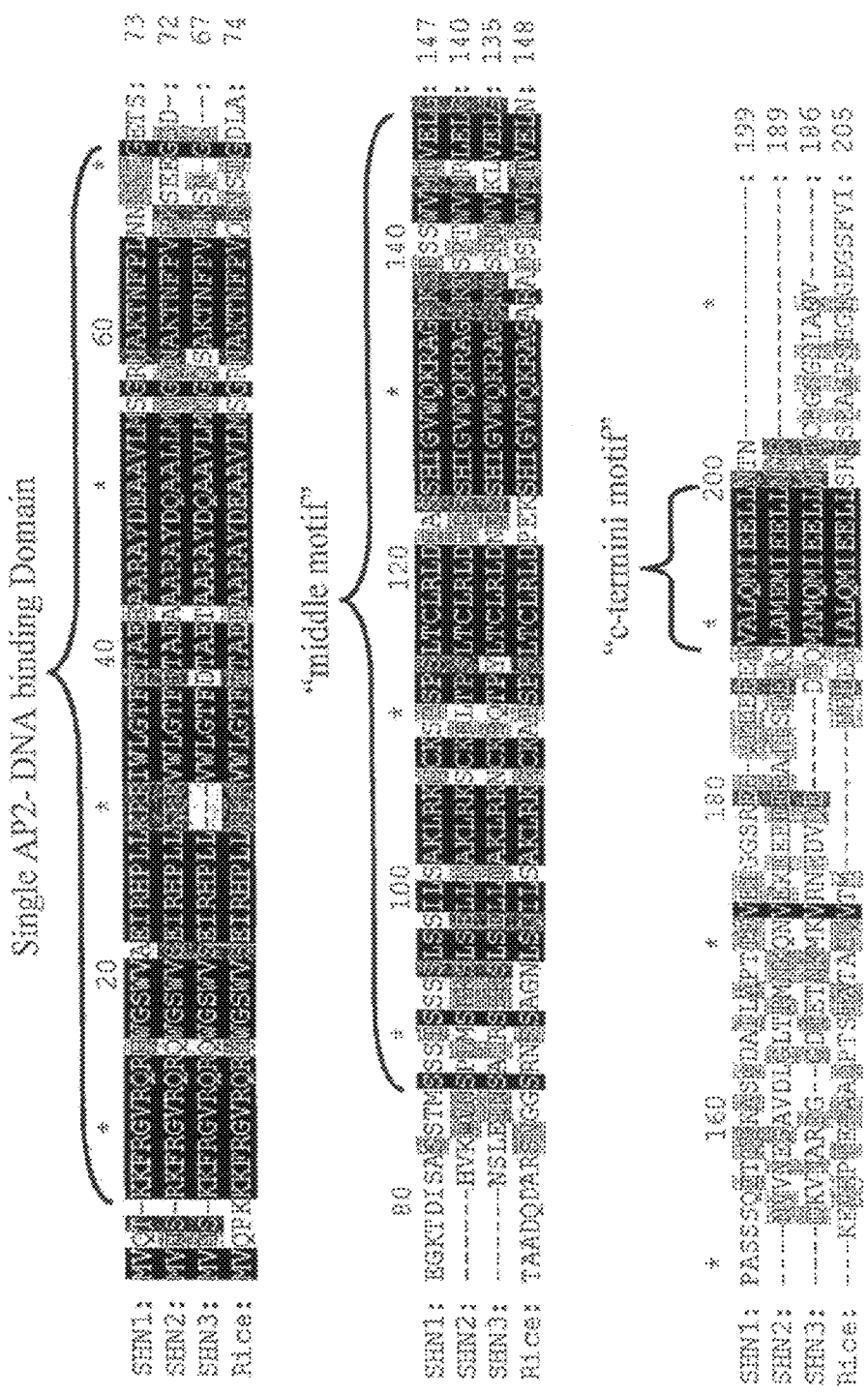

FIG. 3—The SHINE Clade of *Arabidopsis* AP2/EREBP Transcription Factor Family. Sequence alignment of the four SHN proteins. SNH1-SEQ ID NO:11; SNHN2-SEQ ID NO:12; SHN3-SEQ ID NO:13; *Oryza sativa* (rice)-SEQ ID NO:14). SHN clade members contain a single AP2 domain at their N-termini, a conserved middle domain (termed "mm"; SEQ ID NO:15) and a most conserved C-terminal domain (termed "cm"; SEQ ID NO:16). Black background indicates 100% conservation, gray is 75% and light gray is 50% conservation.

Figure 4:
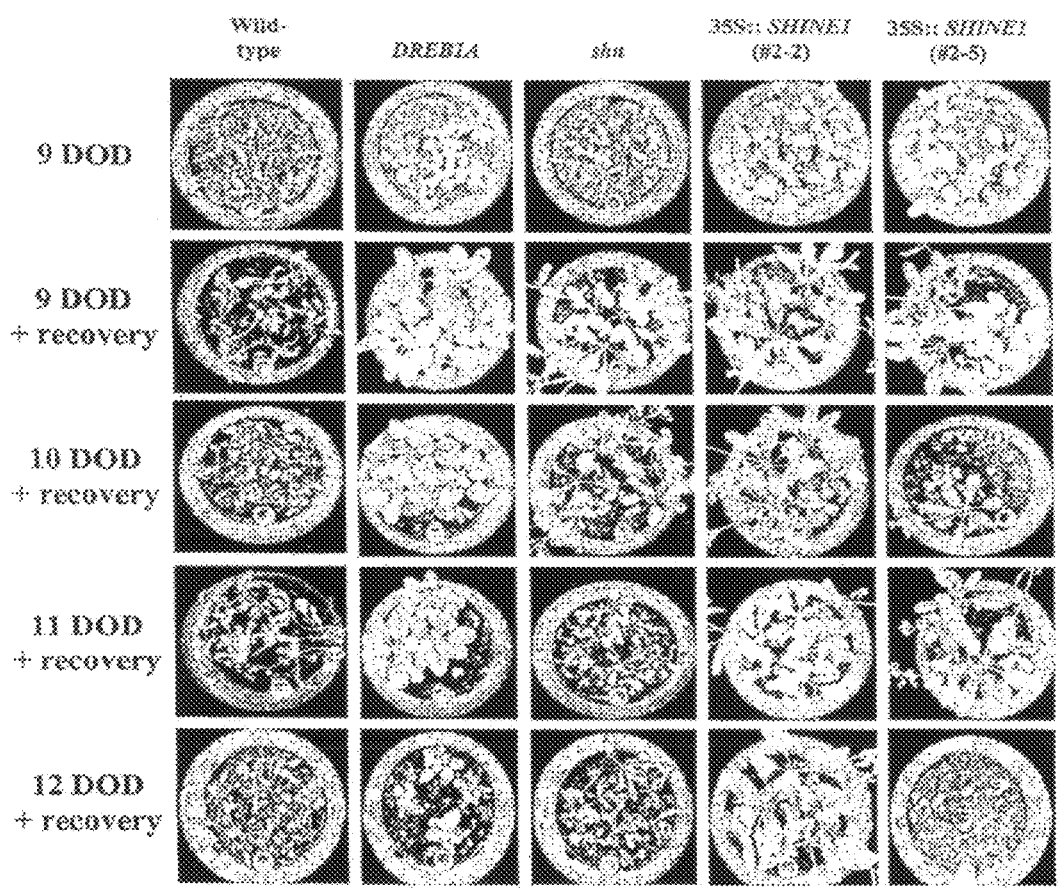

FIG. 4—Drought Tolerance Experiment with shn and 35S::SHN1 Lines. Fifteen days old seedlings of either wild-type Ws, progenies of shn, two 35S::SHN1 lines (#2-2 and #2-5) and a positive control rd29-DRE1A line (providing drought tolerance; Kasuga et al. 1999, supra) were exposed for a period of 9 to 12 days of dehydration. Subsequently, seedlings were watered and their appearance after a week (recovery) is presented in the image (apart from the first row at 9 DOD, in which pictures were taken directly at the end of the dehydration period). DOD, Days of dehydration.

The following non-limiting Examples describe the use of SHN genes for modifying plant phenotypes. Unless stated otherwise in the Examples, all recombinant DNA techniques are carried out according to standard protocols as described in Sambrook et al. (1989) *Molecular Cloning: A Laboratory Manual*, Second Edition, Cold Spring Harbor Laboratory Press, and Sambrook and Russell (2001) *Molecular Cloning: A Laboratory Manual*, Third Edition, Cold Spring Harbor Laboratory Press, NY; and in Volumes 1 and 2 of Ausubel et al. (1994) *Current Protocols in Molecular Biology, Current Protocols*, USA. Standard materials and methods for plant molecular work are described in *Plant Molecular Biology Labfax* (1993) by R. D. D. Croy, jointly published by BIOS Scientific Publications Ltd (UK) and Blackwell Scientific Publications, UK.

EXAMPLES

Example 1

Material and Methods 1.1 Plant Material and Drought Tolerance Experiment

All plants, including the activation tag population (Marsch-Martinez et al., 2002, Plant Physiol. 129: 1544-1556) and transgenic lines were grown in the greenhouse at around 22° C. and were in the *Arabidopsis* ecotype Wassilewskija (Ws). For the drought tolerance experiments, soil mixture comprised 1 part of sand and perlite and 2 parts of compost. Seeds were sown (after 3 nights at 4° C.) at density of six plants per 4 cm pot in a tray with 51 pots (Aracon containers, BetaTech, Belgium). Mineral nutrients were supplied 10 days after germination and at two weeks after germination the plants were subjected to drought (for 9, 10, 11 or 12 days) by transferring the pots to dry trays (after drying each pot from outside). Every 2 days in drought, the plants were moved within the tray to nullify pot position effects. Subsequently, plants were rehydrated and observed for recovery after one week. The drought experiments were conducted with 4 replications and the whole experiment repeated 5 times.

1.2 Isolation of Flanking DNA and Sequence Analysis

DNA was isolated according to Pereira and Aarts (1998, Transposon tagging with the En-I system, Totowa, N.J., Humana Press), from two leaves or young flower buds, and 10 ng of genomic DNA was used for Thermal Asymmetric Interlaced-PCR (TAIL PCR) as described by (Marsch-Martinez et al., 2002, supra). A re-PCR was generally performed before sequencing the amplified fragments, and identifying the insert position in the *Arabidopsis* genome using a BlastN algorithm (Altschul et al. 1990, J. Mol. Biol. 215:403-410). Multiple sequence alignments were performed using CLUSTAL X (Thompson et al. 1997, Nucl. Acid Res. 25, 4876-4882) and DNASTAR (DNASTAR Inc. Madison, Wis.) while the GENEDOC (Nicholas et al. 1997, EMBNET News 4, 1-4) and TreeView (Page, 1996, Comp. Applic. Biosci. 12: 357-358) programs were used for editing the alignment and producing the phylogenetic tree, respectively. Phylogenetic analysis including bootstrapping was conducted as described by Lucker et al. (2002, Eur. J. Biochem. 269, 3160-3171).

1.3 Generation of Plant Transformation Constructs and Transgenic *Arabidopsis*

Fragments encompassing the full length coding regions were amplified (using pfu DNA polymerase) from flower buds cDNA (for SHN1, At1g15360) or genomic DNA (for At5g 11190, SHN2 and At5g25390, SHN3) to generate the three overexpression constructs. The cDNA (produced as described below in Gene Expression Analysis) and genomic DNA used for amplification were from the *Arabidopsis* ecotype Columbia. Oligonucleotides AP35 and AP36 were used to amplify SHN1, while oligonucleotides AP69 and AP70 were used to amplify SHN2.

Both pairs of oligonucleotides introduced BamHI and SstI restriction sites to the amplified fragments at their 5' and 3', respectively, which were utilized to ligate the coding region fragments to the BamHI and SstI sites in the pBI121 binary vector (Clontech, Palo Alto, Calif.) in between a 35S promoter of the cauliflower mosaic virus (CaMV) and a nopaline synthase (NOS) terminator. Oligonucleotides AP71 and AP72 were used to amplify SHN3 and introduced BglII and XhoI restriction sites to the amplified fragment at the 5' and 3', which were utilized to ligate the coding region fragment to the BamHI and SalI sites in the pNEW binary vector (a modified pBI121 binary vector, Nayelli Marsch-Martinez, unpublished) in between the 35S CaMV promoter and the NOS terminator. For generating the promoter::GUS constructs, fragments upstream to the ATG codon of each gene (2 kb of SHN1 and SHN3 and 1.857 kb of SHN2) were amplified from genomic DNA (ecotype Columbia) using Taq DNA polymerase and oligonucleotides which introduced XbaI NcoI restriction sites at the 5' and 3', respectively. Only in the case of SHN3 the amplified fragment contained already an endogenous XbaI site at the 5' end. This allowed ligation of the fragments to the XbaI and NcoI sites in a modified pBinPlus vector (Raffaella Greco, unpublished) upstream of the β-glucuronidase (GUS) reporter gene. The oligonucleotides AP61 and AP62 were used to amplify the SHN1 upstream region, AP147 and AP148 for SHN2 and AP149 and AP150 for SHN3. In all cases fragments were A-tailed and introduced to the pGEM-T Easy vector as described by the manufacturer (Promega) and subsequently sequenced from both sides before digestion and ligation to the Binary vector. PCR, restriction digests, plasmid DNA isolation and gel electrophoresis were performed using standard protocols. The rd29A-DRE1A construct was similar to that described (Kasuga et al., 1999, Nat. Biotech. 17, 287-291), except that the gene fusion was inserted into pBinPlus (van Engelen et al., 1995, Trans. Res. 4, 288-290). The constructs were introduced into the plants using the floral dipping transformation method (Clough and Bent, 1998, Plant J. 16, 735-743). The seeds were plated on one-half-strength Murashige and Skoog medium (1/2MS; Murashige and Skoog, 1962, Physiol. Plant. 15, 473-497) and seedlings selected on 50 mg/L kanamycin were subsequently transferred to the greenhouse.

```
Oligonucleotides:
AP35  (5'-CGGATCCATGGTACAGACGAAGAGTTCAG-3')

AP36  (5'-CGAGCTCGATTTAGTTTGTATTGAGAAGC-3')

AP69  (5'-CGGATCCATGGTACATTCGAGGAAGTTCCG-3')

AP70  (5'-CGAGCTCTCAATCCAATTCAGCAACTCC-3')

AP71  (5'-CAGATCTGAAGAATGGTACATTCGAAG-3')

AP72  (5'-CTCGAGCCTTTAGACCTGTGCAATGG-3')
```

-continued

```
AP61   (5'-CTCTAGAACGAATGGCCGTTGATCAGAG-3')

AP62   (5'-CCCATGGTTACTTACTCTGTG-3')

AP147  (5'-CTCTAGAGATTGGGTACTAGGTTAAGG-3')

AP148  (5'-CCCATGGTTTAGTTTCCTTCA-3')

AP149  (5'-ATCGTGTGAAACGTCAATCG-3')

AP150  (5'-CCCATGGCTTCGAATGTACCATGGTTCTG-3')

AP151  (5'-CTGGATCTGGATCTAGAACTCCGTTTGGGTTTC
        GCTTAA-3')

(AP151 is an EAR repressor primer)
```

1.4 Gene Expression Analyses

Total RNA for Reverse Transcriptase-PCR (RT-PCR) was isolated from mature, green, rosette leaves derived from 4 weeks old shn activation tag mutant and wild type (ecotype WS) plants using the TrizolReagent as described by the manufacturer (Invitrogen, Life technologies). Approximately 1 µg of total RNA was used for DNase I treatment and cDNA synthesis (using SuperScriptII reverse transcriptase) as described by the supplier (Invitrogen, Carlsbad, Calif.). The cDNA was diluted 50 times and used for amplification using specific oligonucleotides for the actin gene

```
RACTP1, 5'-GCGGTTTTCCCCAGTGTTGTTG-3'

RACTP2, 5'-TGCCTGGACCTGCTTCATCATACT-3'
``` to equalize the concentrations of the cDNA samples. Subsequently the diluted cDNA was utilized to perform a PCR reaction using specific oligonucleotides designed to amplify the two genes flanking the insertion site. Oligonucleotides AP8 and AP9, to amplify the At1g15350 gene and AP6 and AP7, to amplify At1g15360 (SHN1). The reaction conditions for PCR included a denaturing step of 95° C. for 3 min, followed by 35 cycles of 1 min at 95° C., 1 min at 55° C., and 1.5 min at 72° C., ending with an elongation step of 5 min at 72° C. For the control PCR with actin oligonucleotides, 30 amplification cycles were used.

```
AP8 5'-CAAACGCTCAAGGGTCTCGTC-3'

AP9 5'-CTGAGCACAACCAAGTCCACCA-3'

AP6 5'-CTTCATCGCTCTCTTCCATCC-3'

AP7 5'-CCAATACTTCTTCTCTGCTGC-3'
```

1.5 Wax Extraction and Chemical Analysis

Cuticular wax was extracted exhaustively by dipping intact leaves twice for 30 sec into 20 mL of chloroform (>99%; Fisher Scientific, Nepean, Ontario, Canada) at room temperature. Tetracosane (Sigma-Aldrich, Oakville, Ontario, Canada) was added as internal standard, the extracts were filtered, and the solvent was removed by a gentle stream of N2 while heating the solution to 50° C. Then all samples were treated with bis-N,N-(trimethylsilyl)trifluoroacetamide (BSTFA, Sigma-Aldrich) in pyridine (Fluka, Buchs, Switzerland, 30 min at 70° C.) to transform all hydroxyl-containing compounds into the corresponding trimethylsilyl derivatives. The extracted surface area was subsequently measured digitally by scanning photocopies of the leaves. The qualitative composition was studied with capillary GC (6890N, Agilent, Palo Alto, Calif., USA) with He carrier gas inlet pressure constant at 30 kPa and mass spectrometric detector (70 eV, m/z 50-750, 5973N, Agilent). GC was carried out with temperature-programmed injection at 50° C. oven for 2 min at 50° C., raised by 40° C. min$^{-1}$ to 200° C., held for 2 min at 200° C., then raised again by 3° C. min$^{-1}$ to 320° C. and held for 30 min at 320° C. The quantitative composition of the mixtures was studied by capillary GC (Agilent; 30 m HP-1, 0.32 mm i.d., df=1 µm) and flame ionization detection under the same gas chromatographic conditions as above, but H2 carrier gas inlet pressure was programmed for 50 kPa at injection, held for 5 min, then raised with 3 kPa min$^{-1}$ to 150 kPa and held for 40 min at 150 kPa. Single compounds were quantified against the internal standard by manually integrating peak areas.

1.6 Chlorophyll Leaching Assay, Fresh Weight and Stomata Analyses

For chlorophyll leaching assays, roots and inflorescence stems of 4 weeks old plants were cut off, and the remaining rosette was rinsed with tap water, weighed and put in tubes containing 30 ml of 80% ethanol at room temperature (gently agitating in the dark). Four hundred microliter were removed from each sample every ten minutes during the first hour, and then after 90 and 120 min. Absorbance of each sample was measured at 664 and 647 and the following formula (Lolle et al., 1997, Dev. Biol. 189, 311-321), was used to calculate the micromolar concentration of total chlorophyll per gram of fresh weight of tissue: Total micromoles chlorophyll=7.93 (A664)+19.53 (A647).

Seed from wild type and the mutant lines were stratified in cold (4° C.) for 3 nights and sown in 9-cm diameter pots, at a density of approximately 12 seeds/pot. The plants were given nutrition on the 10th day after germination, allowed to grow to 4 weeks then used for water-loss analysis. The rosette and emerging stems of plants were detached from the roots and weighed immediately for the fresh weight. All samples maintained at room temperature (22 degrees C.) were weighed at several regular time intervals. Initial observations were taken at short time intervals of 2 minutes and then later gradually increased to longer intervals of 1 hour. The samples were weighed for 7 hours or more. Observations were taken from 4 different plants of wild type and mutants, and the experiment was repeated in 3 batches at different days. The average fresh weight, average dry weight (samples were kept at 60 degrees for 2 days and then weighed), average rate of water loss per unit fresh weight and the standard deviation were calculated. A graph was plotted with average rate of water loss per unit fresh weight against time in minutes.

For stomatal density, pavement cell density and stomatal index measurements we used similar size and age mature green rosette leaves, derived from 6 weeks old plants of wild type and 35S::SHN1 line #2-2. Two leaves from four different plants (from each of the two genotypes) were used to generate imprints of their abaxial surface. A xylene-thermocol mixture made by dissolving thermocol in xylene until the solution becomes viscous was applied uniformly on the abaxial surface of the leaves and allowed to dry. Subsequently, the imprints were detached from the leaf surface, and pieces derived from the region in between the main vein and the leaf blade edge were mounted on glass microscope slides with 50% glycerol and observed under 20× magnification using a light microscope (Zeiss). Numbers of epidermal pavement cells and stomata were counted per mm$^2$ (two different regions per leaf) and stomatal index was calculated (Mishra, 1997, Ann. Bot. 80, 689-692).

1.7 GUS Staining and Microscopy

Tissues from various organs either from soil grown plants or seedlings grown on 1/2MS in vitro were analyzed for their GUS expression patterns. The GUS solution contained 100Mm sodium phosphate buffer, pH 7.0, 0.5 mg/ml 5-bromo-4-chloro-3-indolyl β-D glucoronic axid (X-Gluc, Duchefa, The Netherlands), 0.1% Triton, and 0.5 mM each of potassium ferri/ferrocyanide. Samples were vacuum infiltrated and incubated at 37° C. for 16 to 24 h and depleted from chlorophyll in 70% ethanol. Observation were conducted either under the binocular (WILD M3Z of Heerbrugg Switzerland, type-S), or with a light microscope (Zeiss) and an RS Photometrics CoolSNAP camera (MediaCybernetics®) was used to take the digital images, with the corresponding CoolSNAP software.

For Scanning Electron Microscopy (SEM) samples were glued on a sample holder with conductive carbon cement (Leit-C, Neubauer Chemikalien, Germany) and subsequently frozen in liquid nitrogen. The samples were transferred under vacuum to a dedicated cryo-preparation chamber (Oxford cryo-system, CT 1500 HF, Eynsham, UK) onto a sample stage at –90° C. Cryo-fractures were made at approx –150° C. using a cold (–196° C.) scalpel blade. The fractured samples were freeze dried for 3 min at –90° C. in vacuum (3×10–7 Pa) to remove water vapour contamination. After the sample surface was sputter-coated with 10 nm Platinum it was transferred to the cold sample stage (–190° C.) inside the Cryo-FESEM (JEOL 6300F Field Emission SEM, Japan, Tokyo) and subsequently analyzed with an accelerating voltage of 5 kV. Images were digitally recorded (Orion, Belgium).

Example 2

Identification of the Shine Mutant

By screening a collection of 2000 *Arabidopsis* transposon activation tag lines (Marsch-Martinez et al., 2002) a mutant plant was identified which showed leaf surface alterations (not shown). Both rosette and cauline leaves of the mutant (termed shine, shn) had a more brilliant, shiny green color when compared to wild type plants and often had curved-down edges (not shown). The stem of mature plants was often bowed-down, siliques were slightly smaller than wild type and also showed a more brilliant surface. Structure of other floral organs and plant fertility did not seem to be affected in shn. Progeny analysis of the self-pollinated shn mutant line suggested a dominant mutation (three quarters of the plants exhibited the shn phenotype).

Example 3

Alterations to Wax Load in the shn Mutant

Scanning electron microscopy (SEM) was utilized for a detailed comparison between the surfaces of wild type plant organs and those of shn. The surfaces of stems and siliques of *Arabidopsis* are covered by a dense mixture of different types of wax crystals while leaf surfaces normally exhibit only small numbers of epicuticular wax crystals. In contrast to wild type we detected more wax crystals on both adaxial and abaxial sides of rosette and cauline leaves of shn (data not shown). The leaf surface was not entirely covered by crystals, as in the case of wild type siliques and stems, but rather had irregular patches of plate-like wax crystals. An additional characteristic of the shn mutant was the presence of cuticular ridges on the surface of both cauline leaves and siliques, which were not detected in the wild type (data not shown). Such cuticular ornamentation was not visible on either the adaxial or abaxial surfaces of shn rosette leaves. Freeze fractionation of siliques and cauline leaf tissues further demonstrated the presence of the cuticular ridges in shn tissues, which showed similarity to the cuticular ridges present normally on surfaces of wild type *Arabidopsis* petals (data not shown). In this analysis the cuticle thickness did not seem to be drastically altered. Neither an increase in wax crystal numbers nor cuticular ridges were detected on surfaces of shn sepals, anther filament and petals.

A detailed chemical analysis of total wax mixtures was conducted in both shn and wild type leaf cuticles in order to quantify the changes in wax load detected by SEM. The shn mutant wax phenotype was characterized by a six-fold increase in wax coverage over the wild type, expressed as mass of extractable cuticular lipids per surface area (Table 3).

TABLE 3

Composition of cuticular wax on leaves of wild type and shn.

| | Wild type WS [µg/cm$^2$] | Mutant shn [µg/cm$^2$] | Average fold increase |
|---|---|---|---|
| Fatty acids | 0.13 ± 0.02 | 0.50 ± 0.30 | 3.8 |
| Aldehydes | 0.05 ± 0.03 | 0.11 ± 0.12 | 2.2 |
| prim. Alcohols | 0.18 ± 0.03 | 0.50 ± 0.28 | 2.8 |
| Alkyl esters | tr* | 0.07 ± 0.05 | 1.4 |
| Alkanes | 0.23 ± 0.06 | 2.08 ± 1.38 | 9.0 |
| sec. Alcohols | tr | 0.10 ± 0.03 | 11.9 |
| Ketones | 0.01 ± 0.01 | 0.11 ± 0.08 | 11.0 |
| Steroids | 0.08 ± 0.05 | 0.34 ± 0.27 | 4.3 |
| Isoalcohols | 0.05 ± 0.04 | 0.11 ± 0.09 | 2.2 |
| Unidentified | 0.07 ± 0.07 | 0.84 ± 0.77 | 12.0 |
| Total | 0.80 ± 0.26 | 4.78 ± 2.35 | 6.0 |

Coverages of total extracted lipids and of individual compound classes are given as mean values with standard deviation.
*traces, i.e. less than 0.05 µg/cm$^2$ detectable.

Wild type leaf wax was found to contain approximately equal amounts of compounds from the acyl reduction pathway (primary alcohols, alkyl esters) and from the decarbonylation pathway (alkanes, secondary alcohols, ketones). In sharp contrast, the shn mutant wax was characterized by differences in amounts of compounds resulting from both pathways. While primary alcohols and alkyl esters showed only 2.8- and 1.4-fold increases, the alkanes, secondary alcohols and ketones were increased by 9.0-, 11.9- and 11.0-fold, respectively. Aldehydes, regarded as intermediates of the decarbonylation pathway, showed 2.2-fold higher levels in the mutant wax mixture. Similarly, other compound classes (fatty acids, branched alcohols and steroids) were also found at elevated levels in the mutant wax, albeit only with moderate increases.

In both wild type and mutant leaf waxes the fatty acids, aldehydes and primary alcohols were dominated by constituents with even carbon numbers, as expected for acyl derivatives resulting from C2 elongation cycles (FIG. 1). The alkanes, secondary alcohols and ketones showed a clear preponderance of odd-numbered representatives, typical for metabolites from the elongation/decarbonylation route. The wild type wax showed chain length distributions dominated by C32/C34 for fatty acids and aldehydes, by C31 for alkanes, and by C26/C28 for primary alcohols. Only C29 secondary alcohol and ketone, with functional groups both in the C14 and C15 position, could be detected. As compared to these wild type patterns, the mutant leaf wax contained much higher concentrations of C30 fatty acid, C30 aldehyde and C27/C29 alkanes, compensating for lower relative amounts of C34 fatty acid, C34 aldehyde and C33 alkane, respectively (FIG. 1). The chain length distribution of secondary alcohols, ketones, and primary alcohols were similar in the wild type and the mutant.

Example 4

Alterations to Cuticle Permeability in the shn Mutant

To investigate whether the shn cuticular membrane properties were altered a chlorophyll leaching experiment was conducted in which rosette leaves from both shn and wild type plants were submerged in 80% ethanol for different time periods and the chlorophyll concentration in the solution was determined. Chlorophyll was extracted much faster from leaves of shn leaves as compared to wild type (FIG. 2A) and therefore the higher elution of chlorophyll from shn leaves indicates an increase in cuticle permeability.

To assay cuticular water loss, fresh weight changes of detached rosettes were monitored. Roots and emerging inflorescence stem of four-week old seedlings were detached from the rosettes, which were used to examine loss of water over time. The results (FIG. 2C) show that fresh weight loss from the rosette tissues was increased in shn when compared to wild type rosette tissues. As this water loss in shn continues beyond the time when stomata close (Yoshida et al., 2002, Plant Cell Physiol. 43, 1473-1483), it is the increased cuticular water loss in shn that is revealed.

Example 5

A Member of the AP2/EREBP Transcription Factor Family is Responsible for the shn Mutant Phenotype DNA gel blot analysis showed that shn contains a single insertion (data not shown). Isolation and sequence analysis of DNA flanking the insertion site further indicated that the insertion is located in an intergenic region on chromosome 1. The location of the 35S enhancer tetramer is between a gene encoding an unknown protein (4025 base pairs upstream of the promoter) and a gene encoding a member of the plant specific AP2/EREBP family of transcription factors (620 base pairs upstream of the promoter). To examine if these two genes were induced in expression in shn compared to wild type, we conducted a Reverse Transcription PCR (RT-PCR) experiment using cDNA isolated from shn and wild type leaf tissues. The results showed that the genes from both sides of the 35S enhancer tetramer were induced in the shn mutant leaves compared to wild type leaves (data not shown).

Example 6

Transgenic Plants Overexpressing SHN1

The downstream gene (At1g15360), encoding the AP2/EREBP transcription factor, was chosen as primary candidate determining the shn mutant phenotype. Consequently, the coding region of the gene (termed SHINE1 or SHN1) was cloned and constitutively expressed in *Arabidopsis* under the control of the 35S CaMV promoter. In fact, all the transgenic plants raised (20 individuals) showed a phenotype resembling the original activation tag line, in particular the shn brilliant green leaf and silique surface and downward curling of the leaves (data not shown). The phenotype of most of the 35S::SHN1 lines (both primary transformants and subsequent generations) was more severe compared to the original shn mutant. In most cases plants were smaller, and in some cases even dwarfed (3 to 5 cm in size upon maturity), and their leaves were very strongly curved, even rolled (data not shown). Further chemical analyses showed that the transformant leaves had cuticular wax load, relative compositions of compound classes, and chain length distributions within these classes similar to the original shn tag mutant.

In contrast to the activation tag shn mutant, flower morphology was also affected, particularly in petals which were folded and in part "hidden" in-between the sepals and the flower interior organs (data not shown). Scanning electron microscopy was used to investigate the surface petals derived from the SHN1 overexpressing lines (data not shown). The anterior and distal parts of the adaxial surface of wild type *Arabidopsis* petals normally show a uniform spread of conical epidermal cells, which exhibit a typical cuticular ornamentation (data not shown). On the other hand, in shn petals one could identify a mix of both typical, conical cells and much longer cells, often more than doubled in size.

The number and structure of trichomes was analysed in the first true leaves of 35S::SHN1 seedlings compared to wild type. The adaxial side of the first true leaf of wild type (ecotype Wassilewskija) contained approximately 25 of mainly triple-branched trichomes, spread on its surface. In contrast, the first true leaves of 35S::SHN1 seedlings contained much lower numbers of trichomes, ranging from leaves with no trichomes at all up to a maximum of 8-10 trichomes (data not shown). When trichomes were present on the first leaves of 35S::SHN1 they were nearly all single-branched and located on leaf blade margins. The same observations were also detected in leaves derived from older plants.

Two other features of epidermal cell differentiation were also altered by the overexpression of SHN1. Both pavement cell density and stomatal density on the abaxial side of the 35S::SHN1 lines were reduced compared to wild type leaves (see Table 4). Calculating the stomatal index revealed that it was reduced by 41% in the 35S::SHN1 leaves compared to wild type (Table 4).

TABLE 4

Stomatal Density, Pavement Cell Density and Stomatal Index of Mature shn and Wild-type Rosette Leaf Blades

| | Stomatal Density (cells/mm² ± SD) | Pavement Cell Density (cells/mm² ± SD) | Stomatal Index |
|---|---|---|---|
| Wild-type | 27.03 ± 9.63 | 80.16 ± 19.88 | 25.22 ± 4.48 |
| 35S::SHN1 | 8.91 ± 3.76 | 51.56 ± 15.35 | 14.73 ± 3.96 |

Figure 2B:
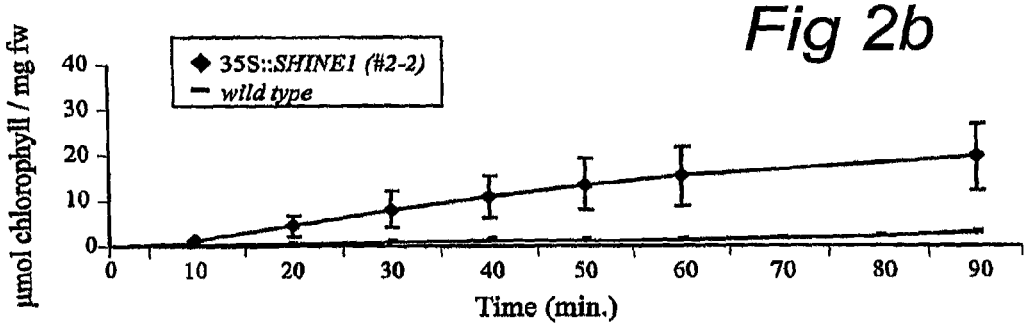
Figure 2C:
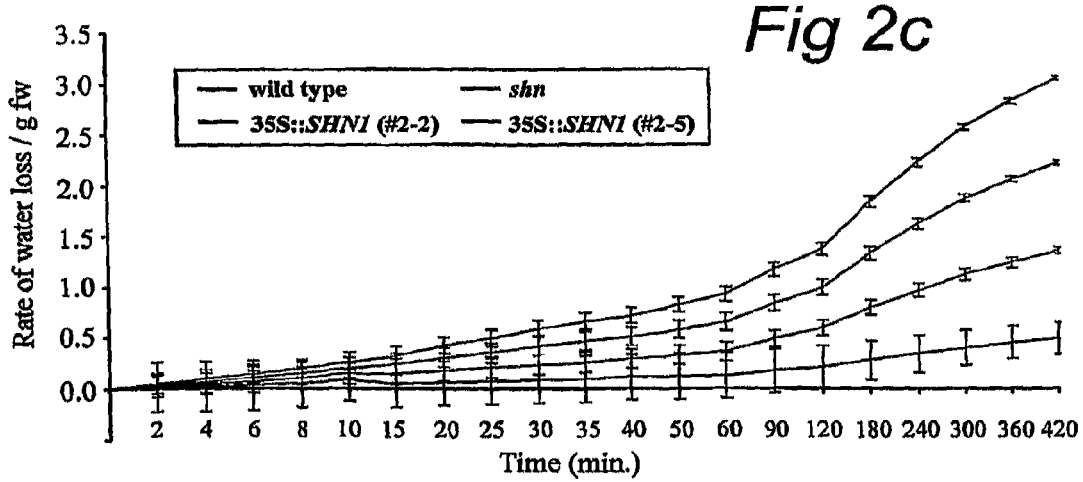

Leaching assays with progeny of two 35S::SHN1 primary transformants (#2-2 and #2-5) showed that their cuticle was more permeable to ethanol, since chlorophyll could be extracted easier (FIG. 2B). In line with the overall stronger phenotype of the 35S::SHN1 lines, the difference in chlorophyll leaching compared to wild type leaves was more dramatic than initially observed for the activation tag shn mutant. The two 35S::SHN1 primary transformants (#2-2 and #2-5) showed also an increased rate of water loss compared to wild type (FIG. 2C).

Example 7

Overexpression of Two Other Members of the SHINE Clade Results in Similar Phenotype The plant AP2/EREBP super-family of transcription factors contains 141 members in *Arabidopsis* (Alonso et al., 2003, Science 301, 653-657). Sequence homology searches and phylogenetic analysis across the entire AP2/EREBP family showed that SHN1 is part of a small, distinct group of four proteins, 199, 189, 186 and 205 amino acid residues long (SHN1, SHN2, SHN3 and OsSHN1 respectively; FIG. 3).

They contain the highly conserved AP2 domain and share two other conserved motifs in their central portion ("mm", positions 87 to 147 in FIG. 3) and C-termini ("cm", positions 189 to 198 in FIG. 3). The At5g25190 protein is more distant in sequence from SHINE proteins.

The genomic regions encompassing the coding regions of SHN2 and SHN3 were used for overexpression (using the double-enhanced 35S CaMV promoter) of both genes in *Arabidopsis* plants. Interestingly, plants overexpressing SHN2 and SHN3 showed an identical phenotype to the one obtained when overexpressing the SHN1 gene (data not shown).

Example 8

Spatial and Temporal Expression of the SHN Clade Members

In order to examine the expression of SHN1, SHN2 and SHN3 three plant transformation constructs were generated, which linked 2.0-kb DNA sequences upstream of the predicted ATG codon of each gene to the β-glucuronidase (GUS) reporter gene. In general GUS expression was detected in most plant organs, in some cases overlapping patterns were detected while in others very specific expression was evident in certain cell layers.

SHN1 expression was detected in the inflorescence and root tissues, but not in stem, rosette or cauline leaves (data not shown). Expression could be detected in sepals of very young closed buds (stage 6; Smyth et al., 1990, Plant Cell 2, 755-767), and later at stage 10. At that time, expression could also be detected in petals and developing gynoecium, but not in stamens. In petals and sepals, veins were stained stronger than the rest of the organ, in which it was restricted to the epidermis. At anthesis (stage 13) the expression of SHN1 was reduced in the gynoecium, commenced in the anther and showed weaker expression in the anther filament. When petals and sepals withered (stage 16), strong expression could be detected at the bottom of the silique, in the abscission zone and in the pedicel region below it, while later, at silique maturity, it was detected in the same region, but only at the nectaries. Additional GUS expression was observed at the branch points of pedicels of most young flowers in the inflorescence, in small lateral inflorescences (including the small bract adjacent to them), and in a patchy pattern in roots of mature plants and very young leaves in the rosette, including support cells of their trichomes.

The SHN2 gene shows a pattern of expression associated with anther and silique dehiscence. At stage 12, when petals level with long stamens and tapetum degeneration is initiated in the anther (stage 10 of anther development; Sanders et al. 1999, Sexual Plant Rep. 11, 297-322), expression could be detected in the stomium region. Up to anthesis, during which the septum is degenerated, a bilocular anther is formed, the stomium splits and pollen is released, expression of SHN2 became more specific to the dehiscence zone and continued until stamens fell off the senescing flower (data not shown). Subsequently, when petals and sepals withered (stage 16), GUS expression could be detected as an intense spot at the bottom of each valve. One stage later, i.e. in the growing phase of the green silique as it reached final length and the dehiscence zone differentiated, SHN2 was strongly expressed along the valve margin-replum boundary, the region where pod shatter occurs, allowing seed dispersal.

The SHN3 gene was most broadly expressed and was active in all plant organs. It showed expression in the vasculature and in the lateral root tip (data not shown). When staining young 10 day-old seedlings, expression was detected in the support cells of trichomes present on the most newly formed leaves. In older leaves (rosette) as well as in cauline leaves, SHN3 was mainly expressed in the central vein with lower expression in the entire blade. It was not expressed in a uniform manner in stems, showing mostly weak epidermal expression. Expression of SHN3 in the inflorescence and young rosette leaves overlapped to a large extent with that observed for SHN1 (see above). Most interestingly, it showed an organ-specific wound induction. While wounding did not induce it in rosette leaves, it did activate it in cauline leaves, stems and siliques.

Example 9

Plants Overexpressing SHN1 show Enhanced Drought Tolerance

In order to examine to what extent the change in plant surface, as a result from SHN1 over-expression, affected its drought tolerance capacity. To do so, 15 day-old seedlings of the original activation tag lines, two of the 35S::SHN1 transformant lines (lines #2-5 and #2-2) and wild type (ecotype Wassilewskija) were exposed to a period of 9-11 days of dehydration (FIG. 4). Subsequently, seedlings were watered and their recovery monitored for a week. While wild type plants did not recover from the dehydration treatments longer than 9 days and completely dried out, all seedlings derived from lines expressing the SHN1 gene recovered to become greener and stronger. Consistent with the phenotype characteristics described above, seedlings derived from the activation tagged line were relatively weak in recovery when compared to the two transgenic 35S::SHN1 lines.

Similarly, overexpression of SHN1 in rice also leads to plants with an increased drought tolerance. Transformants with a 35S::SHN1 construct are able to withstand prolonged leaf wilting under water deprivation compared to control plants, as assessed by recovery following rehydration. See also further Example below.

Example 10

Plants Expressing the SHN-EAR Fusion Show Loss of Function

Transgenic plants expressing the SHN-EAR repressor fusions were generated by transformation. Transgenic plants expressing either SHN1-EAR, SHN2-EAR or SHN3-EAR displayed similar loss of function phenotypes, as expected for redundant genes coding for proteins having similar DNA binding and protein interaction properties. Expression of the SHN-EAR under specific promoters could specify the loss of function to a specific tissue, e.g. conferring non-dehiscence of anthers or reduced podshatter. See also further Examples below.

Example 11

Overexpression of the Rice OsSHINE Gene in *Arabidopsis* Reveals a Conserved Function In comparison of the amino acid sequences of the three similar *Arabidopsis* SHN-related proteins, high similarity was found in the central portion (middle 'mm') and C termini ('cm') as well as the AP2 DNA-binding domains. Using these consensus domains ('mm', 'cm' and 'AP2') to screen the sequence databases, members of the SHN clade of proteins could be defined as those that show high similarity to the Arabidopsis SHN proteins in these conserved domains. We searched the rice genome database for proteins with amino acid sequences similar to the SHN protein conserved regions, and found two genomic clones with predicted amino acids that showed high homology in these conserved regions (accession number BAD15859 and BAD35470). We named these two genes OsSHN1 and OsSHN2. OsSHN1 and OsSHN2 contained an open reading frame of 206 and 244 amino acids, respectively, with an amino acid sequence of 205 and 243 amino acids (SEQ ID NO: 14 and SEQ ID NO: 24). These proteins are 42.3-62.4% similar to the *Arabidopsis* proteins and 68.3% similar to each other.

Fragments encompassing the full length coding region and the upstream region of OsSHN1 were amplified (using pfu DNA polymerase) from young leaf genomic DNA of rice cv. Nipponbare. Oligonucleotides OsSHN1F (5'-AATAAG-GATCCATGGTACAGCCAAAGAAG-3') and OsSHN1R (5'-AATAAGTCGACTCAGATGACAAAGCTACC-3') were used to amplify 0.76 kb fragment containing the full length coding region of OsSHN1. The pair of oligonucleotides introduced BamHI and SalI restriction sites to the amplified fragments at their 5' and 3', respectively, which were utilized for ligation. In all cases fragments were A-tailed and introduced to the pGEM-T Easy vector as described by the manufacturer (Promega) and subsequently sequenced from both sides before digestion and ligation to the binary vector. The overexpression and chimeric repressor constructs were assembled by multi-point ligations, in which the individual fragments (promoter, OsSHN1 gene, terminator) with appropriate compatible cohesive ends were ligated together to the binary vector in one reaction. A CaMV35S promoter fragment extending from −526 to the transcription start site, was obtained as a 0.55 kb HindIII-BamHI fragment from a pBS-SK+ derivative of pDH51 (Pietrzak et al., 1986). A CaMV35S terminator fragment was obtained as a 0.21 kb SalI-EcoRI fragment from a pBS-SK+ derivative of pDH51 Pietrzak et al., 1986). The construct was made in the binary vector pMOG22 (ZENECA-MOGEN, NL) which contains a chimaeric CaMV 35S-hygromycin phosphotransferase-tNos for selection during transformation. PCR, restriction digestions, plasmid DNA isolation and gel electrophoresis were performed using standard protocols. The constructs were introduced into the plants using the floral dipping transformation method (Clough and Bent, 1998). The seeds were plated on one-half-strength Murashige and Skoog medium (½MS; Murashige and Skoog, 1962) and 15 sucrose. Seedlings selected on 20 mg/L hygromycin were subsequently transferred to the greenhouse.

All plants were grown in the greenhouse at around 22° C. and were in the *Arabidopsis* ecotype Wassilewskija (Ws). For the drought tolerance experiments, soil mixture comprised 1 part of sand and perlite and 2 parts of compost [a mixture made up of 25% clay and 75% turf with EC=1 (NPK); Hortimea, Netherlands]. Seeds were sown (after 3 nights at 4° C.) at density of six plants per 4 cm pot in a tray with 51 pots (Aracon containers, BetaTech, Belgium). Nutrients (Hydroagri, Rotterdam, The Netherlands; 2.6 EC) were supplied 10 days after germination and at two weeks after germination the plants were subjected to drought (for 13, 14, 15 or 16 days) by transferring the pots to dry trays (after drying each pot from outside). Every 2 days in drought, the plants were moved within the tray to nullify pot position effects. Subsequently, plants were rehydrated and observed for recovery after one week. Experiment was conducted to compare drought tolerance between wild-type and 35S::AtSHN1(#2-2), 35S::OsSHN1(#1) and 35S::OsSHN1(#16) plants.

Plants overexpressing OsSHN1 showed an identical visual phenotype to the one obtained when overexpressing the *Arabidopsis* SHN1 gene, including the brilliant, shiny green color of both rosette and cauline leaves, leaf curling, and altered silique length.

To investigate whether the cuticular membrane properties of OsSHN1 overexpressor were altered, we conducted a chlorophyll leaching experiment in which rosette leaves from both OsSHN1 overexpressor and wild-type plants were submerged in 80% ethanol for different time periods, and the chlorophyll concentration in the solution was determined. Chlorophyll was extracted much faster from leaves of OsSHN1 overexpressor as compared with the wild type; therefore, the higher elution of chlorophyll from OsSHN1 overexpressor indicates an increase in cuticle permeability to organic solvents.

We tested whether two other features of epidermal cell differentiation were also altered by overexpression of OsSHN1. Both pavement cell density and stomatal density on the abaxial side of the OsSHN1 overexpressor was reduced compared with wild-type leaves. Calculating the stomatal index revealed that it was reduced by 40% in the OsSHN1 overexpressor leaves compared with the wild-type (Table 5).

TABLE 5

Stomatal Density, Pavement Cell Density, and Stomatal Index of Mature 35S::OsSHN1 and Wild-Type Rosette Leaf Blades

| Plant line | Stomatal Density (cells/mm² ± SD) | Pavement Cell Density (cells/mm² ± SD) | Stomatal Index |
|---|---|---|---|
| Wild Type | 25.39 ± 3.59 | 83.20 ± 10.13 | 30.55 ± 2.88 |
| 35S:OsSHN1 | 10.94 ± 3.61 | 59.38 ± 9.41 | 18.16 ± 4.52 |

To investigate whether the OsSHN1 has the same downstream target genes as that as the *Arabidopsis* SHN1 we conducted RT-PCR for the CER1 gene using leaf rosette RNA samples from both the OsSHN1 overexpressor and wild-type plants. We found that the CER1 gene was significantly overexpressed in the 35S-OsSHN1 plants.

The *Arabidopsis* transformants overexpressing the OsSHN1 gene were used in a pot assay for drought tolerance as described above. Whereas wild-type plants did not recover from the dehydration treatments longer than 13 days and completely dried out, all seedlings derived from lines expressing the OsSHN1 gene recovered after rehydration to become greener and stronger. The drought tolerance revealed in this test is equivalent to that shown by the *Arabidopsis* SHN1 gene.

Over-expression of the SHN1 in transgenic *Arabidopsis* plants resulted in higher tolerance to drought, probably related to the reduced stomatal density. Over-expression of OsSHN1 in transgenic *Arabidopsis* also enhanced drought tolerance. It is probable that the reduction in the number of stomata that we also found in the OsSHN1 overexpressors is responsible for this drought tolerance. But we also found that overexpression of OsSHN1 induced expression of rd22, a gene responsive to dehydration stress (Yamaguchi-Shinozaki and Shinozaki, 1993), as detected by RT-PCR This indicated that another mechanism is probably also involved in enhancement of drought tolerance in OsSHN1 overexpressor. In our microarray data, rd22 is one of many abiotic stress-inducible genes up-regulated in transgenic 35S::SHN1 *Arabidopsis* (unpublished data).

Example 12

Overexpression of the *Arabidopsis* SHINE Gene in Rice Confers Drought Tolerance The SHINE overexpression construct for rice transformation was assembled by multi-point ligation, in which the individual fragments (promoter, AtSHN2 gene, terminator) with appropriate compatible cohesive ends were ligated together to the binary vector in one reaction. A CaMV35S promoter fragment extending from −526 to the transcription start site, was obtained as a 0.55 kb HindIII-BamHI fragment from a pBS-SK+ derivative of pDH51 (Pietrzak et al., 1986). The full length coding region of AtSHN2 was obtained as BamHI-NotI fragment from Aharoni et al. (2004). A CaMV35S terminator fragment was obtained as a 0.21 kb NotI-EcoRI fragment from a pBS-SK+ derivative of pDH51 (Pietrzak et al., 1986). The construct was made in the binary vector pMOG22 (ZENECA-MOGEN, NL) which contains a chimaeric CaMV 35S-hygromycin phosphotransferase-tNos for selection during transformation.

*Agrobacterium*-mediated transformation of *Oryza sativa* ssp. *japonica* cv. Nipponbare, plant regeneration and growth were performed following as described in Greco et al. (2001). The *Agrobacterium* strain AGL-1 was used for transformation. For growing progeny seeds, the seeds were dehusked, surface-sterilized (1 min in 70% ethanol, followed by 20 min in 1% NaOCl, and four rinses with sterile water) and sown on 50 mg/l hygromycin in sterile MQ water. Plants were grown in a climate chamber under long-day conditions (16 h light, 8 h dark, 280C) for about two weeks, before being transferred to the greenhouse.

Transformation of rice yielded fifteen independent transgenic lines. None of the rice transformants revealed any obvious leaf wax increase or plant leaf phenotype, unlike that observed in *Arabidopsis*. RT-PCR analysis, however, confirmed high level expression of the SHN2 gene. Lines with high expression and enough seed were used for further experimentation.

We tested whether other features of epidermal cell differentiation were also altered by the overexpression of SHN2. Stomatal density on the abaxial side of the 35S::SHN2 leaves was reduced to ¾th compared with wild-type leaves (Table 6).

TABLE 6

|  | Stomatal Density (cells/mm$^2$ ± SD) |
| --- | --- |
| Wild Type | 40.62 ± 3.61 |
| Transgenic | 29.69 ± 3.12 |

A Drought resistance experiment was conducted with 35S::SHN2 lines and the wild type. For this 14 days old seedlings (5 seedlings per pot) of either wild-type or 35S::SHN2 lines were exposed to dehydration stress by withholding water for 9 days. At this stage the wild-type were wilted completely while the 35S-SHN2 lines were still green and had water. The seedlings were then watered and their appearance noted after a week. There was a clear difference between wild-type and 35S::SHN2, in which there is 100% recovery of the overexpression line which turned into light green and no recovery of the wild-type was visible.

The above results showed that all rice transformants reveal no obvious leaf wax increase or modified plant phenotype. Thus, overexpression of SHINE in rice does not increase the leaf epicuticular wax or induce downstream target genes involved in epcuticular wax biosynthesis. Neither does it cause a change in leaf morphology like curling. However overexpression does cause a change in cuticular and epidermal properties, like permeability and reduction in stomatal density. In other words the expression of SHINE in rice is able to dissect and distinguish between the epidermal and cuticular changes from the epicuticular wax changes.

As some monocots like rice have very low wax and as no changes in epicuticular wax were found in SHINE overexpressing plants, it was very surprising to find that SHINE overexpression resulted in drought tolerant monocot plants. This example clearly showed that wax synthesis is not required for generating drought tolerant plants and that the SHINE clade genes can, therefore, be also used to generate drought tolerant plants without an alteration of the epicuticular wax layers and may, therefore, also be used to generate drought tolerance without modifying the epicuticular wax layer or properties, e.g. in plants or plant organs which have very low or no epicuticular wax (e.g. monocots like rice). The alteration in epicuticular wax appears, thus, to be a phenotype which is irrelevant with respect to generating drought tolerance and it is only the change in the epidermal and cuticular properties which are effective in generating drought tolerance in plants.

The drought resistance is, therefore, not dependent on the leaf epicuticular wax and thus epicuticular wax and the leaf phenotype do not need to be modified in order to provide drought resistance in crop plants.

Example 13

Overexpression of the *Arabidopsis* SHINE Genes Shows Salinity Tolerance in *Arabidopsis* and Rice To conduct a Salinity Tolerance assay, the *Arabidopsis* plants overexpressing the SHINE gene (35S-SHN1) and appropriate wild-type controls were grown in the greenhouse at ~22° C. For salt tolerant assays, plants were grown in potting soil (Hortimea, Elst, The Netherlands). Seeds were sown (after three nights at 4° C.) at density of 1-2 plants per 4-cm pot in a tray with 51 pots (Aracon containers; BetaTech, Gent, Belgium). Nutrients (Hydroagri, Rotterdam, The Netherlands; 2.6 EC) were supplied 2 weeks after germination, and after 3 weeks of germination the plants were subjected to 300 mM NaCl solution at the interval of 3 days for three applications and subsequently monitored for bleaching for the next 2 weeks. Photographs were taken and survival rates were counted on the 10th day after third application of NaCl. The experiment was repeated three times.

The 35S-SHN1 line showed enhanced salt tolerance compared to its wild type (WI), ecotype Ws. The WT plant gradually bleach out and do not survive approximately 1 week under salt stress, whereas 35S-SHN1 not only survives the salt stress but is also able to function normally (Table 7).

TABLE 7

| Percent survival rate in 300 mM salt treated plants | | |
| --- | --- | --- |
|  | No. of plants tested | % survival |
| Ws | 20 | 15 |
| 35S-SHN1 | 20 | 85 |

Samples were collected from the NaCl treated plants and the non-treated plants. There FW's (fresh weight) were measured immediately after harvesting and samples were dried for 5 days at 65° C. in an oven and later there DW's (dry weights) were measured. The samples were then used for analysis of sodium (Na+), calcium (Ca+) and potassium (K+) content. About 15 to 50 mg of dry material was digested with 1 ml of the digestion mixture (sulphuric acid-salicylic acid and selenium) and 2 carborundum beads and swirled carefully until all the plant material was moistened and treated overnight. Temperature was increased gradually in small steps to about 330° C. and later on cooling 0.1 ml of hydrogen peroxide was added and heated again. This step was repeated 3 times until the digest had turned colorless. On cooling down to room temperature 5 ml of demi-water was added to make up to the mark and left overnight. The Na+ Ca+ and K+ Ion Content were determined by using an Atomic Emission Spectrophotometer (Elex, Eppendorf, Hamburg, Germany).

TABLE 8

Mineral Analysis

| Sample Nr. | Na mmol/kg | K mmol/kg | Ca mmol/kg |
|---|---|---|---|
| Non-treated | | | |
| WT | 55 ± 3 | 1249 ± 42 | 578 ± 19 |
| 35S-SHN1 | 61 ± 6 | 1093 ± 105 | 626 ± 58 |
| Treated | | | |
| WT | 4882 ± 960.74 | 534 ± 63.09 | 410 ± 0.45 |
| 35S-SHN1 | 4940 ± 796.09 | 716 ± 27.72 | 657 ± 73.72 |

Na+, Ca+ and K+ contents were measured and their standard errors measured based on two independent experiments.

The analysis shows that under non-treated conditions both 35S-SHN1 and WT shows no difference in the content of Na+, Ca+ and K+(Table 8), however some of these components were found to be altered under salt stress conditions. Salt treated 35S-SHN1 and WT showed increased accumulation of Na+ compared to the non treated plants and this increase in Na+ accumulation was found to be the same in WT and 35S-SHN1. The level of K+ was decreased both in 35S-SHN1 and WT, however this decrease was found to be significantly more in WT compared to the 35S-SHN1. The levels of Ca+ was decreased in salt treated WT compared to the non treated WT whereas it was maintained in salt treated 35S-SHN1 compared to non treated.

The results indicate that under salt stress condition the 35S-SHN1 is able to maintain its calcium levels, which in turn helps to maintain the level of K+ in the plant by enhancing the selectivity of the root K+ transport system (Lauchli, 1990). It is known that calcium is one of the important factors which are involved in the regulation of K+/Na+ selectivity of K+ transport during NaCl stress (Lauchli, 1990).

Microarray results of 35S-SHN1 showed induction of calcium binding proteins like Calreticulin 3 (CRT3), Calnexin 1 (CNX1), Calreticulin 2 (CRT2). In addition genes involved in stress responses like LEA3 (late embryogenesis abundant), RD22 and Protein kinase family proteins. This indicates that overexpression of SHINE triggers a signal which results in overexpression of calcium binding genes, which then activates the transport system that has higher affinity for the selectivity of K+ over Na+ in salt stress condition (Liu & Zhu, 1997).

Example 14

A Dominant Negative Mutant Using a SHINE-EAR Repressor Fusion Displays Loss of Function with Reduction in Stem Wax. Change in Inflorescence Phenotype and Siliques with Reduction in Shattering Dominant Negative Mutant Phenotypes Using a SHINE Repressor Fusion Protein Mutant Phenotypes: Reduction in Stem Wax, Change in Inflorescence Phenotype and Siliques with Reduction in Shattering.

To assess the role of the SHINE genes by making a loss of function mutant, we modified the SHINE protein to be a chimeric repressor (SHN-SRDX) by fusing it to the EAR repression domain (Hiratsu et al., 2003) and overexpressed it in *Arabidopsis*. Other studies using RNAi constructs of the *Arabidopsis* SHN genes did not reveal mutant phenotypes, therefore this alternative option was taken to avoid functional redundancy. We made constructs with both the *Arabidopsis* and rice SHINE genes that showed similar results, however the example of the rice SHN gene will be demonstrated here.

To make the dominant repressor SHINE-EAR gene fusion construct, PCR fragments were isolated using specific primers. Fragments encompassing the full length coding region and the upstream region of OsSHN1 were amplified (using pfu DNA polymerase) from young leaf genomic DNA of rice cv. Nipponbare. Oligonucleotides OsSHN1F (5'-AATAAG-GATCCATGGTACAGCCAAAGAAG-3') and OsSHN1::SRDXR
(5'-CGTCGACTCAAGCGAAACCCAAACG-GAGTTCTAGATCCAGATCCAGGA TGACAAAGCTAC-CCTCTCCCTCTC) were used to amplify 0.8 kb fragment containing chimeric fusion of the full length coding region of OsSHN1 and SRDX (LDLDLELRLGFA) at the 3' end. Oligunucleotide OsSHN1::SRDXR introduced a SalI restriction site to the amplified fragment at its 3' and OsSHN1F introduced an BamHI restriction site at the 5' end of the fragment. The introduced BamHI and SalI restriction sites to the amplified fragments at their 5' and 3', respectively, were utilized for ligation. In all cases fragments were A-tailed and introduced to the pGEM-T Easy vector as described by the manufacturer (Promega) and subsequently sequenced from both sides before digestion and ligation to the binary vector. The overexpression and chimeric repressor constructs were assembled by multi-point ligations, in which the individual fragments (promoter, OsSHN1::SRDX gene, terminator) with appropriate compatible cohesive ends were ligated together to the binary vector in one reaction. A CaMV35S promoter fragment extending from −526 to the transcription start site, was obtained as a 0.55 kb HindIII-BamHI fragment from a pBS-SK+ derivative of pDH51 (Pietrzak et al., 1986). A CaMV35S terminator fragment was obtained as a 0.21 kb SalI-EcoRI fragment from a pBS-SK+ derivative of pDH51 (Pietrzak et al., 1986). The construct was made in the binary vector pMOG22 (ZENECA-MOGEN, NL) which contains a chimaeric CaMV 35S-hygromycin phosphotransferase-tNos for selection during transformation. PCR, restriction digestions, plasmid DNA isolation and gel electrophoresis were performed using standard protocols. The constructs were introduced into the plants using the floral dipping transformation method (Clough and Bent, 1998). The seeds were plated on one-half-strength Murashige and Skoog medium (1/2MS; Murashige and Skoog, 1962) and 15 sucrose. Seedlings selected on 20 mg/L hygromycin were subsequently transferred to the greenhouse.

Forty-five primary transformants were generated from the transformation experiments. From these, eighteen primary transformants showed a loss-of-function mutant stem phenotype with reduced epicuticular wax (glossy green stem). Some of the primary transformants did not set seed showing very short empty siliques indicating sterility. Some of the sterile primary transformants were covered in a plastic bag for a few days during flowering and showed good seed set, indicating a conditional male semi-sterile phenotype as is seen for some *Arabidopsis* cer mutants lacking wax in the pollen coat (Aarts et al., 1995).

We also found some primary transformants had flat siliques that is due to change in structure of the silique replum and valves making the silique more extended laterally. The glossy green stem phenotype was not very obvious on primary transformants transferred to the greenhouse from selection media primarily due to the thin stem structure. The T2 progeny, however, revealed the glossy thinner stems inherited as a dominant allele (about ¾ progeny). The OsSHN1-SRDX overexpressors also showed smaller rosette leaves and shorter siliques in the progeny.

To prove that downregulation of CER1 transcript is responsible for the glossy 'cer' stem phenotype we conducted RT-PCR for the CER1 gene using stem RNA samples from both 35S:OsSHN1-SRDX and wild-type plants. We found that CER1 gene was significantly repressed in the 35S:OsSHN1-SRDX plants.

The phenotype of the SHN-repressor plants reveal the role of the different SHN genes in *Arabidopsis*. The glossy 'cer' stem is probably due to repression of the Epicuticular wax pathway leading to reduction in stem wax. The short siliques are due to conditional pollen sterility, due to lack of a wax coat requiring high-humidity for making the pollen fertile and thus seed formation in the silique. The change in flower inflorescence structure reflects the expression pattern of the *Arabidopsis*. SHN1 and SHN3 that are probably required for function in this tissue. The flat silique shape is indicative of the expression of the AtSHN2 that is expressed in the valve margin, alteration or malfunction of this layer cell separation layer inhibits silique opening and shattering. Thus SHN proteins are required for opening or shattering of the silique or pod.

REFERENCES

Aarts M G M, Keizer C J, Stiekema W J and Pereira A (1995) Molecular characterization of the CER1 gene of *Arabidopsis* involved in epicuticular wax biosynthesis and pollen fertility. Plant Cell 7: 2115-2127

Clough S J and Bent A F (1998) Floral dip: a simplified method for *Agrobacterium*-mediated transformation of *Arabidopsis thaliana*. Plant J 16(6): 735-743

Greco R, Ouwerkerk PBF, Taal A J C, Favalli C, Beguiristain T, Puigdoménech P, Colombo L, Hoge J H C and Pereira A (2001) Early and multiple Ac transpositions in rice generated by an adjacent strong enhancer. Plant Mol Biol 46: 215-227

Hiratsu K, Matsui K, Koyama T, Ohme-Takagi M (2003) Dominant repression of target genes by chimeric repressors that include the EAR motif, a repression domain, in *Arabidopsis*. Plant J 34(5): 733-739

Läuchli, A. (1990) in Calcium in Plant Growth and Development, eds. Leonard, R. T., Hepler, P. K. & The American Society of Plant Physiologists Symposium Series (American Society of Plant Physiologists. Rockville, Md.), Vol. 4, pp. 26-35.

Liu, J and Zhu, J-K (1997) An *Arabidopsis* mutant that requires increased calcium for potassium nutrition and salt tolerance. Proc Natl Acad Sci USA. 94:14960-4.

Murashige T and Skoog F (1962) A revised medium for rapid growth and bioassays with tobacco tissue cultures. Physiol Plant 15: 473-497

Pietrzak M, Shillito R D, Hohn T, Potrykus I (1986) Expression in plants of two bacterial antibiotic resistance genes after protoplast transformation with a new plant expression vector. Nucleic Acids Res 14(14): 5857-5868

Yamaguchi-Shinozaki K, Shinozaki K (1993) The plant hormone abscisic acid mediates the drought-induced expression but not the seed-specific expression of rd22, a gene responsive to dehydration stress in *Arabidopsis thaliana*. Mol Gen Genet. 238(1-2): 17-25

The invention claimed is:

1. A transgenic monocotyledonous plant of the genus *Oryza* comprising a chimeric gene, integrated in its genome, which chimeric gene comprises a transcription regulatory sequence active in plant cells operably linked to a nucleic acid sequence encoding a SHN protein that comprises the sequence SEQ ID NO:15, wherein said plant possesses enhanced drought tolerance without modification of its epicuticular wax layer.

2. The plant according to claim 1, wherein said SHN protein further comprises the sequence SEQ ID NO:16.

3. The plant according to claim 1, wherein said transcription regulatory sequence is selected from the group consisting of: a constitutive promoter, an inducible promoter, a tissue-specific promoter and a developmentally-regulated promoter.

4. The plant according to claim 1, wherein the sequence of the SHN protein is selected from the group consisting of SEQ ID NO:11, SEQ ID NO:12, SEQ ID NO:13, SEQ ID NO:14 and SEQ ID NO:24.

5. A seed or a fruit of a plant according to claim 1, which seed or fruit comprises said chimeric gene.

6. A method of generating a transgenic plant according to claim 1, comprising introducing and expressing in a monocotyledonous *Oryza* plant a nucleic acid sequence encoding said SHN protein, thereby generating said plant.

7. The transgenic monocotyledonous plant of claim 1 which is of the species *Oryza sativa*.

8. The method according to claim 6 wherein the plant is of the species *Oryza sativa*.

* * * * *